US012569376B2

(12) United States Patent
Schneider et al.

(10) Patent No.: US 12,569,376 B2
(45) Date of Patent: Mar. 10, 2026

(54) ABSORBENT ARTICLE WITH REUSABLE BELT AND METHODS FOR MANUFACTURING THEREOF

(71) Applicant: The Procter & Gamble Company, Cincinnati, OH (US)

(72) Inventors: Uwe Schneider, Cincinnati, OH (US); John Andrew Strasemeier, Aurora, IN (US); Sarah Marie Wade, Mt. Healthy, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 932 days.

(21) Appl. No.: 17/846,078

(22) Filed: Jun. 22, 2022

(65) Prior Publication Data

US 2022/0401272 A1 Dec. 22, 2022

Related U.S. Application Data

(60) Provisional application No. 63/213,248, filed on Jun. 22, 2021.

(51) Int. Cl.
*A61F 13/49* (2006.01)
*A61F 13/15* (2006.01)
*A61F 13/505* (2006.01)

(52) U.S. Cl.
CPC .. *A61F 13/49061* (2013.01); *A61F 13/15585* (2013.01); *A61F 13/49003* (2013.01);
(Continued)

(58) Field of Classification Search
CPC .......... A61F 13/49061; A61F 13/15585; A61F 13/49003; A61F 13/505;
(Continued)

(56) References Cited

U.S. PATENT DOCUMENTS

| 4,964,860 A | 10/1990 | Gipson et al. |
| 5,135,522 A | 8/1992 | Fahrenkrug et al. |

(Continued)

FOREIGN PATENT DOCUMENTS

| CN | 202682193 U | 1/2013 |
| EP | 3824856 A1 | 5/2021 |

(Continued)

OTHER PUBLICATIONS

PCT Search Report and Written Opinion for PCT/US2022/073071 dated Oct. 21, 2022, 11 pages.

(Continued)

*Primary Examiner* — George R Koch

*Assistant Examiner* — Christopher C Caillouet

(74) *Attorney, Agent, or Firm* — Anna E. Haller; Daniel S. Albrecht

(57) ABSTRACT

A method for forming a wearable absorbent article may comprise forming, by a system, an absorbent chassis comprising an absorbent core, a first lateral end, a second lateral end, and a length in a longitudinal direction extending between the first lateral end and the second lateral end. The method may further comprise forming, by the system, a reusable belt, and attaching, by the system, the belt to the absorbent chassis via at least one temporary fastener component formed on at least one of the absorbent chassis or the belt, resulting in formation of a wearable absorbent article unit.

14 Claims, 39 Drawing Sheets

(52) U.S. Cl.
CPC ............... *A61F 2013/15878* (2013.01); *A61F 2013/1591* (2013.01); *A61F 13/505* (2013.01)

(58) Field of Classification Search
CPC .... A61F 2013/15878; A61F 2013/1591; A61F 13/5622; A61F 13/64; A61F 13/15699
See application file for complete search history.

(56) References Cited

U.S. PATENT DOCUMENTS

| | | | |
|---|---|---|---|
| 5,226,992 A | 7/1993 | Morman | |
| 6,050,985 A | 4/2000 | Lavon et al. | |
| 6,051,094 A * | 4/2000 | Melbye | A61F 13/5622 604/389 |
| 7,754,044 B2 * | 7/2010 | Wada | A61F 13/15593 156/271 |
| 8,551,065 B2 | 10/2013 | De Angelis | |
| 9,554,952 B2 | 1/2017 | Rönnberg et al. | |
| 9,867,412 B2 | 1/2018 | Hansson et al. | |
| 10,258,518 B2 | 4/2019 | Carlén et al. | |

| | | | |
|---|---|---|---|
| 2002/0087134 A1 * | 7/2002 | Drevik | A61F 13/476 604/385.24 |
| 2002/0091368 A1 | 7/2002 | Beck et al. | |
| 2002/0111596 A1 | 8/2002 | Fletcher | |
| 2004/0186456 A1 | 9/2004 | Nawata | |
| 2006/0116656 A1 * | 6/2006 | Hendren | A61F 13/565 604/396 |
| 2019/0029897 A1 | 1/2019 | Peng | |
| 2020/0268566 A1 | 8/2020 | Tally et al. | |
| 2022/0395409 A1 | 12/2022 | Mcamis | |

FOREIGN PATENT DOCUMENTS

| | | |
|---|---|---|
| GB | 2277866 A | 11/1994 |
| WO | 2009043101 A1 | 4/2009 |
| WO | 2010071507 A1 | 6/2010 |

OTHER PUBLICATIONS

All Office Actions; U.S. Appl. No. 17/846,071, filed Jun. 22, 2022.
Unpublished U.S. Appl. No. 17/846,071, filed Jun. 22, 2022, to Uwe Schneider et al.

* cited by examiner

FIG. 2A                              FIG. 2B

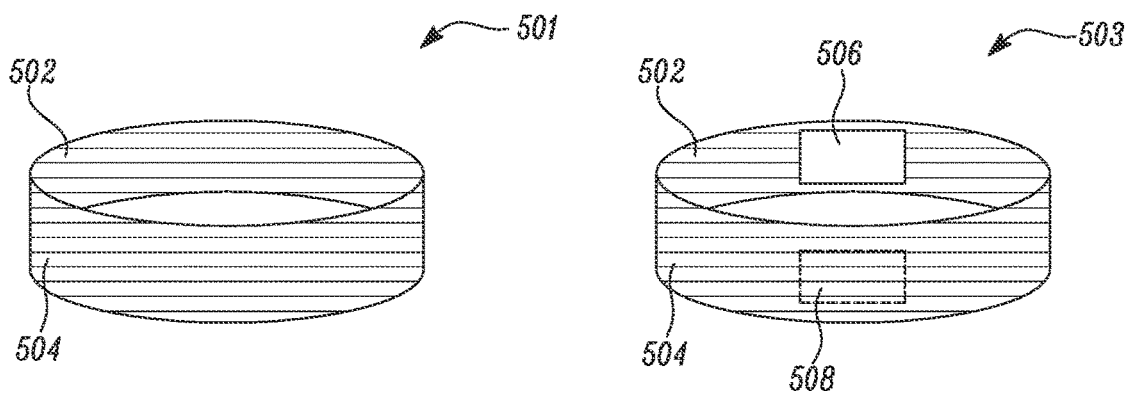
*FIG. 5A*              *FIG. 5B*
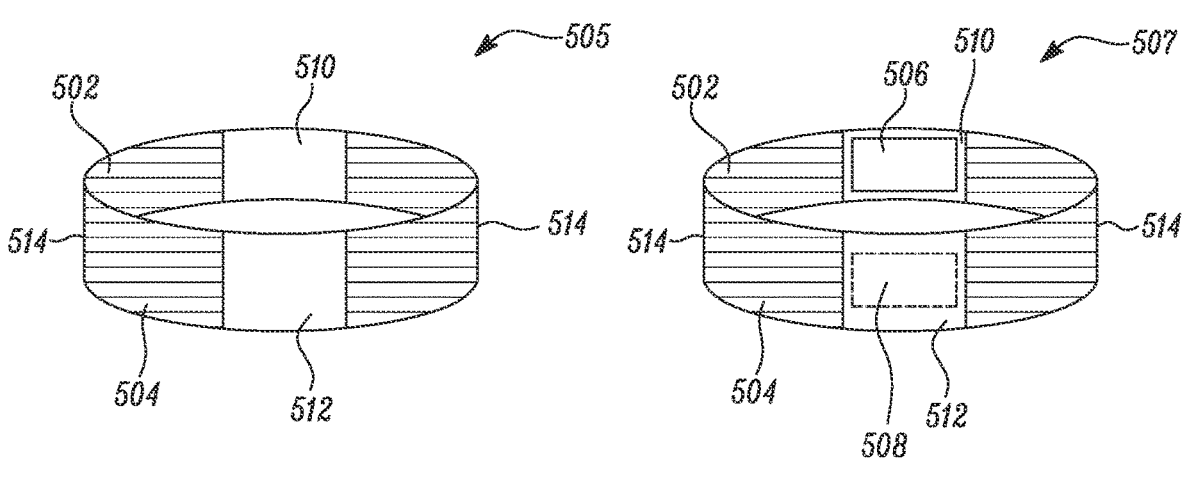
*FIG. 5C*              *FIG. 5D*

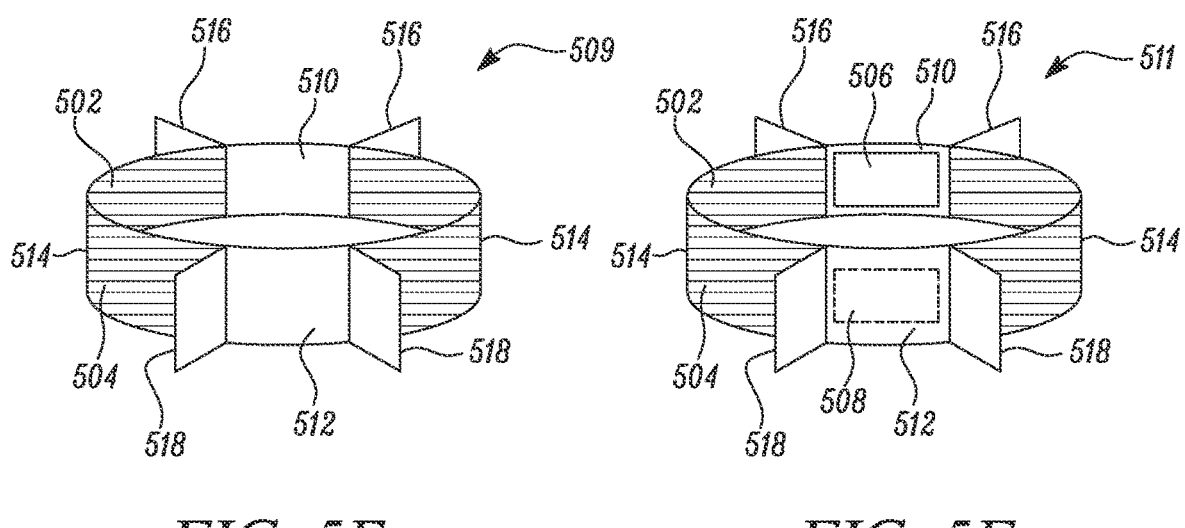
FIG. 5E          FIG. 5F
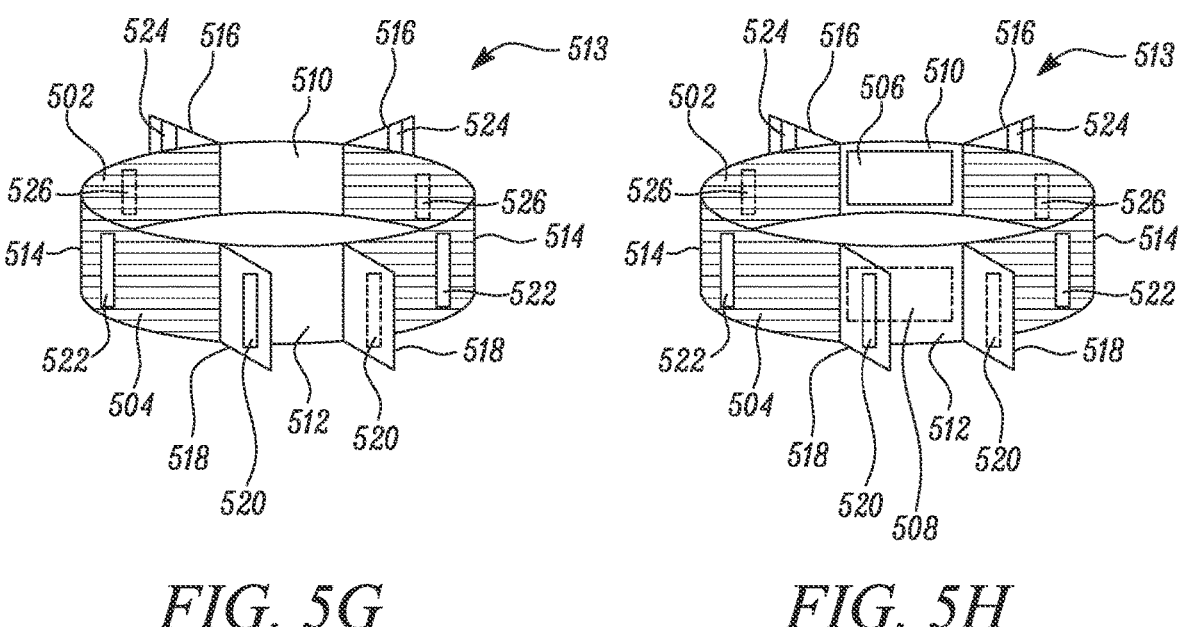
FIG. 5G          FIG. 5H

FIG. 16A                    FIG. 16B

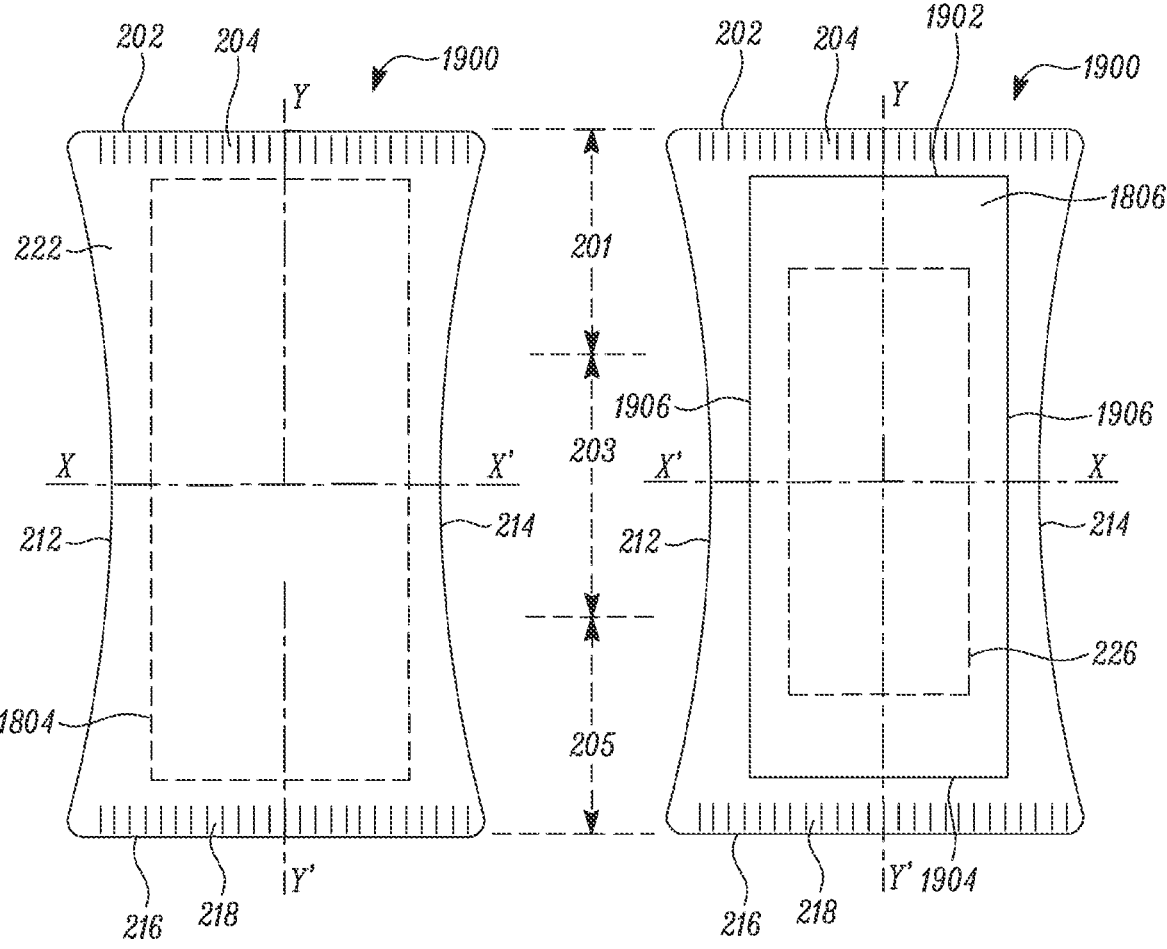
*FIG. 19A*          *FIG. 19B*

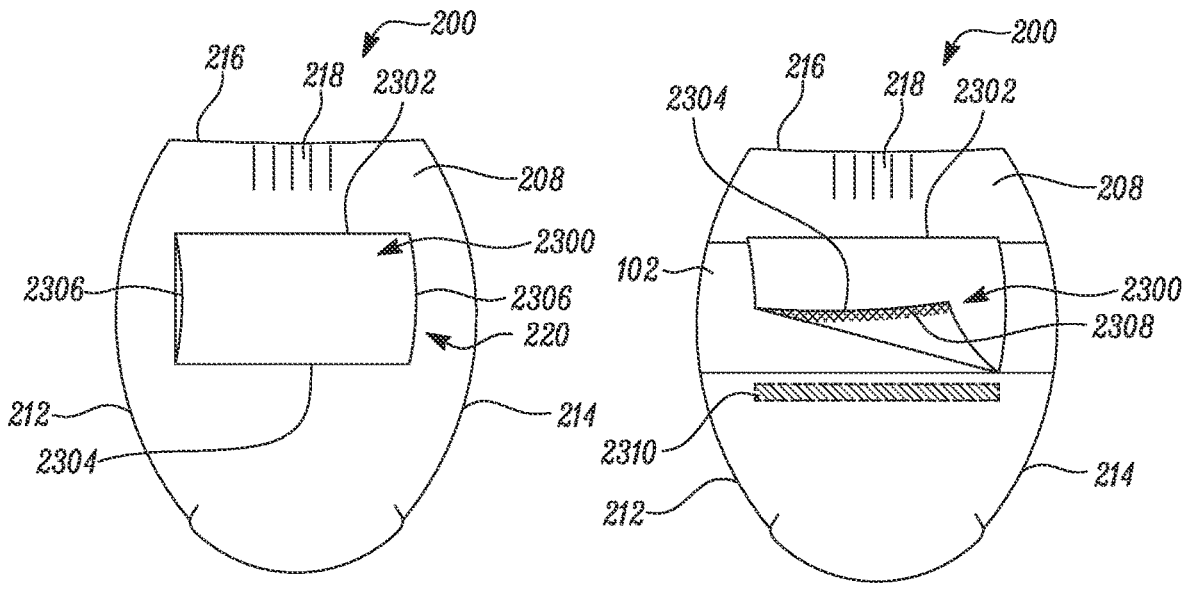
FIG. 23A                    FIG. 23B

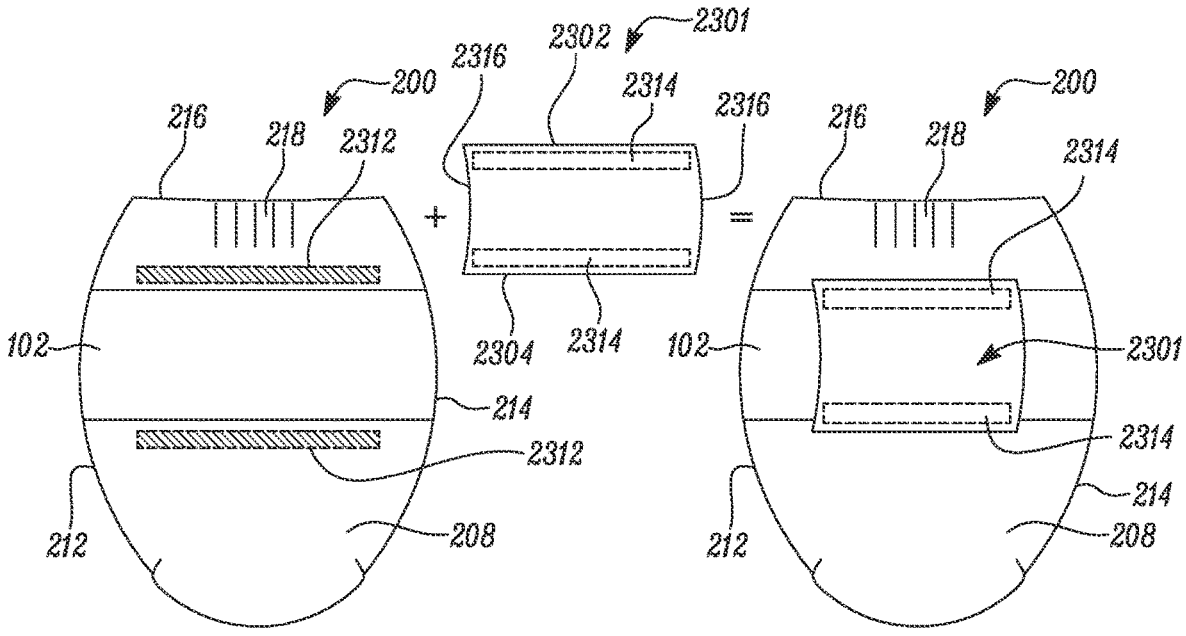
FIG. 23C                        FIG. 23D

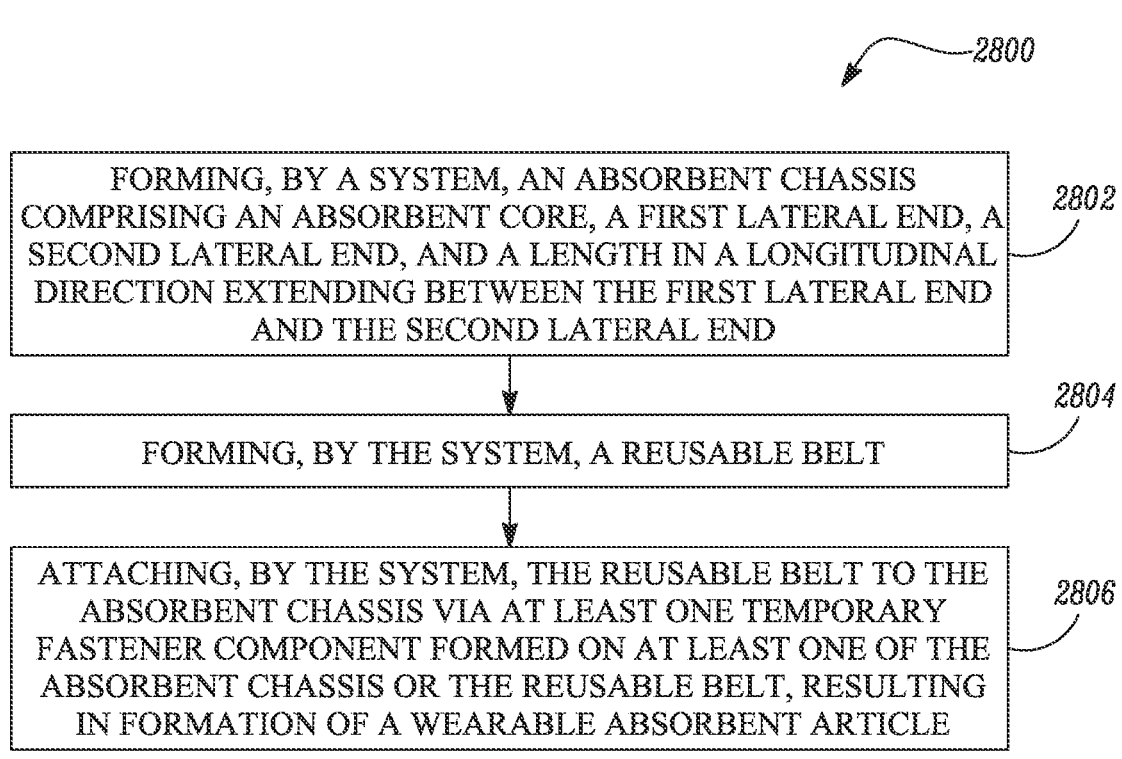

2800

2802
FORMING, BY A SYSTEM, AN ABSORBENT CHASSIS
COMPRISING AN ABSORBENT CORE, A FIRST LATERAL END, A
SECOND LATERAL END, AND A LENGTH IN A LONGITUDINAL
DIRECTION EXTENDING BETWEEN THE FIRST LATERAL END
AND THE SECOND LATERAL END

2804
FORMING, BY THE SYSTEM, A REUSABLE BELT

2806
ATTACHING, BY THE SYSTEM, THE REUSABLE BELT TO THE
ABSORBENT CHASSIS VIA AT LEAST ONE TEMPORARY
FASTENER COMPONENT FORMED ON AT LEAST ONE OF THE
ABSORBENT CHASSIS OR THE REUSABLE BELT, RESULTING
IN FORMATION OF A WEARABLE ABSORBENT ARTICLE

*FIG. 28*

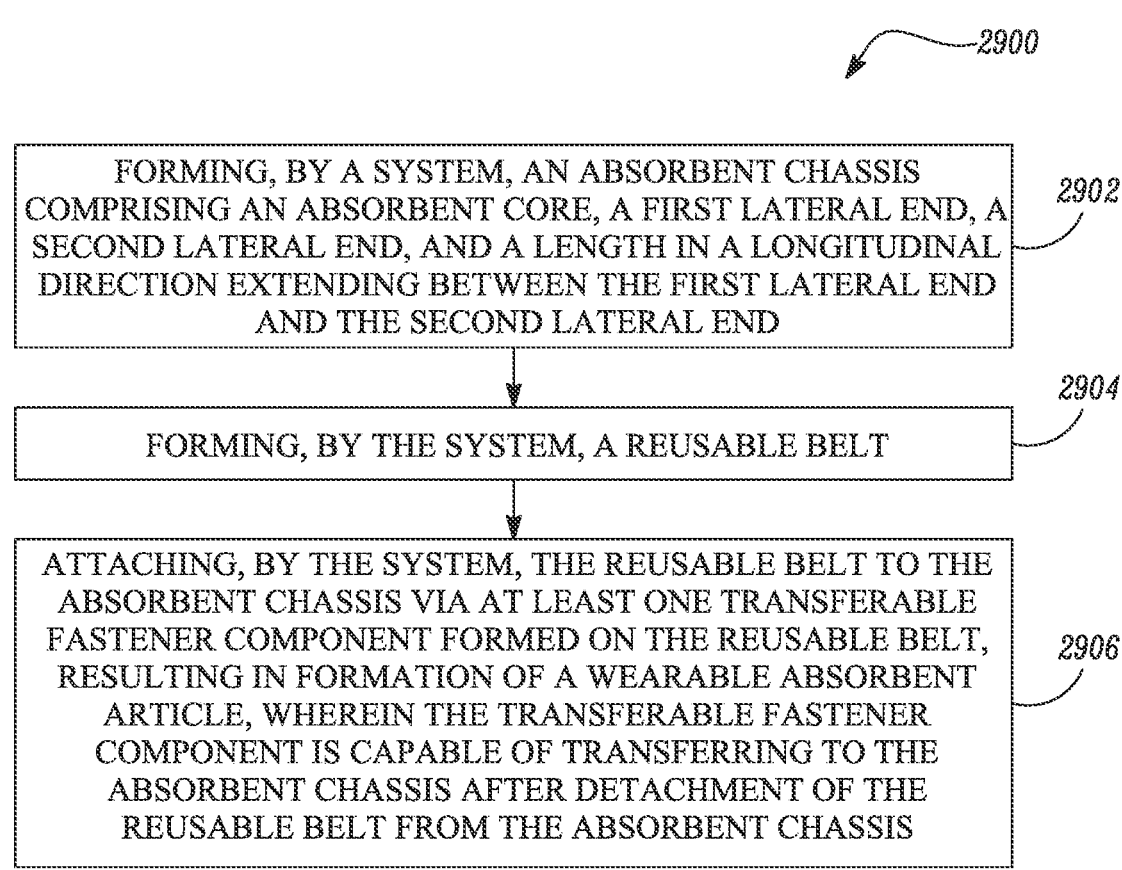

*2900*

FORMING, BY A SYSTEM, AN ABSORBENT CHASSIS COMPRISING AN ABSORBENT CORE, A FIRST LATERAL END, A SECOND LATERAL END, AND A LENGTH IN A LONGITUDINAL DIRECTION EXTENDING BETWEEN THE FIRST LATERAL END AND THE SECOND LATERAL END — *2902*

FORMING, BY THE SYSTEM, A REUSABLE BELT — *2904*

ATTACHING, BY THE SYSTEM, THE REUSABLE BELT TO THE ABSORBENT CHASSIS VIA AT LEAST ONE TRANSFERABLE FASTENER COMPONENT FORMED ON THE REUSABLE BELT, RESULTING IN FORMATION OF A WEARABLE ABSORBENT ARTICLE, WHEREIN THE TRANSFERABLE FASTENER COMPONENT IS CAPABLE OF TRANSFERRING TO THE ABSORBENT CHASSIS AFTER DETACHMENT OF THE REUSABLE BELT FROM THE ABSORBENT CHASSIS — *2906*

*FIG. 29*

3100

FORMING, BY A SYSTEM COUPLED TO A PROCESSOR, AN ABSORBENT INSERT COMPRISING AN ABSORBENT CORE, A FIRST LATERAL END, A SECOND LATERAL END, AND A LENGTH IN A LONGITUDINAL DIRECTION EXTENDING BETWEEN THE FIRST LATERAL END AND THE SECOND LATERAL END — 3102

FORMING, BY THE SYSTEM, AN OUTER COVER CONFIGURED FOR WEAR AROUND A LOWER ABDOMEN OF A WEARER, THE OUTER COVER COMPRISING A CROTCH REGION AND A WAIST REGION — 3104

ATTACHING, BY THE SYSTEM, THE ABSORBENT INSERT TO THE OUTER COVER VIA AT LEAST ONE TEMPORARY FASTENER COMPONENT FORMED ON AT LEAST ONE OF THE OUTER COVER OR THE ABSORBENT INSERT, RESULTING IN FORMATION OF A WEARABLE ABSORBENT ARTICLE UNIT — 3106

*FIG. 31*

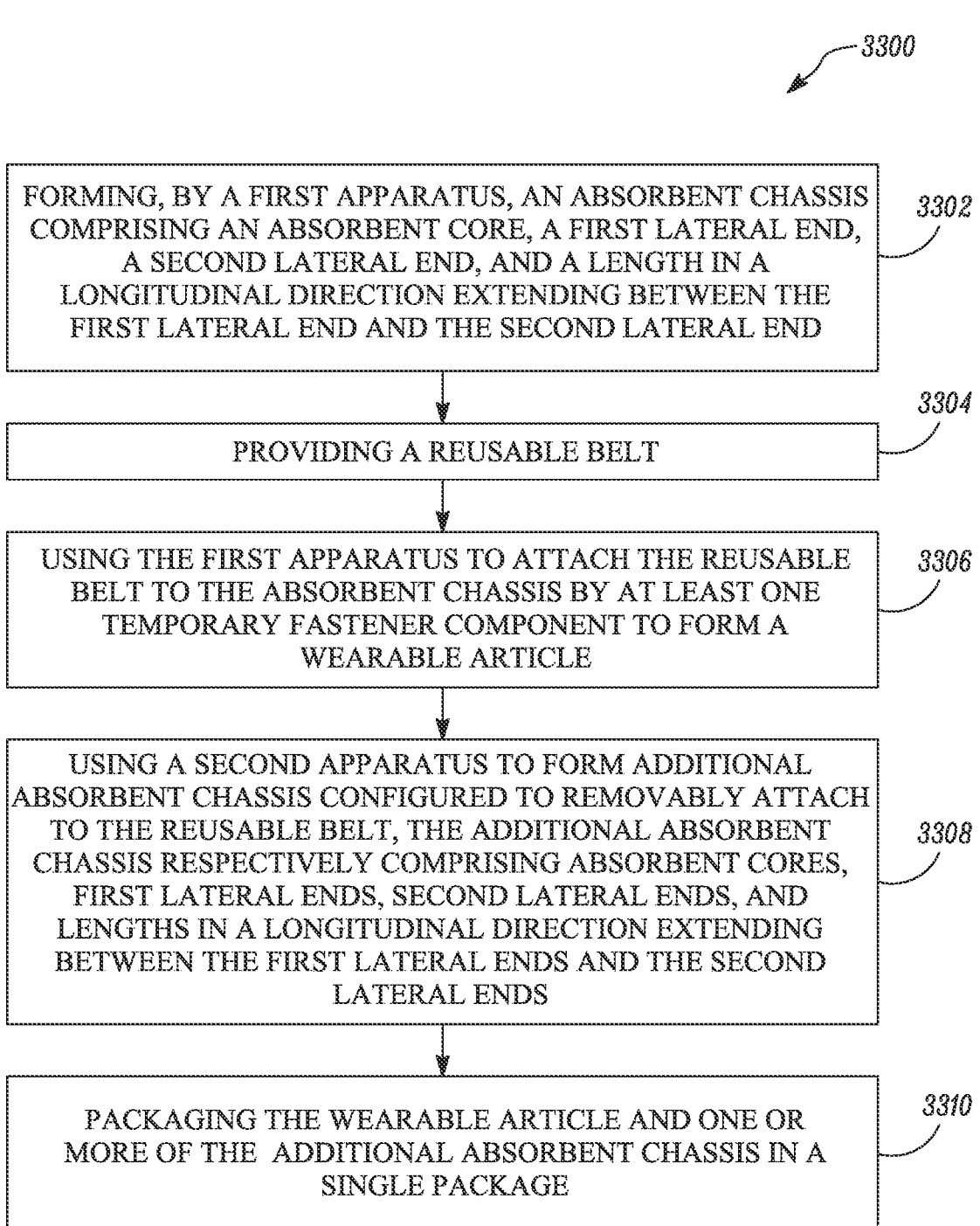

*3300*

FORMING, BY A FIRST APPARATUS, AN ABSORBENT CHASSIS COMPRISING AN ABSORBENT CORE, A FIRST LATERAL END, A SECOND LATERAL END, AND A LENGTH IN A LONGITUDINAL DIRECTION EXTENDING BETWEEN THE FIRST LATERAL END AND THE SECOND LATERAL END    *3302*

PROVIDING A REUSABLE BELT    *3304*

USING THE FIRST APPARATUS TO ATTACH THE REUSABLE BELT TO THE ABSORBENT CHASSIS BY AT LEAST ONE TEMPORARY FASTENER COMPONENT TO FORM A WEARABLE ARTICLE    *3306*

USING A SECOND APPARATUS TO FORM ADDITIONAL ABSORBENT CHASSIS CONFIGURED TO REMOVABLY ATTACH TO THE REUSABLE BELT, THE ADDITIONAL ABSORBENT CHASSIS RESPECTIVELY COMPRISING ABSORBENT CORES, FIRST LATERAL ENDS, SECOND LATERAL ENDS, AND LENGTHS IN A LONGITUDINAL DIRECTION EXTENDING BETWEEN THE FIRST LATERAL ENDS AND THE SECOND LATERAL ENDS    *3308*

PACKAGING THE WEARABLE ARTICLE AND ONE OR MORE OF THE ADDITIONAL ABSORBENT CHASSIS IN A SINGLE PACKAGE    *3310*

*FIG. 33*

ABSORBENT ARTICLE WITH REUSABLE BELT AND METHODS FOR MANUFACTURING THEREOF

CROSS REFERENCE TO RELATED APPLICATIONS

This application claims the benefit, under 35 U.S.C. § 119(e), of U.S. Provisional Application No. 63/213,248, filed Jun. 22, 2021, which is incorporated by reference herein in its entirety.

FIELD

The present invention relates generally to the field of wearable absorbent articles having reusable belts and disposable absorbent chassis or inserts and methods for manufacturing thereof.

BACKGROUND

It has long been known that absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). Absorbent articles may be made of reusable materials, which offers the advantage of utilizing raw materials from renewable and recyclable resources and less waste. However, reusable absorbent articles present difficulties relating to sanitation needs, in handling, laundering and effectively sanitizing soiled diapers for re-use. Further, reusable cloth diapers may be relatively unreliable and leak and may promote over-hydration of the wearer's skin causing diaper rash.

On the other hand, absorbent articles may be fully disposable, increasing consumer convenience by eliminating the need for laundering. Further, many current disposable absorbent articles have structures that make them relatively more effective at containing exudates and conveying and storing liquid exudates away from the wearer's skin. Some have features that enable them to "breathe", thereby reducing humidity inside the diaper, and some even include skin care compositions that are transferred to the skin when the diaper is worn. Although disposable conventional absorbent articles have many benefits, there is a continuous desire to reduce disposable material consumption and further improve consumer acceptance of single use products.

To address the foregoing concerns, it has been proposed to manufacture two-piece absorbent articles with a reusable outer cover and a detachable absorbent insert that may be reusable or disposable. In this way, the insert can be made with different materials to enhance performance and less energy may be consumed as the insert can be separately laundered. Further, where disposable, the inserts may be made with materials known to provide even more superior performance while minimizing the amount of waste as the whole article need not be disposed.

Despite several designs of a two-piece absorbent article, the designs still present some disadvantages. In particular, articles may not provide sufficient attachment between the insert and outer cover to ensure a snug and comfortable fit. Further, some converting lines may be inflexible in that line changes that would be required to accommodate the production of different types of product designs with reusable belts would be so time consuming and/or expensive as to be economically impractical. For instance, some converting lines are custom designed and built to make specific products within a narrow range of parameters and operating conditions. For example, converting lines may be custom designed to make only taped diapers, whereas other converting lines may be custom designed to make only pant diapers with a permanently glued belt to chassis configuration. Thus, such custom converting lines may be used to produce particular types of diapers, e.g., taped or pant, in certain markets in an effort to provide a good match with business needs. However, the inflexibility of such converting lines to produce more than one type of product can place unwanted limitations on a manufacturer's ability to provide multiple product offerings in some markets.

Thus, there is an ongoing need for absorbent articles that incorporate reusable belts that require less material and can be made without undesirable complexity using a substantial number of the machines and processes employed by existing converting lines. Further, there is a need for absorbent articles with reusable belts that maintain desired fit during wear and after loading. There is also a need to provide targeted fastening zones in a cost-efficient manner.

SUMMARY

The present invention comprises the features of the independent claims herein. In one embodiment, an absorbent article comprises an absorbent chassis and a belt. The absorbent chassis comprises an absorbent core, a first lateral end, a second lateral end, and a length in a longitudinal direction extending between the first lateral end and the second lateral end. The belt comprises a continuous ring of at least one material configured for wear around a waist of a wearer that is operatively engageable with the first lateral end and the second lateral end, wherein at least a portion of the continuous ring is expandable, and wherein the absorbent chassis is disposable, and the reusable belt is reusable with and re-attachable to one or more additional absorbent chassis.

In another embodiment, an absorbent article comprises an absorbent chassis and a multi-piece reusable belt for wear around a waist of a wearer. The absorbent chassis comprises an absorbent core, a first lateral end, a second lateral end, and a length in a longitudinal direction extending between the first lateral end and the second lateral end. The multi-piece reusable belt and comprises two or more pieces that removably attach to and connect the first lateral end and the second lateral end. In some implementations, the two or more pieces comprise a first side piece that removably attaches to and connects the first lateral end and the second lateral end on a first side of the waist, and a second side piece that removably attaches to and connects the first lateral end and the second lateral end on a second side of the waist. In other implementations, the two or more pieces comprise a front piece that removably attaches to and connects to the first lateral end adjacent to an abdomen of the wearer, and a back piece that removably attaches to and connects to the second lateral end and opposite sides of the front piece.

In another embodiment, an absorbent article comprises an absorbent chassis and a reusable strip belt for wear around a waist of a wearer. The absorbent chassis comprises an absorbent core, a first lateral end, a second lateral end, and a length in a longitudinal direction extending between the first lateral end and the second lateral end. The reusable strip belt comprises two opposing ends connected to one another by a strip portion of material, the strip belt being adapted to wrap around a portion of a waist of a wearer and comprising one or more fastening components, wherein the first lateral end comprises is operatively engageable with the one or more fastening components.

Methods for forming absorbent articles incorporating reusable belts are also provided. In an embodiment, a method comprises forming, by a system, an absorbent chassis comprising an absorbent core, a first lateral end, a second lateral end, and a length in a longitudinal direction extending between the first lateral end and the second lateral end. The method further comprises forming, by the system, a reusable belt, and attaching, by the system, the reusable belt to the absorbent chassis via at least one temporary fastener component formed on at least one of the absorbent chassis or the reusable belt, resulting in formation of a wearable absorbent article.

In another embodiment, a method comprises forming, by a first apparatus, an absorbent chassis comprising an absorbent core, a first lateral end, a second lateral end, and a length in a longitudinal direction extending between the first lateral end and the second lateral end. The method further comprises providing a reusable belt and using the first apparatus to attach the reusable belt to the absorbent chassis by at least one temporary fastener component to form a wearable article. The method further comprises using a second apparatus to form additional absorbent chassis configured to removably attach to the reusable belt, the additional absorbent chassis respectively comprising absorbent cores, first lateral ends, second lateral ends, and lengths in a longitudinal direction extending between the first lateral ends and the second lateral ends.

In another embodiment, a method comprises forming, by a system, an absorbent chassis comprising an absorbent core, a first lateral end, a second lateral end, and a length in a longitudinal direction extending between the first lateral end and the second lateral end. The method further comprises forming, by the system, a reusable belt, and attaching, by the system, the reusable belt to the absorbent chassis via at least one transferable fastener component formed on the reusable belt, resulting in formation of a wearable absorbent article, wherein the transferable fastener component is capable of transferring to the absorbent chassis after detachment of the reusable belt from the absorbent chassis.

BRIEF DESCRIPTION OF THE DRAWINGS

FIGS. 5A-5I are depictions of various example continuous ring belts in accordance with different embodiments;

4

Figure 6:
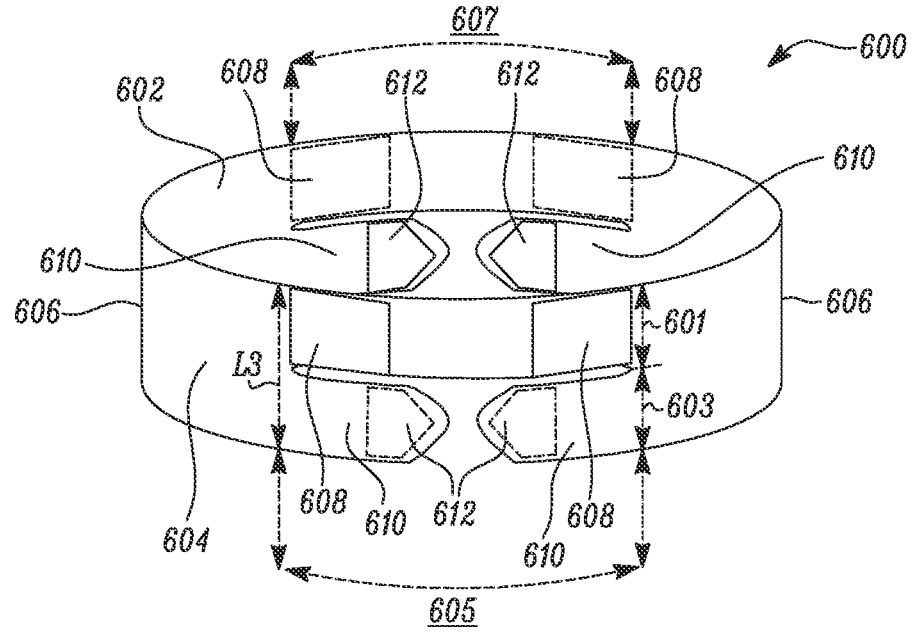
FIG. 6 provides an example partially continuous ring belt adapted for attaching to a absorbent chassis.
Figure 7:
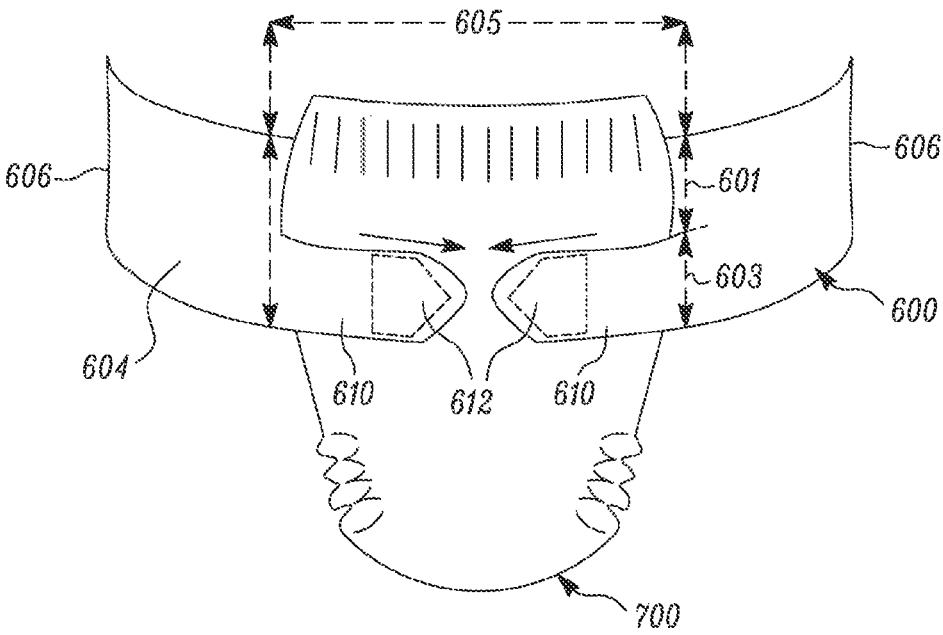
Figures 8A, 8B, 8C, 8D:
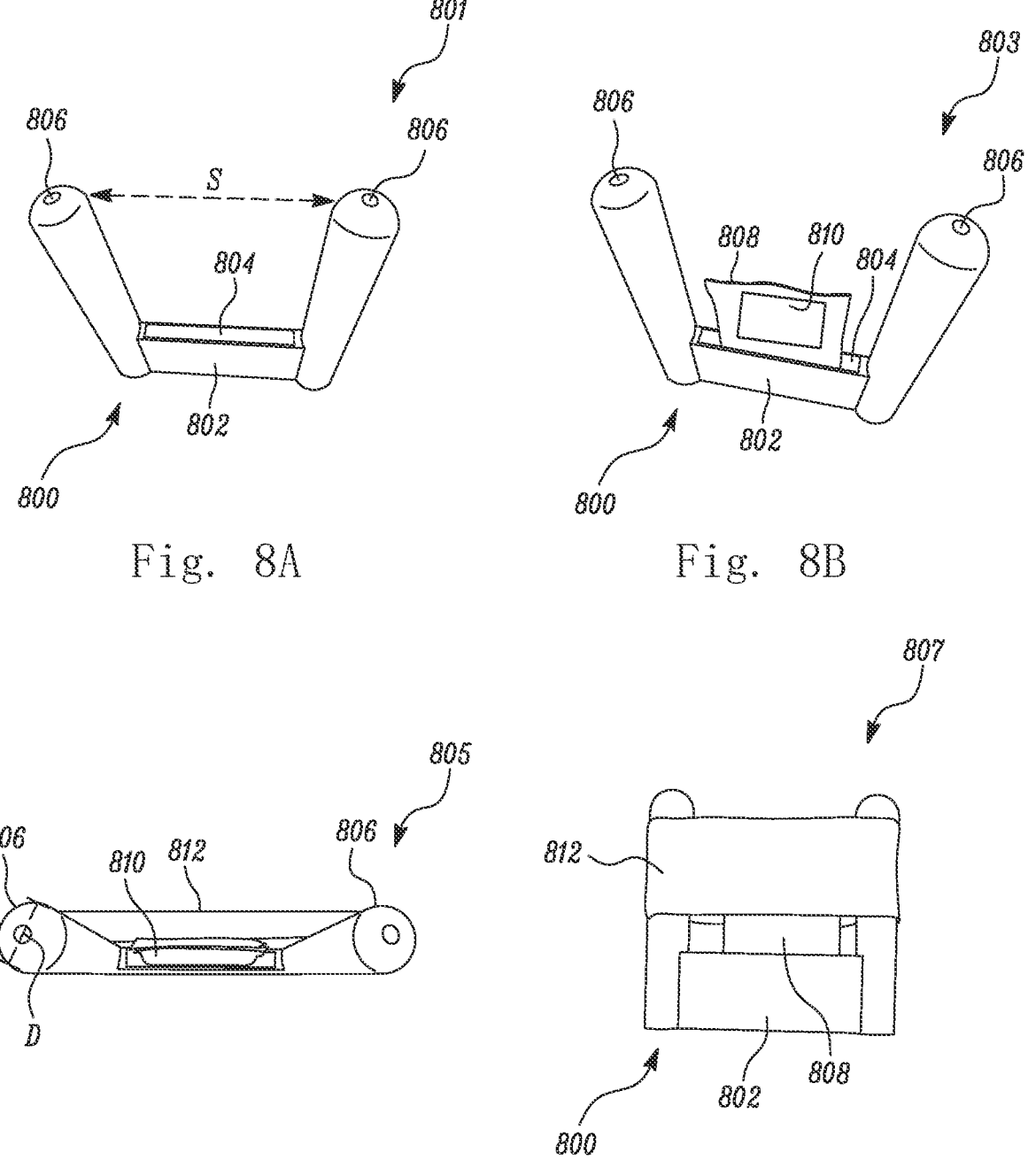
Figure 9:
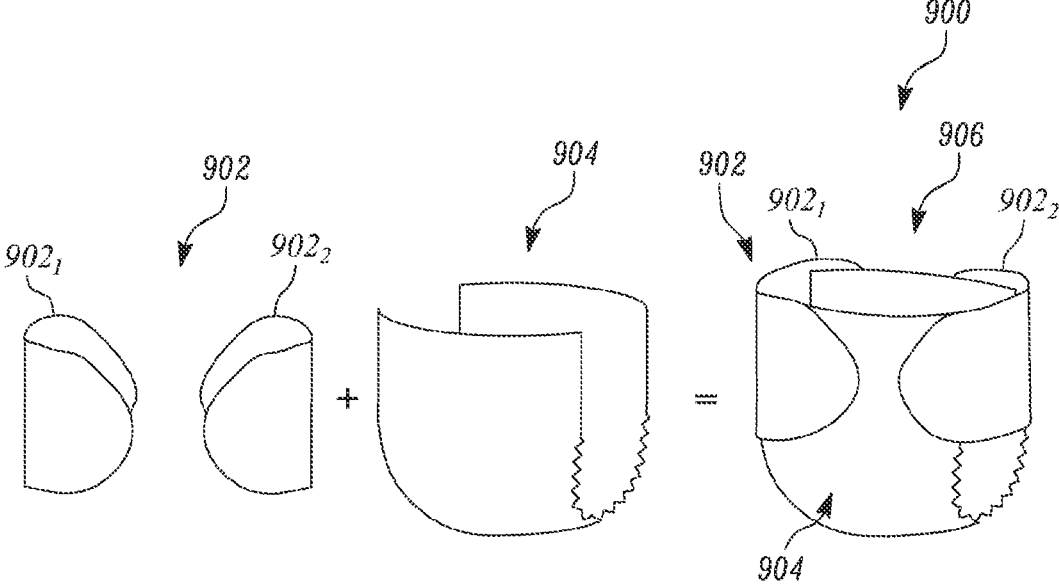
Figure 10:
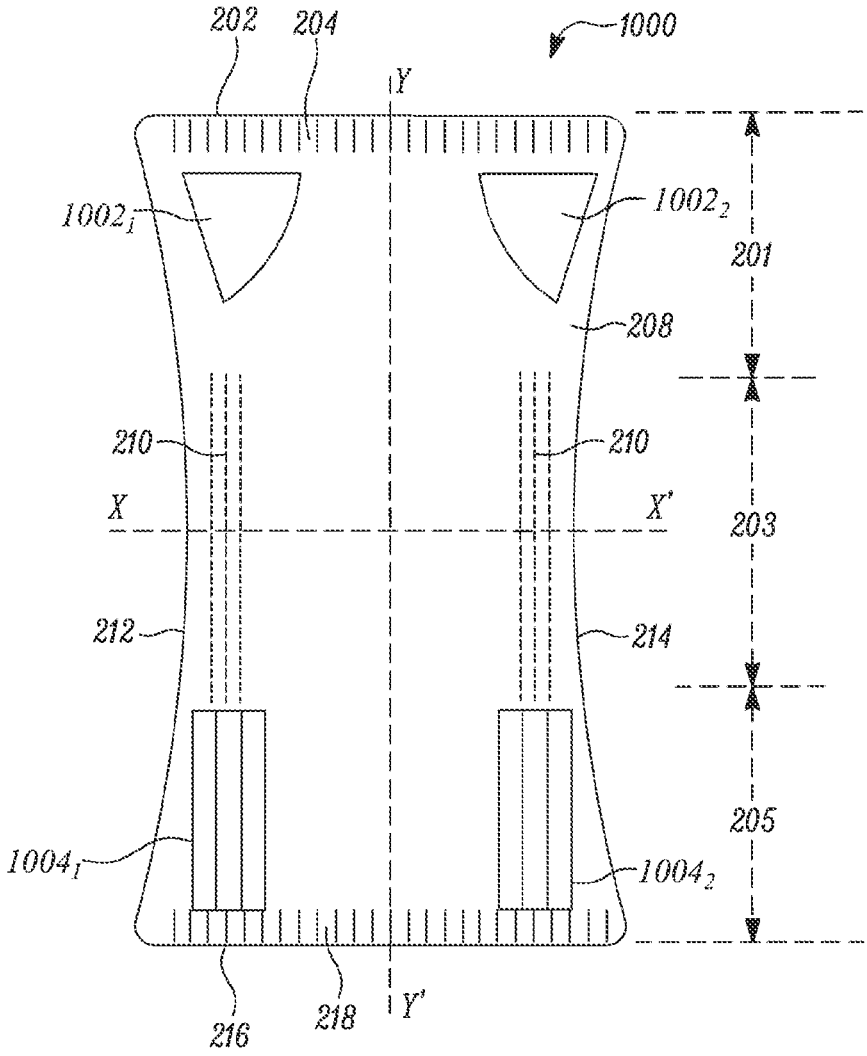
Figures 11A, 11B:
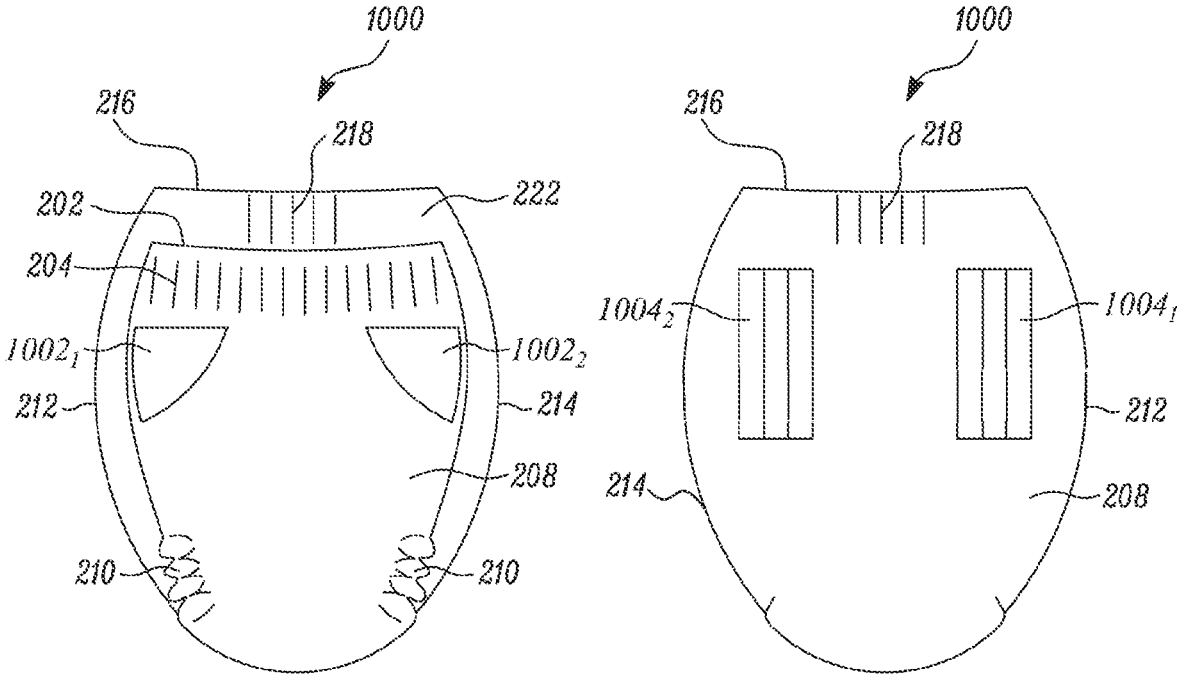
Figure 12A:
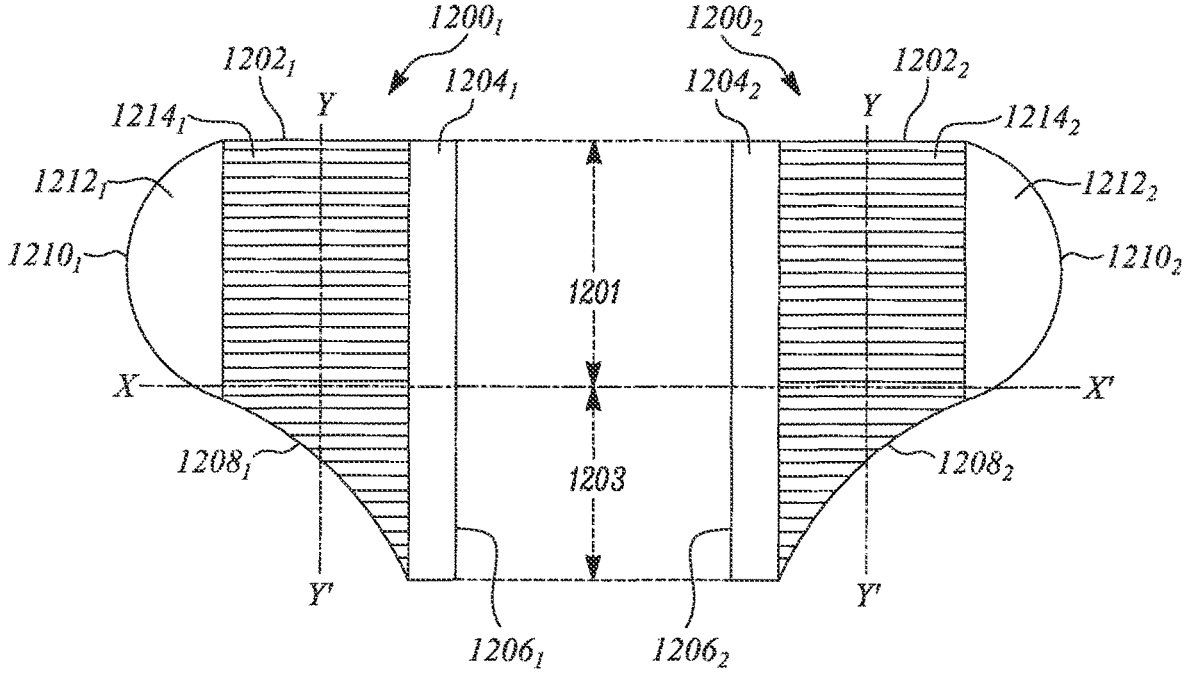
Figure 12B:
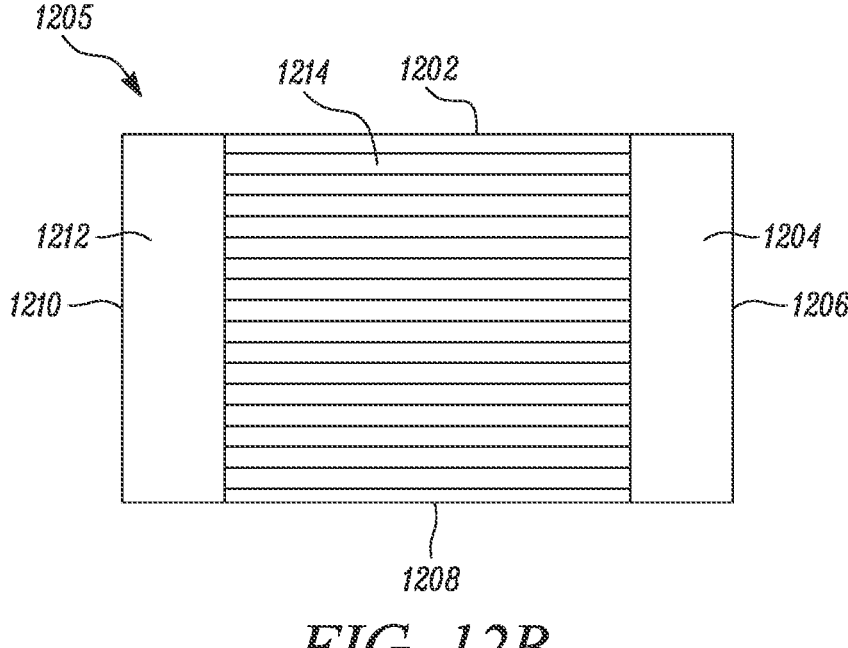
Figure 12C:
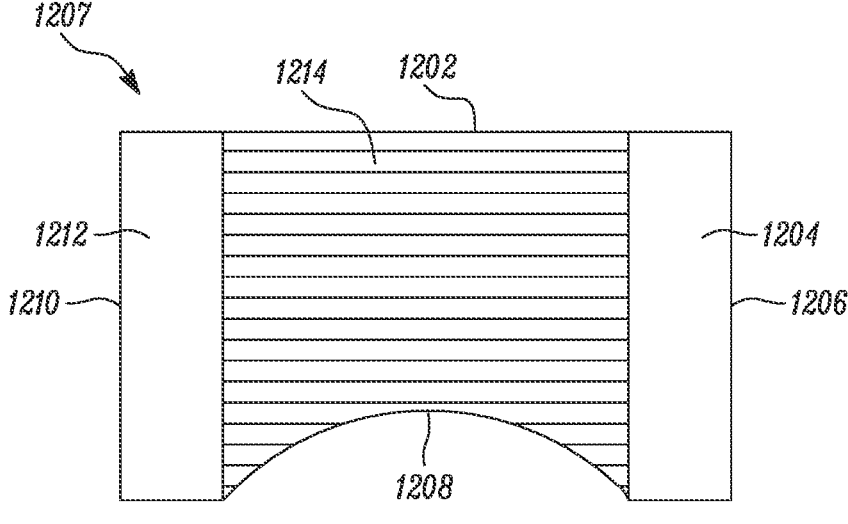
Figure 13:
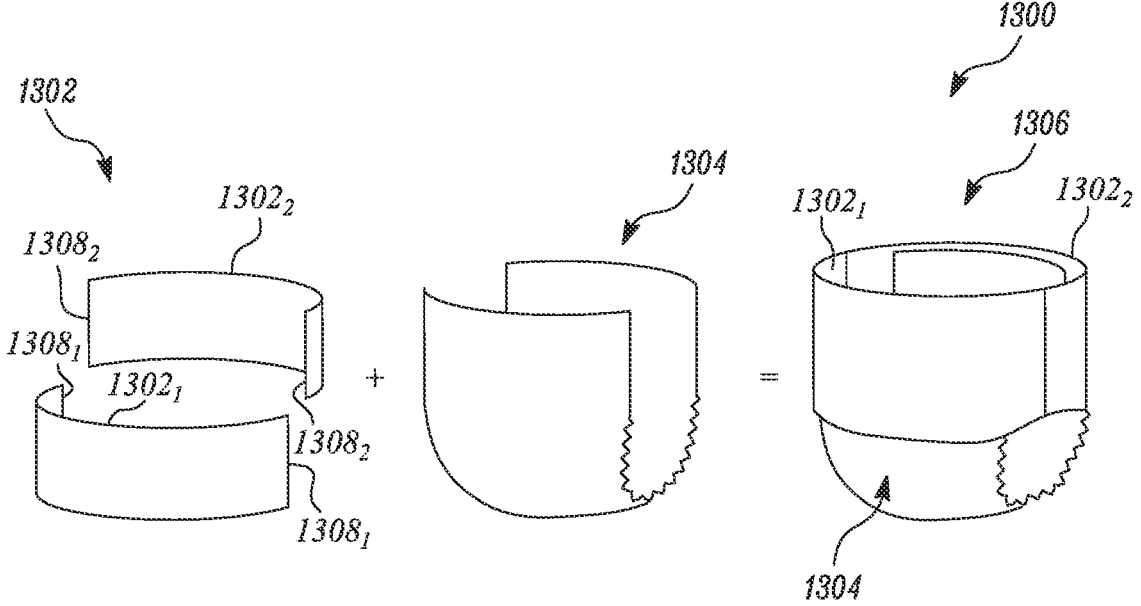
Figure 14:
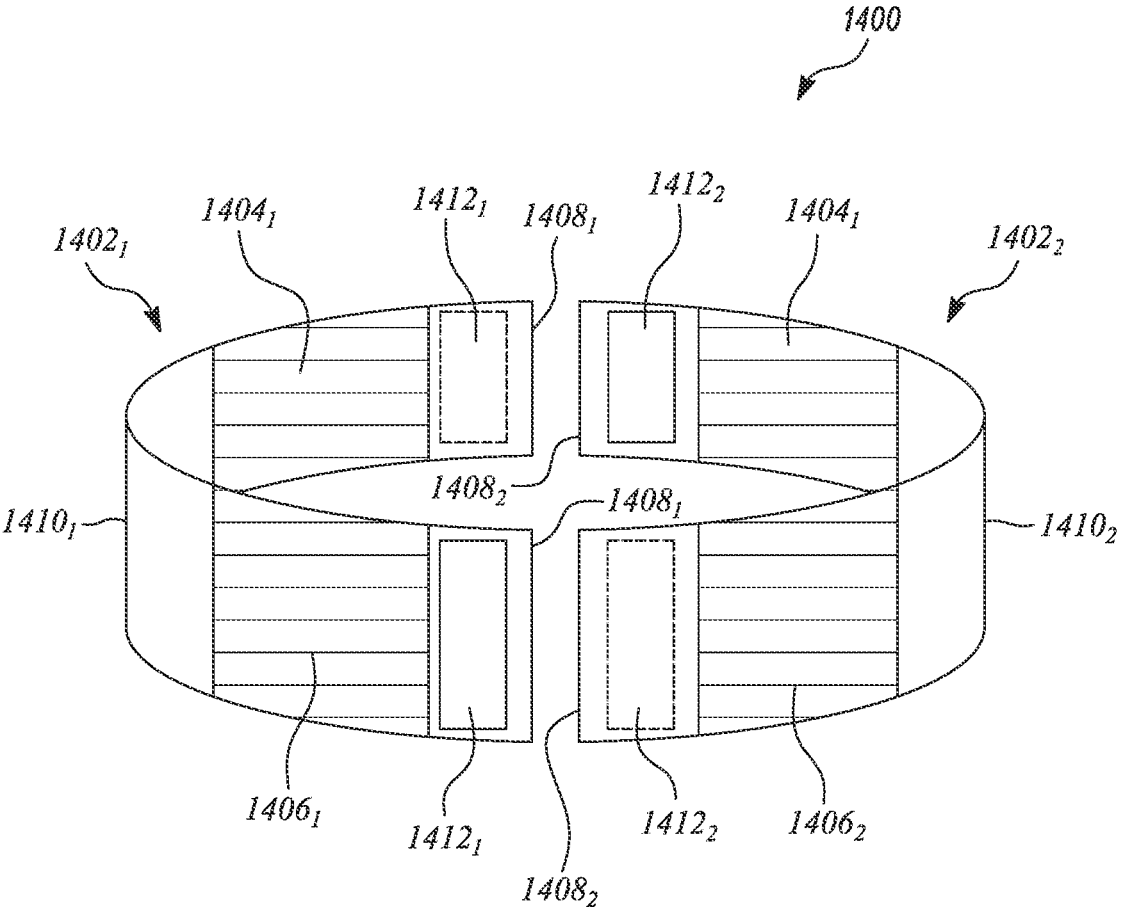
Figure 15:
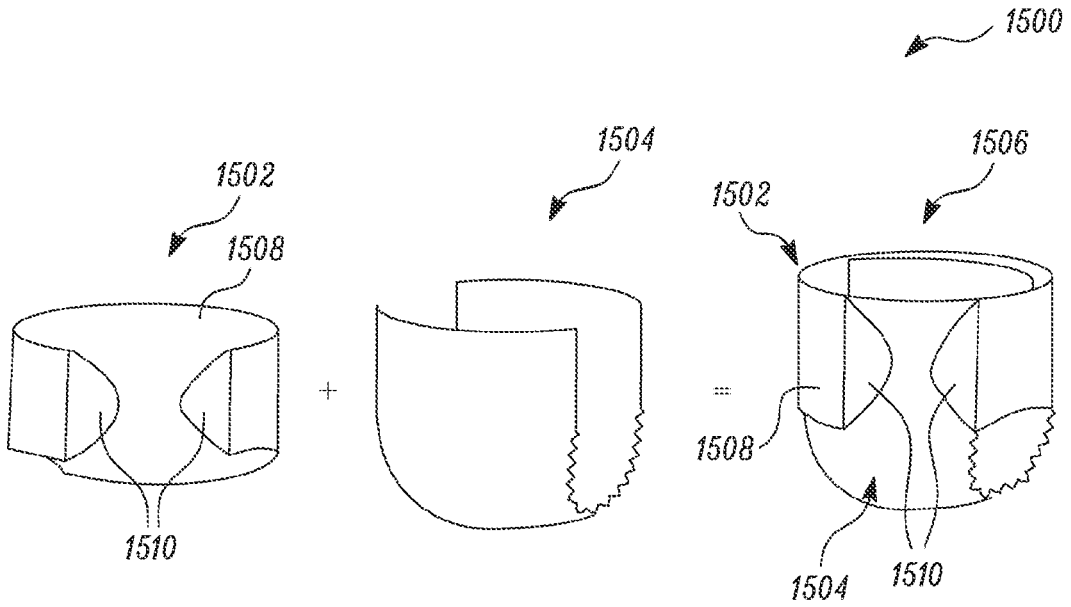
Figure 16:
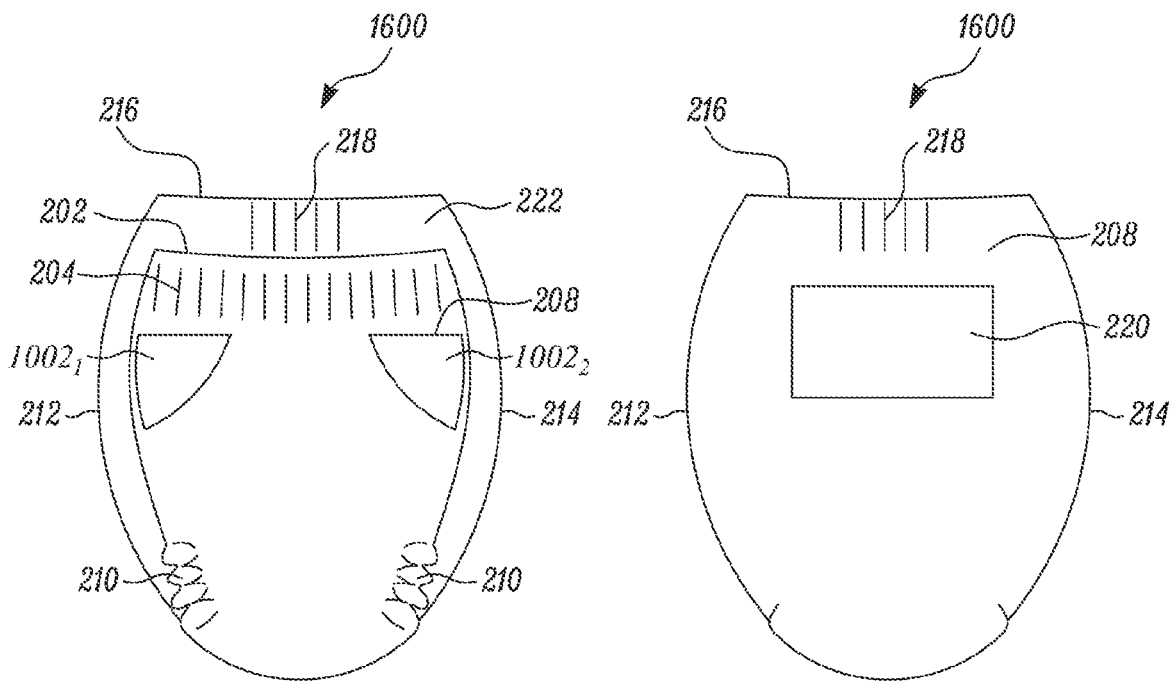
Figure 17:
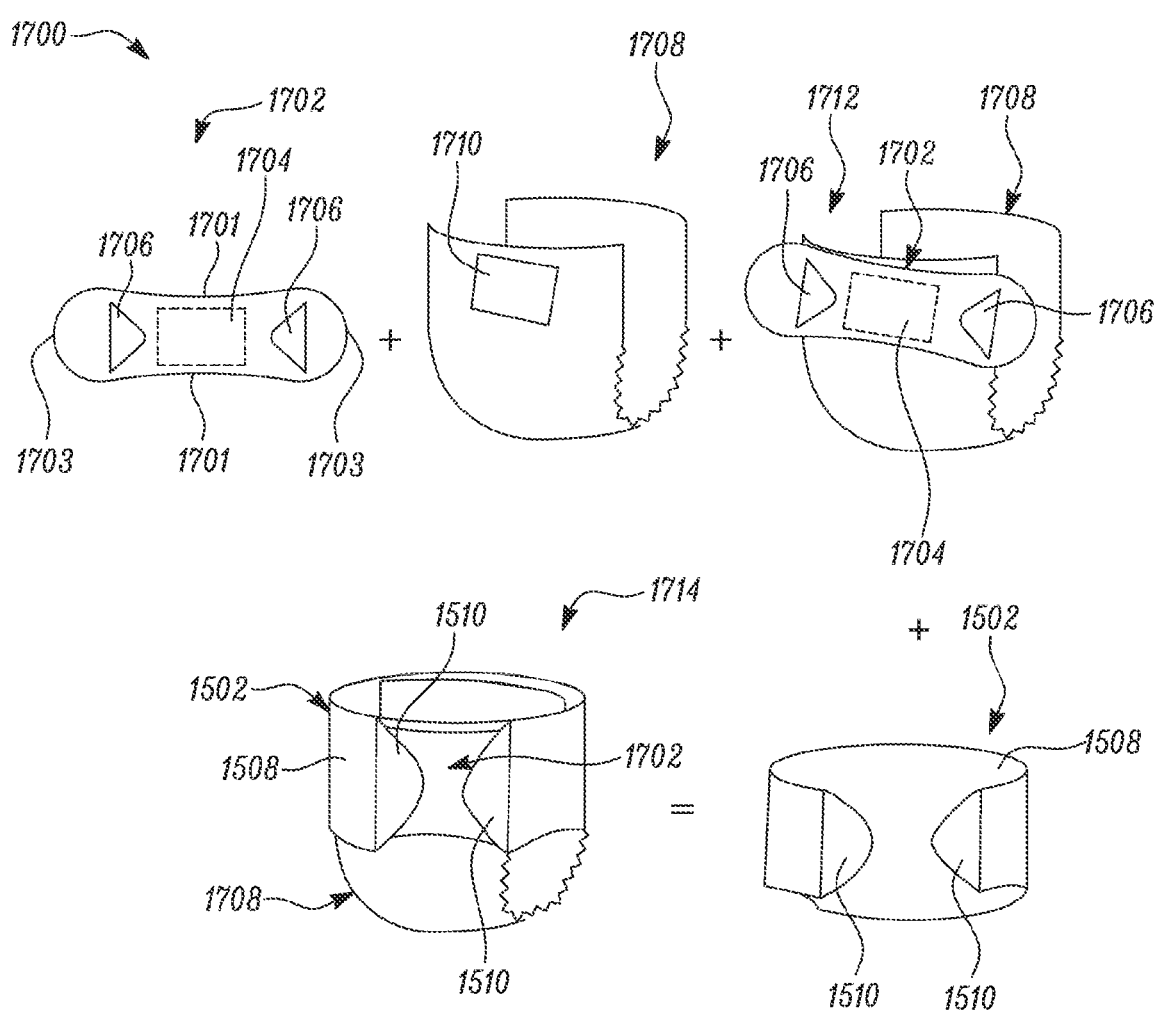
Figure 18A:
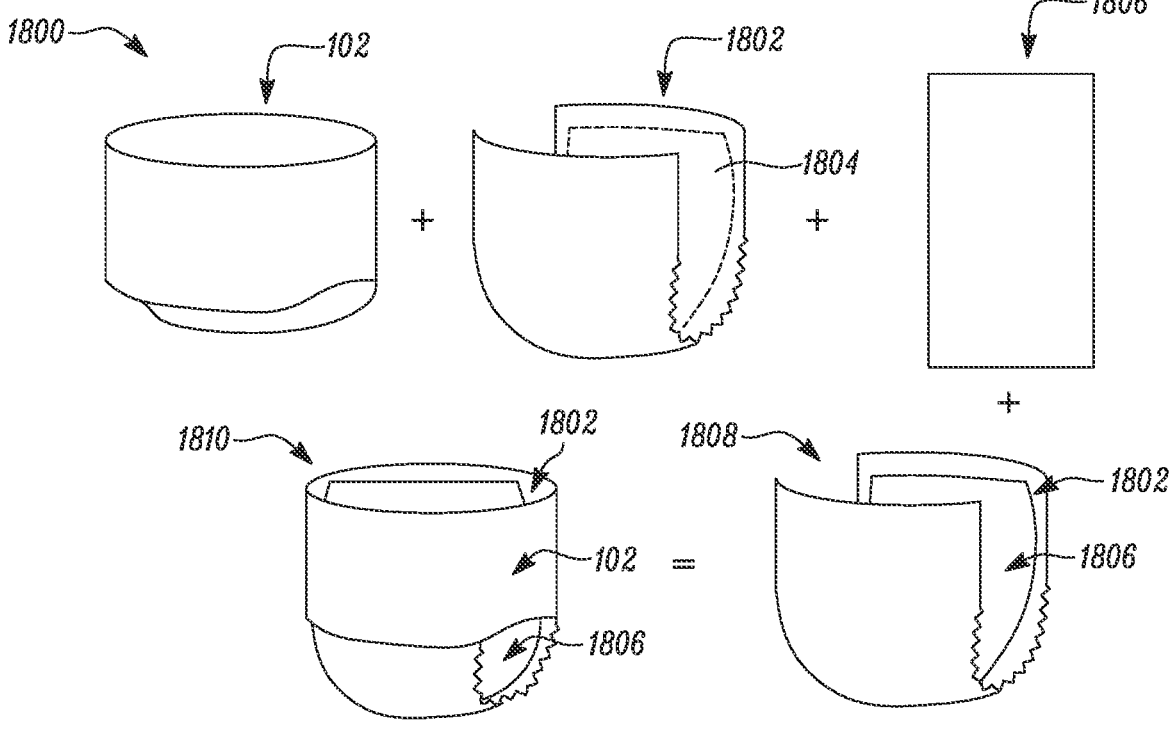
Figure 18B:
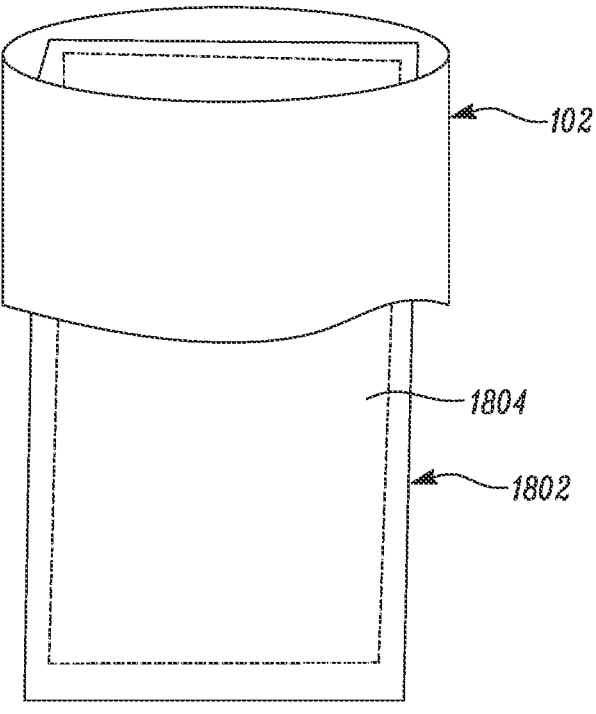
Figure 20:
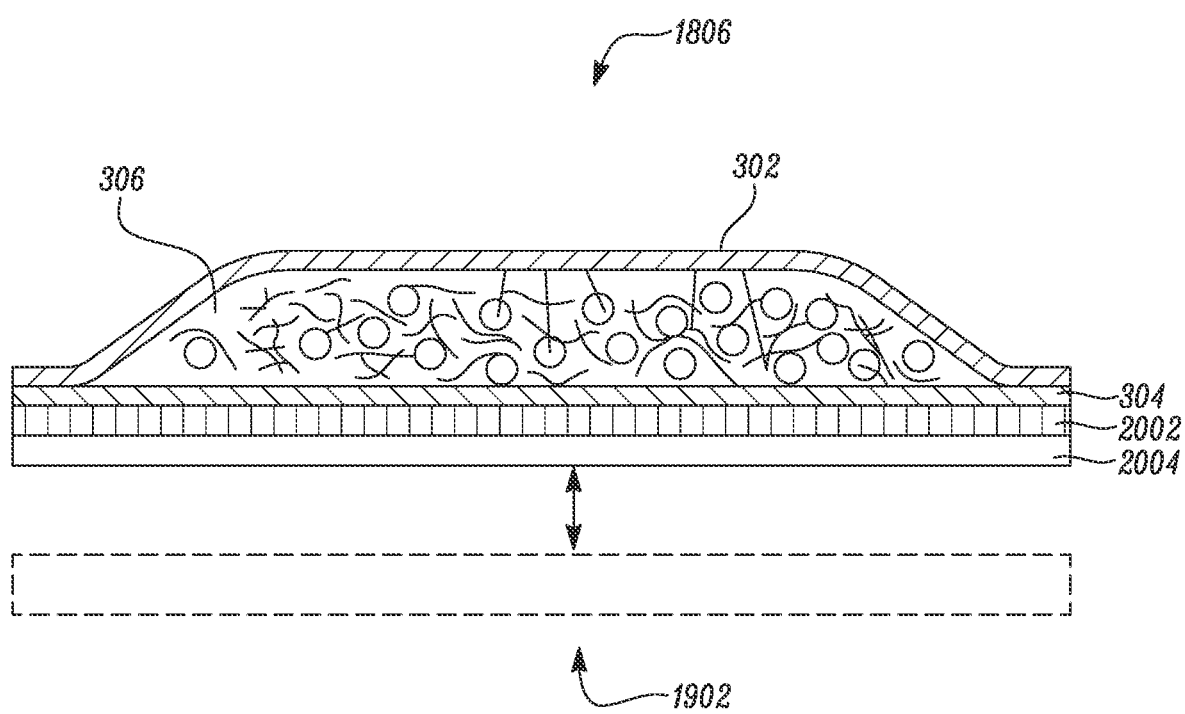
Figure 21:
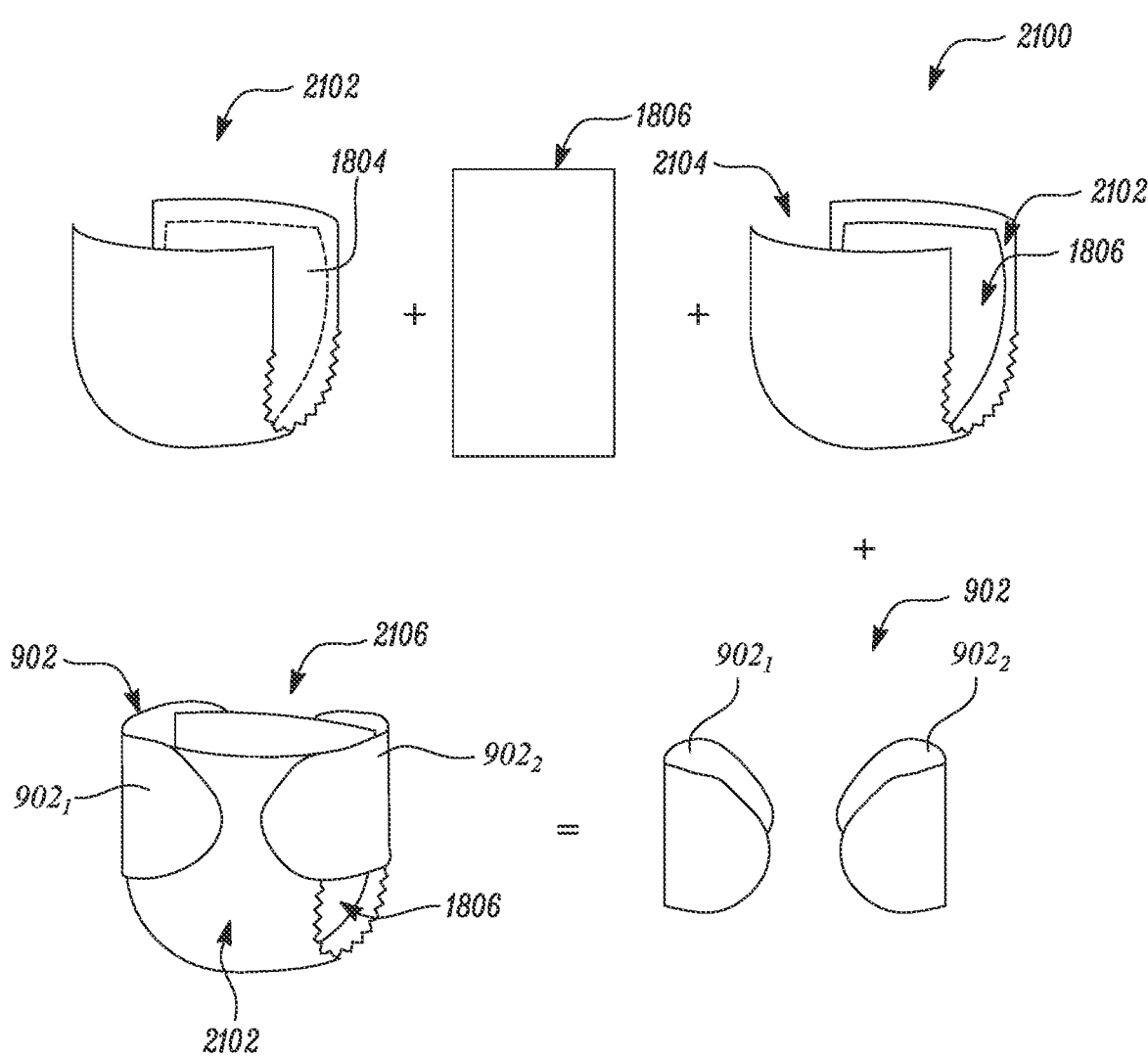
Figure 22:
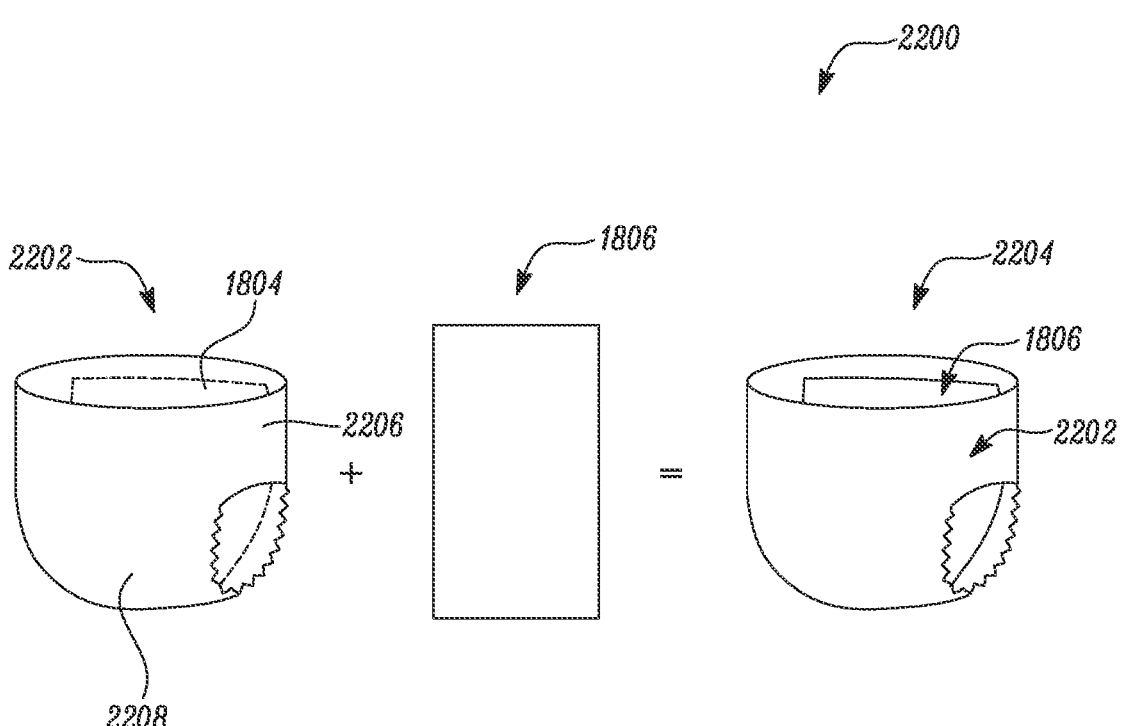
Figure 24:
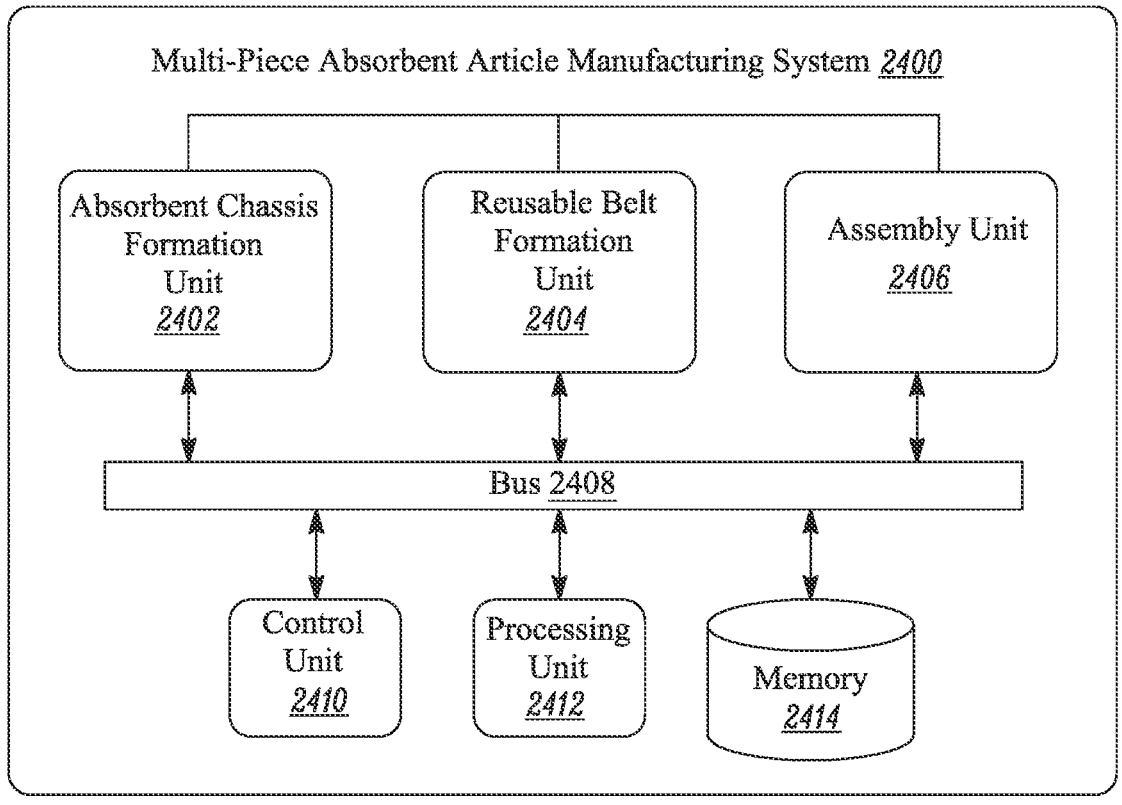
Figure 25:
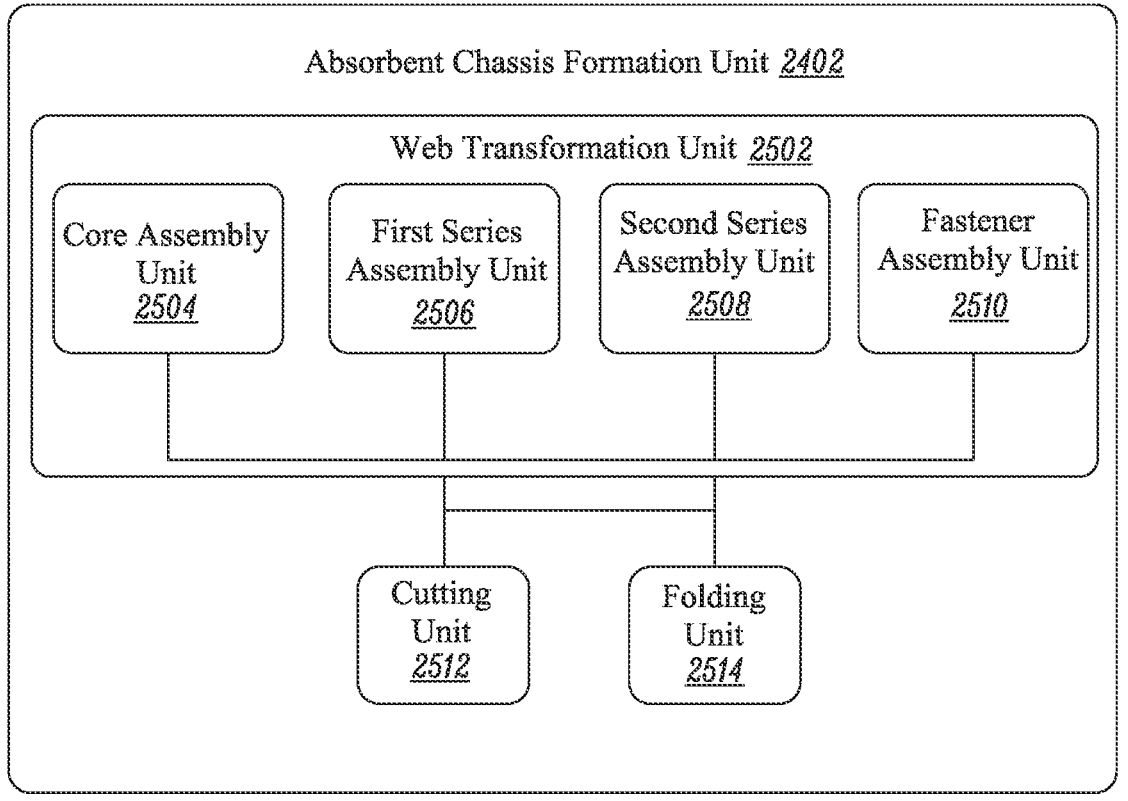
Figure 26:
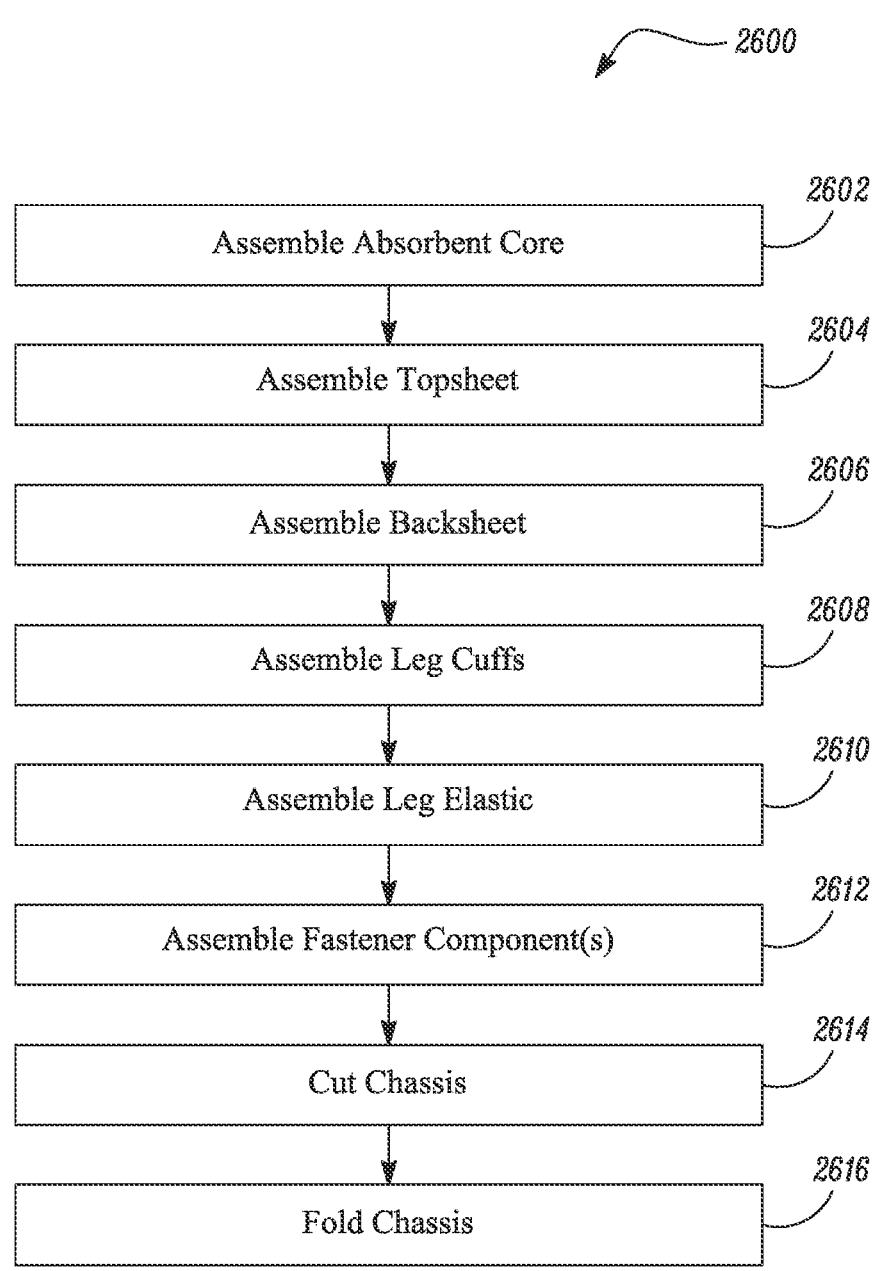
Figure 27:
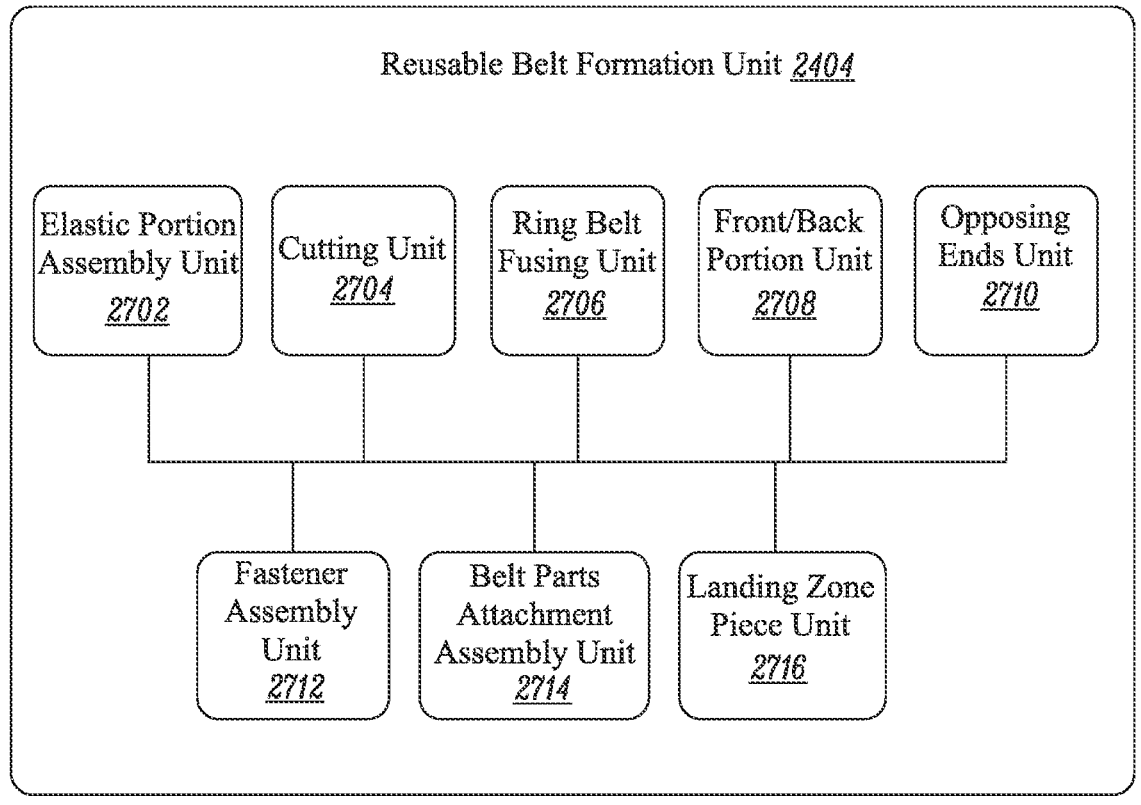

FIG. 7 illustrates attachment of the partially continuous ring belt of FIG. 6 to an absorbent chassis;

FIGS. 8A-8D provide images of an example apparatus that facilitate attaching a continuous ring reusable belt to a disposable chassis;

FIG. 9 provides a high-level assembly configuration for forming a wearable absorbent article comprising a side-piece reusable belt and an absorbent chassis;

FIG. 10 is a plain view of an outer (garment-facing) surface of an absorbent chassis as opened and laid flat in accordance with the two-side piece reusable belt embodiment;

FIG. 11A is a front-side perspective of the disposable chassis shown in FIG. 10 in a folded configuration;

FIG. 11B is a back-side perspective of the disposable chassis shown in FIG. 10 in a folded configuration;

FIG. 12A is a view of example side pieces of a side piece reusable belt;

FIGS. 12B-12C provide example reusable sidepieces for use with an absorbent chassis in accordance with alternative embodiments;

FIG. 13 provides a high-level assembly configuration for forming a wearable absorbent article comprising a front/back piece reusable belt and an absorbent chassis;

FIG. 14 presents an example front/back piece reusable belt;

FIG. 15 provides a high-level assembly configuration for forming a wearable absorbent article comprising a reusable belt and an absorbent chassis in accordance with another embodiment;

FIG. 16A is a front-side perspective of an absorbent chassis as folded in accordance with the configuration shown in FIG. 15;

FIG. 16B is a back-side perspective of an absorbent chassis as folded in accordance with the configuration shown in FIG. 15;

FIG. 17 provides a high-level assembly configuration for forming a wearable absorbent article comprising a multi-piece reusable belt and an absorbent chassis;

FIG. 18A provides a high-level assembly configuration for forming a wearable absorbent article comprising a reusable belt and a disposable insert;

FIG. 18B provides an example ring belt with a permanently attached crotch piece portion;

FIG. 19A is a plain view of an inner (wearer-facing) surface of a crotch piece of a multi-piece reusable belt crotch as opened and laid flat;

FIG. 19B is a plain view of an inner (wearer-facing) surface of the crotch piece with a disposable insert attached thereto;

FIG. 20 is a cross sectional view of an example disposable insert such as shown in FIG. 19B, taken along centerline X-X' in FIG. 19B;

FIG. 21 provides a high-level assembly configuration for forming a wearable absorbent article comprising a multi-piece reusable belt and a disposable insert in accordance with another embodiment;

FIG. 22 provides a high-level assembly configuration for forming a wearable absorbent article comprising a reusable outer shell and a disposable insert in accordance with another embodiment;

FIGS. 23A-23D illustrate example sleeves on the back-side of the absorbent chassis in accordance with one or more embodiments;

FIG. 24 illustrates a block diagram of an example, non-limiting multi-piece absorbent article manufacturing system that facilitates manufacturing the multi-piece absorbent articles described with reference to FIGS. 1-23D;

FIG. 25 illustrates a block diagram of an example, non-limiting absorbent chassis formation unit;

FIG. 26 provides a high-level flow diagram of an example process for forming absorbent chassis adapted for use with reusable belts;

FIG. 27 illustrates a block diagram of an example, non-limiting reusable belt formation unit;

FIGS. 28-29 illustrates a high-level flow diagram of an example, non-limiting method for forming a wearable absorbent article in accordance with one or more embodiments.

Figure 30:
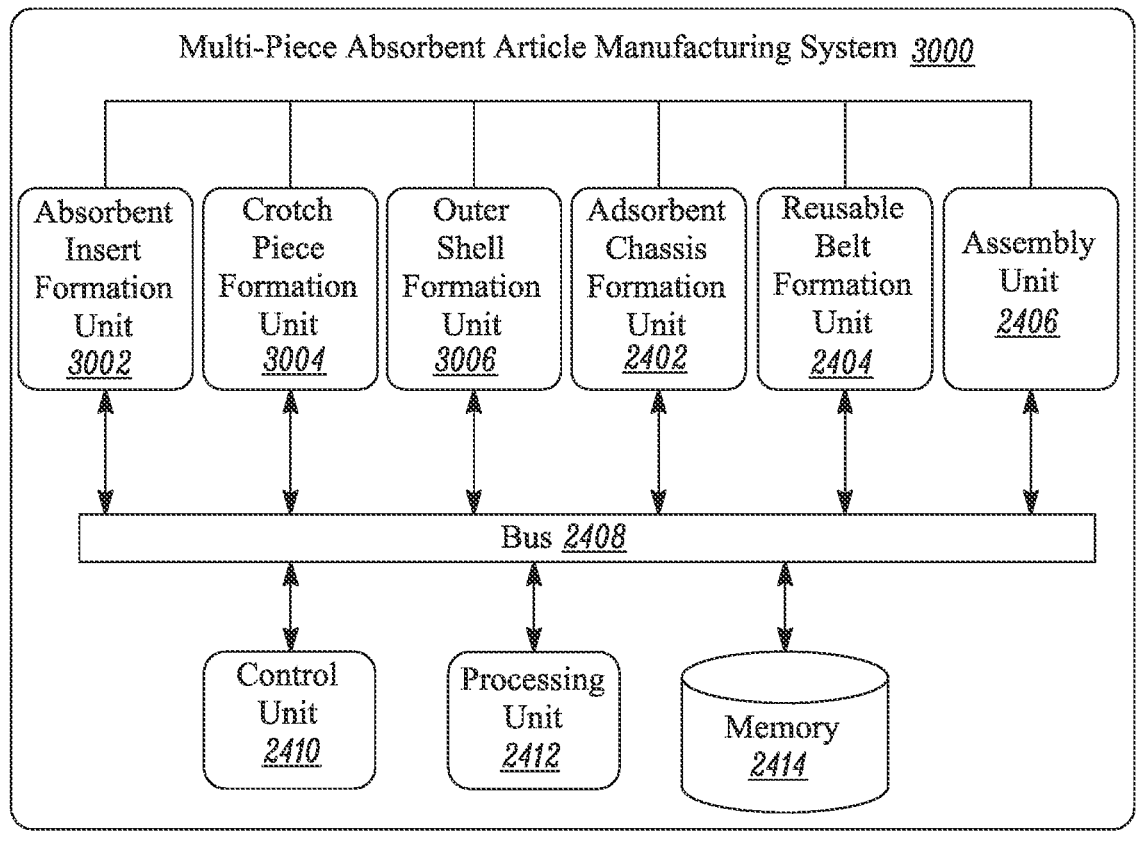
Figure 32:
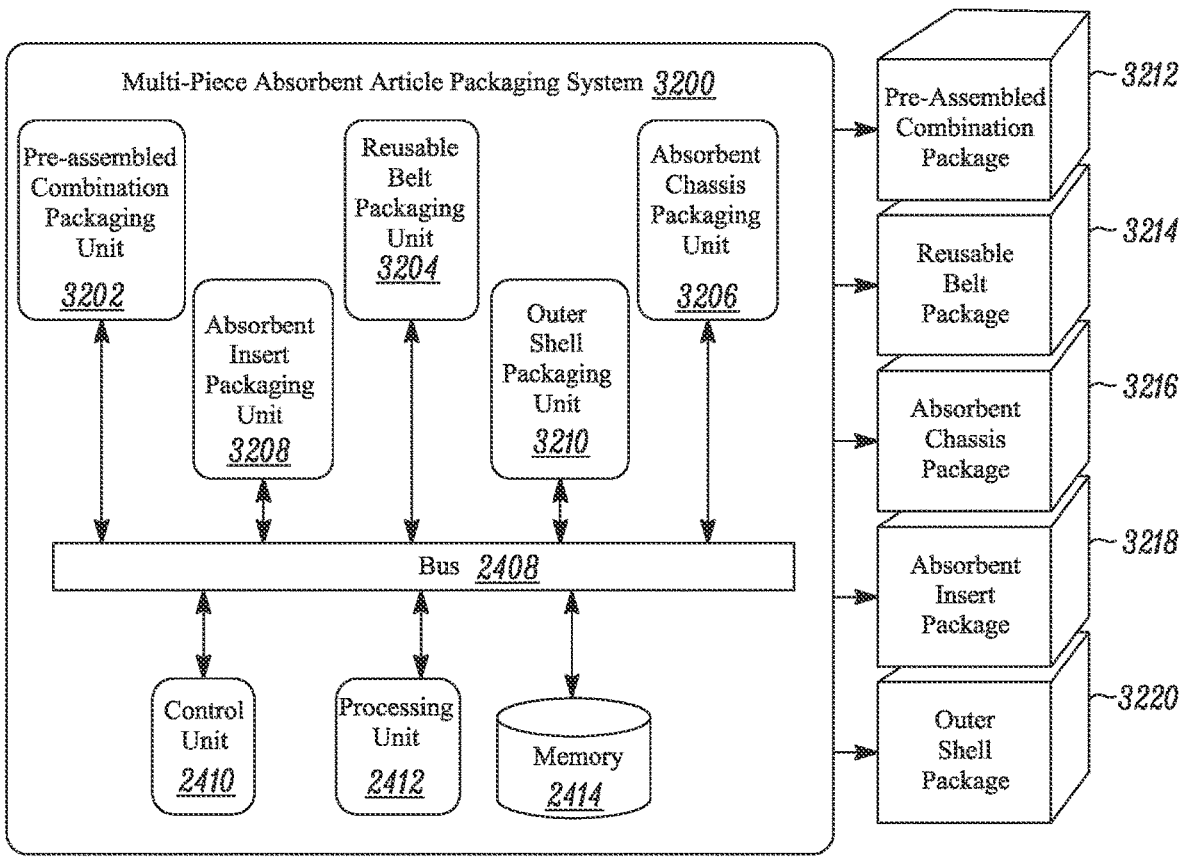

FIG. 30 illustrates a block diagram of an example, non-limiting multi-piece absorbent article manufacturing system that facilitates manufacturing the multi-piece absorbent articles described with reference to FIGS. 18A-22;

FIG. 31 illustrates a high-level flow diagram of another example method for forming a wearable absorbent article in accordance with one or more embodiments;

FIG. 32 illustrates a block diagram of an example, non-limiting multi-piece absorbent article packaging system that facilitates packaging the wearable absorbent articles described with reference to FIGS. 1-23D and their component parts in accordance with one or more embodiments of the disclosed subject matter; and FIG. 33 illustrates a high-level flow diagram of an example method for forming and packaging wearable absorbent articles in accordance with one or more embodiments.

DETAILED DESCRIPTION

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Wearable absorbent article" means an absorbent article designed to be worn about the waist and lower torso.

"Absorbent chassis" means a component of a multi-piece absorbent article that is adapted to be worn about the lower torso of a wearer (more specifically in the crotch area), is adapted to contain and/or absorb urine, feces, menses or any combination thereof, and is adapted to be removably attached to a belt to form a wearable absorbent article.

"Belt" means a component of a multi-piece wearable absorbent article that is adapted to be worn about the waist of a wearer and adapted to removably attach to an absorbent chassis to form a wearable absorbent article. A belt can include one or more pieces adapted to removably attach to one another and/or the absorbent chassis.

"Absorbent insert" and "insert" mean a component of a multi-piece absorbent article that is adapted to contain and/or absorb urine, feces, menses or any combination thereof, and is adapted to be installable and removable as a modular unit, from an outer cover to form an absorbent article. The terms "absorbent insert," and "insert" may be used interchangeably herein.

"Outer cover" means a component of a multi-piece absorbent article that is adapted to be worn about the lower torso of a wearer and is adapted to support an absorbent insert and hold the insert next to the wearer's body to form an absorbent article. Herein, a shell may also be referred to as an "outer cover". The term encompasses a wrapping structure (such as included in a conventional diaper) and a pant structure (such as included in underwear for the lower torso, of any design). The terms "outer cover", "shell" and "outer shell" are interchangeable for purposes herein.

"Disposed" refers to an element being located in a particular place or position. A feature that is disposed on a surface or side of a component may be integral with said component or may be joined to said component.

"Disposable," when referring to a component of an absorbent article (e.g., an absorbent chassis and absorbent insert), means that the disposable component is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover (e.g., they are intended to be discarded after a single use and may also be configured to be recycled, composted or otherwise disposed of in an environmentally compatible manner). By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless; and/or that cannot be effectively cleaned of exudate material through ordinary laundering, so as to be sanitary and otherwise acceptable for re-use.

"Reusable," when referring to a component of an absorbent article (e.g., a reusable belt and an outer-cover) means that the component is adapted to be used for its intended purpose after initial use without substantial destruction of any portions of the component necessary for as-new functionality. For example, a reusable belt means a belt that is adapted to permit removal from at least a first absorbent chassis and reattach with at least a second absorbent chassis without substantial destruction of any portions of the reusable belt that are necessary to provide the substantial as-new functionality with the second absorbent chassis and without the necessity of any repair or reconstruction with such chassis replacement. In another example, a reusable outer cover means an outer cover that is adapted to permit removal of at least a first insert, and replacement thereof with at least a second insert, without substantial destruction of any portions of the outer cover that are necessary to provide the substantial as-new functionality of the outer cover, and without the necessity of any repair or reconstruction following such insert replacement.

The term "launderable," as used herein means that a referenced material, component, or all of a component of a multi-piece absorbent article is configured to withstand at a large number (e.g. at least 10, in some embodiments up to 50, in other embodiments more than 50) of cycles of machine washing and machine drying, (as defined by AATCC Test Method 124-2001, with some modifications as described in U.S. patent application Ser. No. 12/687,425, the entirety of which is incorporated herein by reference), without significant degradation to the appearance or performance of the article that would render it unsuitable for its intended functionality or use. Since hand-washing and line-drying are typically less stressful on an absorbent article than machine washing and machine drying, it is expected that a material, component, or article that is machine washable and machine dryable should also be hand-washable and hand-dryable for at least as many cycles. As an example, one or more reusable belts and outer covers describe herein may be launderable.

The term "laundering resistant," as used herein means that a referenced material, or component, or all of a component of a multi-piece absorbent article is configured to withstand a small number (e.g. at least one, in some embodiments up to five, in other embodiments more than five) of cycles of machine washing and machine drying, (as defined by AATCC Test Method 124-2001, with some modifications as described in U.S. patent application Ser. No. 12/687,425, the entirety of which is incorporated herein by reference), without significant degradation to the appearance or performance of the article that would render it unsuitable for its intended functionality and/or use. As an example, one or more reusable belts and outer covers describe herein may be launderable. Laundering resistant articles generally experience degradation after fewer laundering cycles than launderable articles.

The term "durable" when referring to a material used to form a component (refers to launderable material. Some example durable materials can include but are not limited to: a woven fabric material, a knitted material, a textile material, a cotton material, a polyester material, a wool material, a bamboo material, a hemp material, a silk material, a rayon material, a polyester material, a nylon material, Lycra, Spandex, breathable waterproof materials with microscopic pores smaller than a water droplet but larger than a water vapor molecule, fabrics comprising microencapsulated phase-change polymer materials, fiber-based moisture wicking systems, and combinations thereof.

The term "semi-durable" when referring to a material refers to a laundering resistant material. Some example semi-durable materials can include but are not limited to: a fiber material, a nonwoven material, a film material, a thin-film material, a thermoplastic material, an elastic material and a non-textile material, polymeric and elastomeric films, apertured films, sponges, foams, scrims an adhesive/polymeric composition material, or combinations thereof. In various embodiments, a semi-durable material can include two or more permanently bonded layers of semi-durable and/or durable materials, wherein the two or more layers are adhesively bonded (e.g., glued), ultrasonically bonded, thermally bonded, or the like. For example, a semi-durable material can include a textile like material formed with two or more laminated layers of non-woven materials.

Suitable examples of durable and semi-durable materials that can be used for reusable components (e.g., belts, outer covers, etc.) of the disclosed multi-piece absorbent articles are described in U.S. application Ser. Nos. 12/687,493; 12/687,412; 12/687,528; and Ser. No. 12/687,425. Non-limiting examples of fibers, nonwovens and laminates of nonwovens and films that might be considered for reusable components can also be found in U.S. Pat. Nos. 7,223,818; 7,211,531; 7,060,149; 6,964,720; 6,905,987; 6,890,872; 6,884,494; 6,878,647; and 5,518,801; and U.S. Published Application Nos. 2008/0319407; 2008/0045917; 2007/0293111; 2007/0287983; 2007/0287348; 2007/0249254; 2007/0203301; and 2005/0164587.

"Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes. The process for incorporating a fiber into a substrate may be selected based upon the sorts of component materials used and the desired properties of the substrate web. The nonwoven material may comprise one or more layers of fibrous assemblies, wherein each layer may include continuous fibers, coextruded fibers, non-continuous fibers and combinations thereof.

"Joined" or "attached" means configurations whereby an element is directly secured to another element by affixing the element directly to the other element, and configurations whereby an element is indirectly secured to another element by affixing the element to intermediate member(s) that in turn are affixed to the other element.

"Removably," when referring to an element being removably joined or removably attached to another element means the respective elements can be manually detached or separated from one another without undue force. For example, an element can be removably attached to another element via a fastener component.

"A fastener component" means any component that effects removable fastening, attachment or holding of a first structure to a second structure. Fastening components may be in the form of mechanical fasteners, such as hook and loop fasteners, hook and hook fasteners, macrofasteners, microfasteners, buttons, snaps, tab and slot fasteners, tape fasteners, magnetic fasteners, hermaphroditic fasteners, posts, zippers, bands or strips, and the like. Additionally, or alternatively, fastening components may comprise adhesive and/or cohesive materials. An absorbent article may have a single fastener component, for example, an adhesive patch on the first structure adapted to adhere to one or more types of surfaces on the second structure, or a hook, or patch of hooks on the first structure, adapted to catch on one or more types of surfaces on the second structure. By way of further example, any structure such as a pocket, strap, hook, buckle, etc. on a first structure adapted to capture and retain, in whole or in part, the second structure, is a "fastener component" as used herein. An absorbent article may also comprise two or more cooperating fastener mechanisms, for example, respective parts of a hook-and-loop fastening system, respective surfaces having a cohesive material applied thereto; male and female snap fastener components, a button and button hole, slot or loop, etc. Exemplary fastener components are described in U.S. Pat. Nos. 6,936,039; 6,893,388; 6,669,618; 6,432,098; and 6,251,097, and U.S. Published Application Pub. Nos. 2005/0234419; 2005/0215971; 2005/0215970; 2005/0130821; 2007/0078427 and 2007/0093769. Any suitable combination of the foregoing are within the scope of the invention. The terms "fastener component" and "temporary fastener component" are used interchangeable unless context warrants particular distinction amongst the terms.

The term "extensible" as used herein refers to the property of a material that elongates, without substantial rupture or breakage, by at least 20% at a load of between 0.05 and 10 N/cm in the Hysteresis Test (as described herein). Micro-sized rupture or breakage of a material is not considered substantial rupture or breakage. However, macro-sized ruptures through the structure (e.g., one or more large tears such as tears greater than about 5 millimeters in any direction, or breaking into two or more pieces, or resulting in significant structural degradation which may render the material unusable for its intended purpose) are considered substantial ruptures or breakage. A material that does not meet this definition for "extensible" is considered "inextensible."

The term "elastic" as used herein refers to the property of a material that elongates, without substantial rupture or breakage, by at least 20% at a load of between 0.05 and 10 N/cm in the Hysteresis Test. Further, the elastic material has a set less than or equal to 20% of the extension as measured according to the Hysteresis Test. For example, an elastic material that has an initial length of 25 millimeters can elongate to at least 37.5 millimeters (50% elongation) and, upon removal of the force, retract to a length of 27.5 millimeters, i.e., have a set of 2.5 millimeters (20% set), when subjected to the Hysteresis Test. It is to be understood, however, that this definition of elastic does not apply to materials such as individual elastic strands that do not have the proper dimensions (e.g., not wide enough) to be properly subjected to the Hysteresis Test. Instead, such material is considered to be elastic if it can elongate by at least 50% upon application of a biasing force, and return substantially to its original length (i.e., exhibit less than 20% set) upon release of the biasing force. Elastic materials can be in the form of films, strands, nonwovens and combinations thereof.

The term "transformation" refers herein to a change or activity resulting in a change in a web, layer, article, plurality of articles, material or portions thereof with regard to the thickness, length, width, shape, relative position, texture, color, tackiness, etc. Transformations are: fiberization, core component mixing, core formation/deposition, slitting, cutting, notching, shaping, perforation, die cutting, trimming, thermal bonding, ultrasonic bonding, pressure bonding, radio frequency bonding, seaming, adhesive application, cohesive application, lotion application, folding, bi-folding, tucking, spacing, positioning, registration, activation, compression, nipping, calendaring, substrate combining, component combining, web combining, elastic tensioning, fastening element pre-fastening, product stacking, and packaging. The term "transformation mechanism" refers herein to an apparatus adapted to produce a transformation.

The term "pant" (also referred to as "training pant", "pre-closed diaper", "diaper-pant", and "pull-on diaper") refers herein to disposable absorbent articles having a continuous perimeter waist opening and at least one continuous perimeter leg openings designed for infant or adult wearers. A pant can be pre-formed by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed).

"Inboard," with respect to a first feature of an article and its position relative a second feature or location on the article, means that the first feature lies closer to a respective centerline of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal centerline, and longitudinally inboard means the first feature is closer to the lateral centerline. Conversely, "outboard," with respect to a first feature of an article and its position relative a second feature or location on the article, means that the first feature lies farther from the respective centerline of the article than the second feature or location.

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Figure 1:
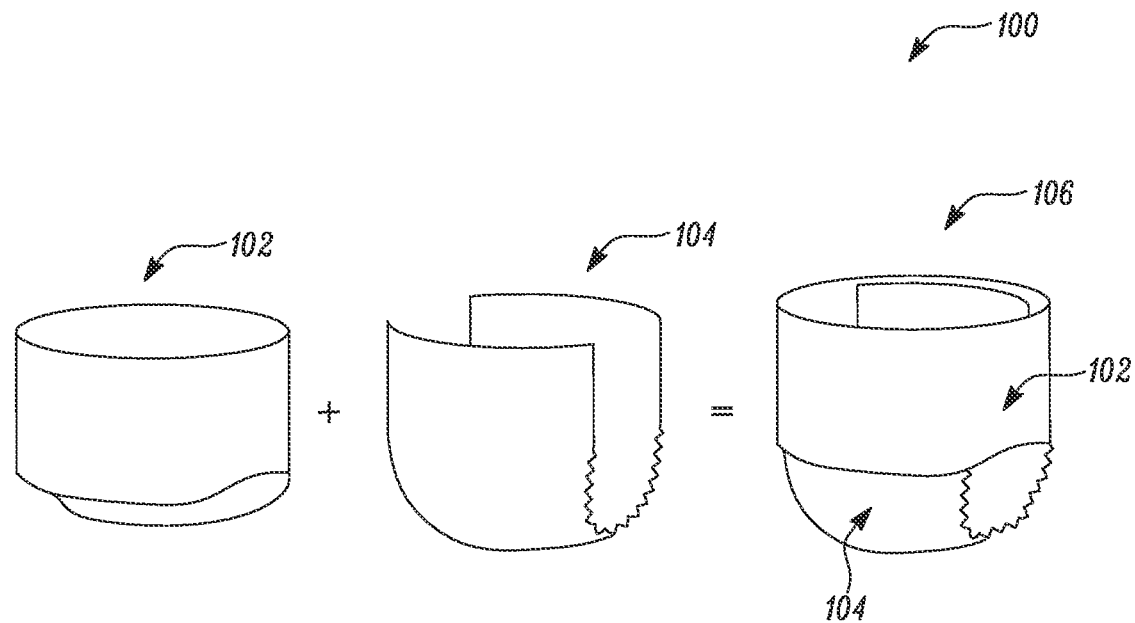
FIG. 1 provides a high-level assembly configuration for forming a wearable absorbent article comprising a continuous ring reusable belt and an absorbent chassis.
Figure 2:
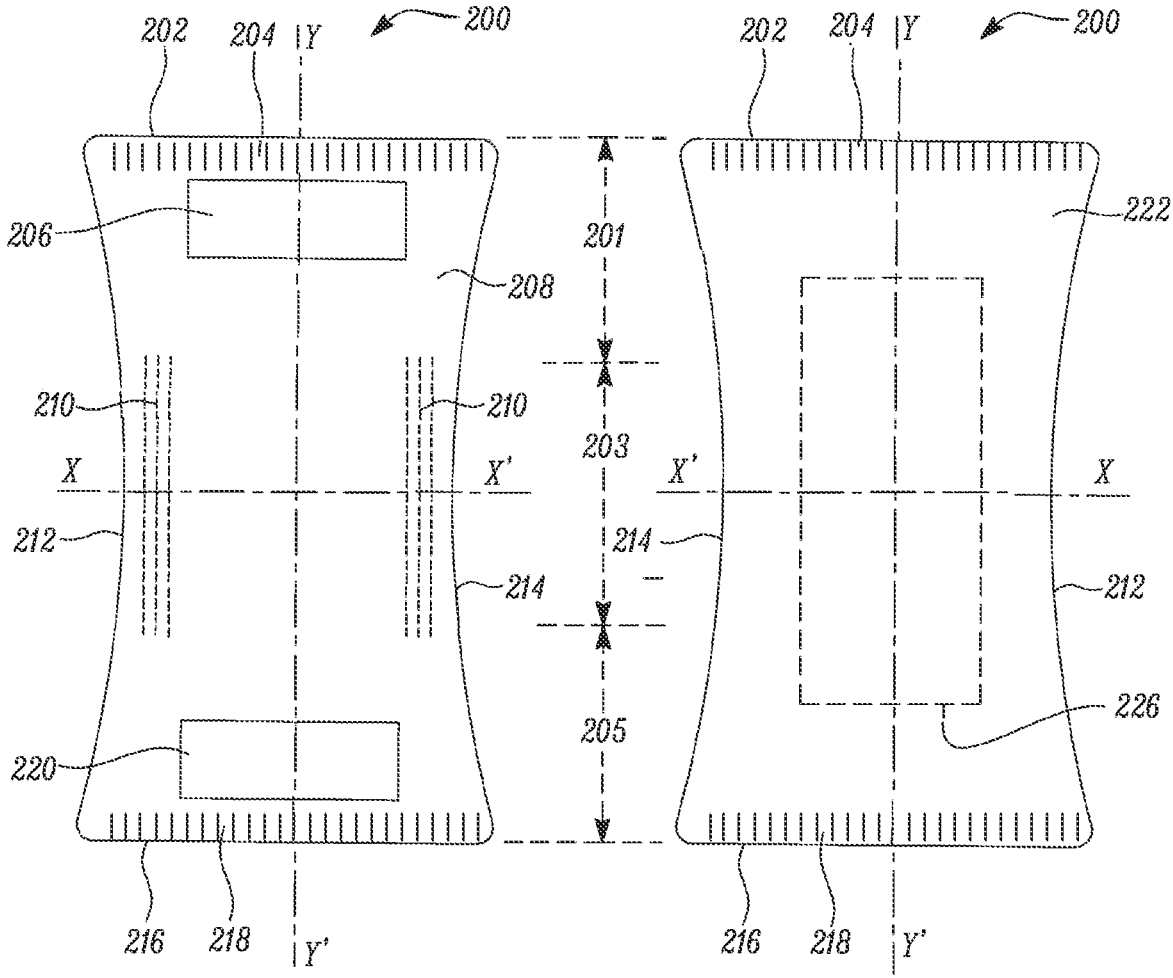
FIG. 2A is a plain view of an outer (garment-facing) surface of an absorbent chassis as opened and laid flat.
FIG. 2B is a plain view of an inner (wearer-facing) surface of an absorbent chassis as opened and laid flat.

FIG. 1 provides a high-level assembly configuration 100 for forming a wearable absorbent article 106 comprising a continuous ring belt (hereinafter ring belt 102) and an absorbent chassis 104. In various embodiments, the absorbent chassis 104 is disposable and the ring belt 102 is reusable with additional absorbent chassis corresponding to absorbent chassis 104.

As illustrated in FIG. 1, the wearable absorbent article 106 article can be assembled by wrapping the ring belt 102 around opposite lateral ends of the absorbent chassis 106 when the absorbent chassis 106 is folded as shown. The ring belt 102 can be formed with a continuous ring of one or more expandable materials and/or parts adapted to expand in association with pulling the ring belt 102 over the wearer's body (e.g., over the head and arms or over the feet and legs) and compress or tighten when positioned around (or near) the wear's waist. The absorbent chassis 104 can correspond to the absorbent chassis portion of various existing taped diapers and/or pant absorbent articles with the tape side pieces and/or permanently glued waistband removed, and some other differences as described in greater detail infra.

The wearable absorbent article 106 as assembled is adapted for wear as a pant around the lower torso of a wearer to contain and/or absorb urine, feces, menses or any combination thereof. In some embodiments, the wearable absorbent article 106 can be pre-assembled prior to wear. With these embodiments, the ring belt 102 and/or the chassis 104 can include at least one fastener component that provides for removably attaching the ring belt 102 to the chassis 106 to form the wearable absorbent article 106. After wear/soiling, the wearable absorbent article 106 can be removed from the wearer and the ring belt 102 can be detached from the absorbent chassis 104. The used/soiled absorbent chassis can be disposed and the ring belt 102 can further be re-used and reattached to one or more additional absorbent chassis corresponding to absorbent chassis 104. Additional description of the ring belt 102 and the chassis 104 in accordance with these embodiments is described below.

Additionally, or alternatively, the wearable absorbent article 106 can be assembled at the time of wear in association with positioning the chassis 104 and the ring belt 102 on the wearer. For example, the absorbent chassis 104 can first be longitudinally positioned around the lower torso of the wearer (e.g., as wrapped longitudinally from the backside of the wearer, through the legs and to the front side of the wearer) and the ring belt 102 can thereafter be positioned around the waist of the wearer and over the lateral opposing ends of the absorbent chassis 104. In some implementations of these embodiments, the ring belt 102 can hold the chassis 104 in place as positioned around the lower torso of the wearer via pressure force. For example, the ring belt 102 can be formed with an extensible material and/or an elastic material that expands to a circumference wide enough to be comfortably pulled around the body of the wearer (e.g., over the head and arms or over the feet and legs) and positioned around the waist of the wearer. The ring belt 102 can further compress to a smaller circumference once placed around the waist of the wearer and against opposite ends of the absorbent chassis 106. With this configuration, the ring belt 102 can be adapted to apply a sufficient pressure force against the wearer's waist such that the opposite ends of the chassis 102 positioned between the ring belt and the wearer's waist remain in place during wear. With these embodiments, the ring belt 102 and the chassis 104 may not include any fastener components to facilitate attachment to one another.

Figures 4A, 4B:
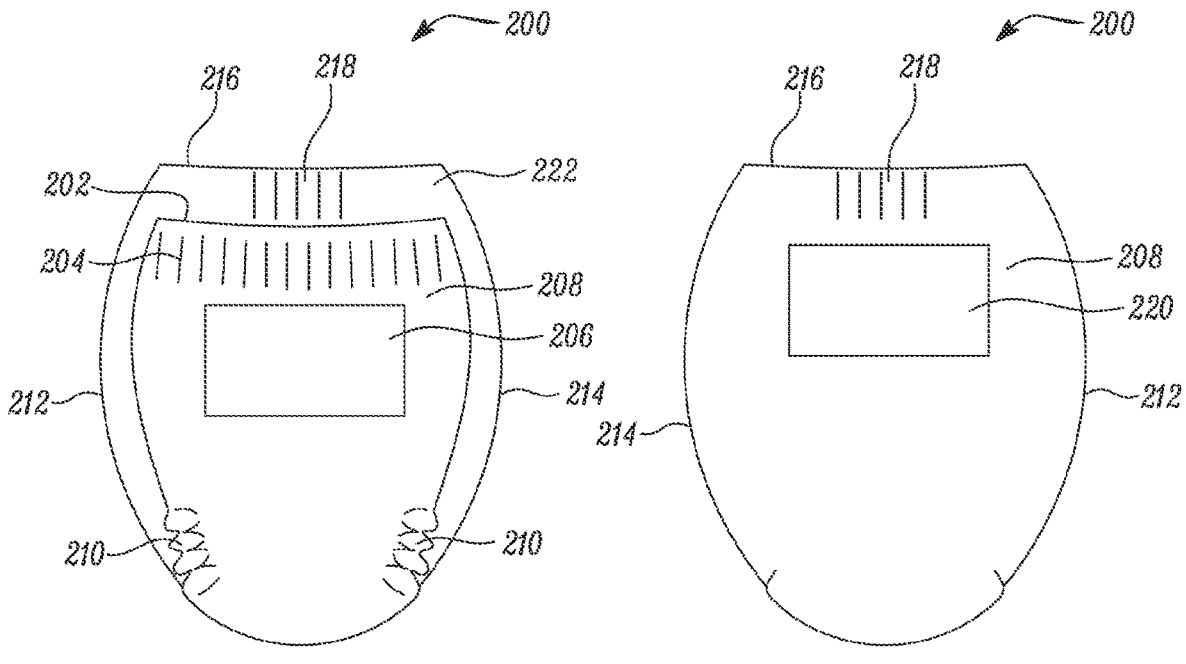
FIG. 4A is a front-side perspective of the absorbent chassis shown in FIGS. 2A-2B in a folded configuration.
FIG. 4B is a back-side perspective of the absorbent chassis shown in FIG. 2A-2B in a folded configuration.

FIG. 2A is a plain view of an outer (garment-facing) surface of an absorbent chassis 200 adapted for use with a continuous ring belt as opened and laid flat. FIG. 2B is a plain view of an inner (wearer-facing) surface of the absorbent chassis 200 as opened and laid flat. FIG. 4A is a front-side perspective of the absorbent chassis 200 shown in FIGS. 2A-2B in a folded configuration, and FIG. 4B is a back-side perspective of the absorbent chassis shown in FIG. 2A-2B in the folded configuration. In various embodiments, the absorbent chassis 104 can be or correspond to absorbent chassis 200, or vice versa.

With reference to FIGS. 1A, 1B, 4A and 4B, the absorbent chassis 200 is includes a first waist region 201, a second waist region 205, and a crotch region 203 disposed intermediate the first and second waist regions. The first waist region 201 may be configured as a front waist region, and the second waist region 205 may be configured as back waist region. In some embodiments, the length of each of the front waist region, back waist region, and crotch region may be ⅓ of the length of the absorbent chassis 200. The absorbent chassis includes laterally extending front waist end 202 and a longitudinally opposing and laterally extending back waist end 216, a; a longitudinal centerline Y-Y' and a lateral centerline X-X'.

The absorbent chassis 200 includes an inner, body facing surface 222 (as shown in FIGS. 2B and 4A), and an outer, garment facing surface 208 (as shown in FIGS. 2A, 4A and 4B). The absorbent chassis 200 may include a backsheet that forms or is otherwise located on the garment facing surface and a topsheet that forms or is otherwise located on the body facing surface. The absorbent chassis further includes an absorbent region 226 positioned within a central area of the absorbent chassis including portions of the front waist region 201, the crotch region 203 and the back waist region. The absorbent core region 226 can include an absorbent core disposed between a portion of the topsheet and the backsheet.

Figure 3:
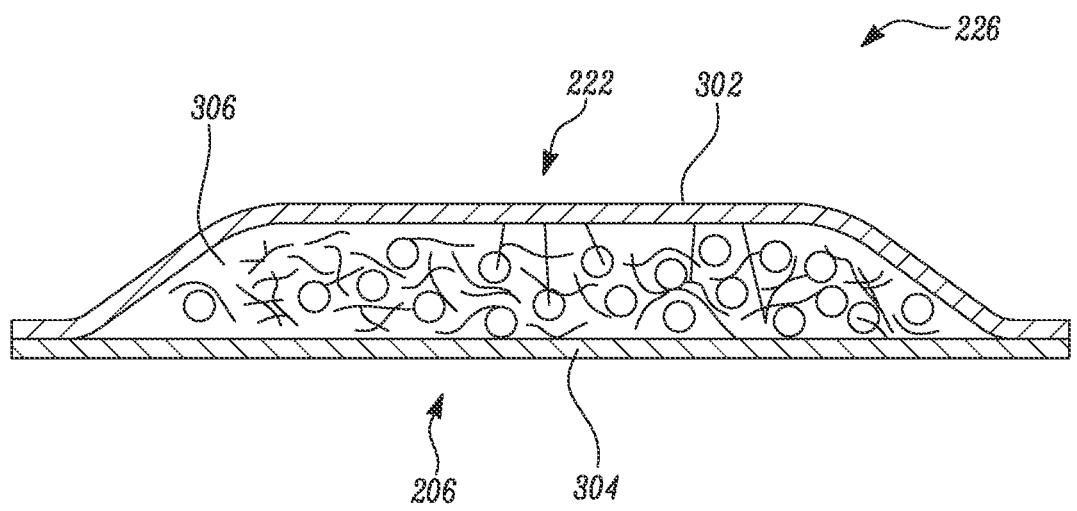
FIG. 3 is a cross sectional view of an example absorbent chassis as shown in FIG. 2B, taken along centerline X-X' in FIG. 2B.

For example, FIG. 3 is a cross-sectional view of the absorbent core region 226 taken along centerline X-X' in FIG. 2B. As illustrated in FIG. 3, the absorbent core region 226 can include an absorbent core 306 disposed between and enclosed within a topsheet 302 and a backsheet 304. In various embodiments, the topsheet may define the body facing surface 222 and the backsheet 304 may define the garment facing surface 208.

The backsheet 304 may be impervious to fluids (e.g., menses, urine, and/or runny feces) and may be manufactured from a thin plastic film, although other flexible liquid impervious materials may also be used. The backsheet 304 may prevent the exudates absorbed and contained in the absorbent core 306 from wetting articles which contact the absorbent chassis 200, such as bedsheets, pajamas and undergarments. The backsheet 304 may also comprise a woven or nonwoven material, polymeric films such as thermoplastic films of polyethylene or polypropylene, and/ or a multi-layer or composite materials comprising a film and a nonwoven material (e.g., having an inner film layer and an outer nonwoven layer). In various embodiments, the backsheet 34 is substantially water-impermeable. The backsheet may, for example, be or comprise a thin plastic film, such as a thermoplastic film having a thickness of about 0.012 mm to about 0.051 mm Other suitable backsheet 304 materials may include breathable materials that permit vapors to escape from the absorbent core while still preventing exudates from passing through the backsheet 3-4. The size of the backsheet 136 may be dictated by the size of the absorbent core 306 and/or particular configuration or size of the absorbent chassis 200.

The topsheet 302 is generally a portion of the absorbent article that may be positioned at least in partial contact or close proximity to a wearer. Suitable topsheets 302 are generally supple, soft feeling, and non-irritating to a wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet 302 may comprise one or more apertures. The topsheet may be apertured by overbonding a material and then rupturing the overbonds through ring rolling, such as disclosed in U.S. Pat. No. 5,628,097, and disclosed in U.S. Pat. Appl. Publication No. 2016/0136014. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 304, topsheet 302 or any portion thereof may be embossed and/or matte finished to provide a more clothlike appearance.

Exemplary absorbent structures for use as the absorbent core 306 of the present disclosure include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials (AGM); or any other known absorbent material or combinations of materials. In certain embodiments, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. Such a core may comprise primarily absorbent polymer material in amounts of at least about 60%, 70%, 80%, 85%, 90%, 95%, or even about 100%, where the remainder of the core comprises a microfiber glue (if applicable). Among other benefits, it is believed that when at least a portion of the absorbent core is substantially cellulose free, this portion of the absorbent core is significantly thinner and more flexible than a similar absorbent core that includes more than 10% by weight of cellulosic fibers.

With continued reference to FIGS. 2A, 2B, 4A and 4B, the periphery of the absorbent chassis 200 may be defined by the front waist end 202, the back waist end 216, the left side edge 212 and the right side edge 214. Both side the left side edge 212 and the right side edge 214 extend longitudinally between the front waist end 202 and the back waist end 216. When absorbent chassis 200 is worn on the lower torso of a wearer, the front waist end 202 and the back waist end 216 may partially fit about a portion of the waist of the wearer. At the same time, the left side edge 212 and the right side edge 214 may encircle at least a portion of the legs of the wearer, and the crotch region 203 may be generally positioned between the legs of the wearer with the absorbent core region 226 extending from the front waist region 201 through the crotch region 203 to the back waist region 205. In some embodiments, the front waist region 201 can be identical to the back waist region 205, allowing for positioning on the wearer back to front or front to back.

In some embodiments, a portion or the whole of the absorbent chassis 200 may be made laterally extensible. The additional extensibility may help allow the absorbent chassis to conform to the body of a wearer during movement by the wearer. The additional extensibility may also help, for example, allow the user to extend the front waist region 201, the back waist region 203, or both, to provide additional body coverage for wearers of differing size, i.e., to tailor the diaper to an individual wearer. Such extension of the waist region or regions may give the absorbent chassis 200 a generally hourglass shape, so long as the crotch region is extended to a relatively lesser degree than the waist region or regions, and may impart a tailored appearance to the article when it is worn.

The absorbent chassis 200 may also include elasticized leg cuffs 210, an elasticized front waistband 204 and/or an elasticized back waistband 218. It is to be appreciated that the elasticized leg cuffs 210 can be and are sometimes also referred to as leg bands, side flaps, barrier cuffs, elastic cuffs or gasketing cuffs. The elasticized leg cuffs 210 may be configured in various ways to help reduce the leakage of body exudates in the leg regions. Example the elasticized leg cuffs 210 may include those described in U.S. patent application Ser. No. 17/173,453.

The elasticized front waistband 204 and the elasticized back waistband 218 may provide improved fit and containment and may be that portion or zone of the absorbent chassis 200 that may elastically expand and contract to dynamically fit a wearer's waist. The elasticized front waistband 204 and the elasticized back waistband 218 may extend longitudinally inwardly from the respective waist ends 202, 216. The elasticized front waistband 204 and the elasticized back waistband 218 may be constructed in a number of different configurations including those described in U.S. Pat. Nos. 4,515,595 and 5,151,092.

The elasticized front waistband 204 and the elasticized back waistband 218 may include materials that have been "prestrained" or "mechanically prestrained" (i.e. subjected to some degree of localized pattern mechanical stretching to permanently elongate the material). In some embodiments, the materials may be prestrained by directing the material through an incremental mechanical stretching system as described in U.S. Pat. No. 5,330,458.

In one or more embodiments, the absorbent chassis 200 can be combined with a continuous ring belt (e.g., ring belt 102) to form a wearable absorbent article (e.g., wearable absorbent article 106) as described with reference to FIG. 1. In this regard, with reference to FIGS. 1, 2A, 2B, 4A and 4B and the understanding that the absorbent chassis 200 can be or correspond to absorbent chassis 104, the absorbent chassis 200 can be adapted to form a wearable absorbent article 106 when the ring belt 102 is wrapped around the front waist end 202 and the back waist end 216 when the absorbent chassis 200 is worn or in a folded configuration, thereby connecting the front waist end 202 and the back waist end 216 to form a closed waist circumference and leg openings. As assembled with the absorbent chassis 200, the ring belt 102 may contact the garment facing surface 208 and cover the whole or a portion of the front waist region 201 and cover the whole or a portion of the back waist region 205. It is also contemplated that at least a portion of the belt may contact the wearer-facing surface of the chassis. For example, the belt may be formed to attach to the wearer-facing surface. In other embodiments, the belt may be split such that a portion of the belt contacts the garment-facing surface and another portion contacts the wearer-facing surface.

As previously mentioned, in some embodiments the absorbent chassis 200 can be held in place on the body of the wearer via pressure force applied by the ring belt 102 when pressed against the front waist region 201 and the back waist region 205 as disposed between the ring belt 102 and the wearer's body. With these embodiments, the ring belt 102 can be formed with an elastic material and/or one or more extensible components adapted to apply the pressure force when worn. Additional description of the ring belt in accordance with this configuration is described infra.

Additionally, or alternatively, the absorbent chassis 200 and/or the ring belt 102 can include various configurations of fastening components that provide for attaching the ring belt 102 to the absorbent chassis 200 and, if applicable, fastening of the front waist region 201 and the back waist region 205 together to form a closed waist circumference and leg openings. These fastening components can be adapted to releasably and/or refastenably engage or connect with one or more portions of the ring belt 102. For example, as shown in FIGS. 2A, 4A and 4B, the absorbent chassis 200 may include a first fastening component 206 disposed on the garment facing surface 208 within the front waist region 201 and a second fastening component 220 disposed on the garment facing surface 208 within the back waist region 205. In some embodiments, the first fastening component 206 and/or the second fastening component 220 may correspond to indicia to assist with attachment of a belt to the absorbent chassis 200 and positioning around the waist. Indicia may include text, shapes and/or color. In nonlimiting embodiments, indicia comprises a colored adhesive. In this way, the wearer or caregiver could determine where to secure the belt based on the location of the color ensuring the entire fastening component is covered.

Additionally, or alternatively, the first fastening component 206 and/or the second fastening component 220 may correspond to mechanical fastener components. The first fastening component 206 and/or the second fastening component 220 may include the same type of fastener or different types of fasteners. The first fastening component 206 and the second fastening component 220 may form a portion of or may be permanently bonded, adhered or otherwise joined directly or indirectly to the wearer-facing surface and/or garment-facing surface 208. The fastening components may also be permanently bonded or attached to the absorbent chassis 200 in various ways, such as for example, by adhesive bonds, sonic bonds, pressure bonds, thermal bonds or combinations thereof.

Figure 4C:
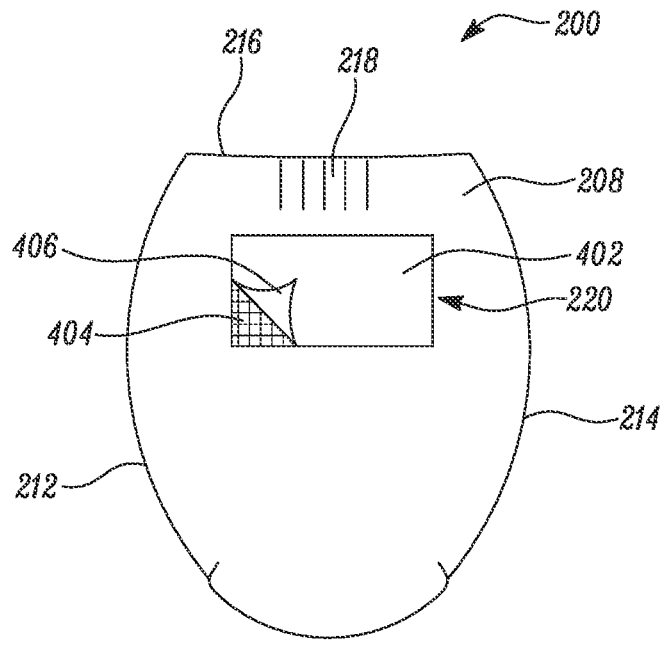
FIG. 4C is a back-side perspective of the absorbent chassis shown in FIGS. 2A-2B in a folded configuration with a temporary adhesive fastener component in accordance with an embodiment.

In some embodiments, the first fastening component 206 and/or the second fastening component 220 may include an adhesive patch. With these embodiments, the adhesive patch 402 can include an adhesive layer 404 and a protective layer 406 joined thereto that can be peeled off to expose the adhesive layer, as shown in FIG. 4C. In this regard, FIG. 4C is a back-side perspective of the absorbent chassis 200 shown in FIGS. 2A-2B in a folded configuration with an adhesive patch 402 for the second fastening component 220. In various embodiments, a same or similar adhesive patch 402 can be used for the first fastening component 206. In some implementations, the adhesive layer 404 and/or a portion of the adhesive layer can further be adapted to remain on the absorbent chassis 200 when the ring belt 102 is removed therefrom. This can be accomplished by surface treatment to the material of the outer (garment-facing) surface of the absorbent chassis 200 to make the adhesive layer 404 cling to the material of the outer surface material (i.e., surface treatments on a nonwoven, additives when forming the nonwoven). This can also be accomplished by using a single layer of polymer film material under the adhesive layer on the absorbent chassis 200.

In this regard, the glue used for the adhesive layer 404 may include a glue that provides for forming a semi-permanent bond, such as a glue that does not crystalize. Preferably, the adhesive layer 404 can include a pressure-sensitive hotmelt glue, such as Ecomelt H145 from Collano, Switzerland, although other commercially available pressure-sensitive adhesives can be used, including adhesives that are pressure-sensitive in a cold state, such as acrylate glue, these adhesives normally being combined with a stickiness-enhancing agent, such as terpense resin, or hot-melt glue such as styrene or butadiene co-polymers. The protective layer 406 may conveniently comprise silicone-coated paper, so-called release paper, although other material that has poor adhesion to the glue used may be employed, e.g., foam material that has a surface which presents a small contact surface area. A silicone-treated protective paper normally used in this respect is ESP 48 marketed by Lohjan Paperi OY, Finland.

FIGS. 5A-5I are depictions of various example ring belts in accordance with different embodiments. The respective ring belts shown in FIGS. 5A-5I may correspond to ring belt 102 (or vice versa). Repetitive description of like elements presented in different embodiments is omitted for sake of brevity. While the description below is in terms of a ring belt, it is applicable to outer covers as well.

Ring belts and outer covers disclosed herein may be reusable and may be formed with one or more durable and/or semi-durable materials. In this regard, all of the belts and outer covers disclosed herein may be launderable or laundering resistant. Each of the ring belts disclosed herein may also be expandable and/or capable of expanding (to fit over the body) and constricting (to tighten around the wearers waist). For example, the respective ring belts can be formed with one or more elastic and/or elastomeric materials and/or include expandable and contractable mechanical elements.

In some embodiments, a ring belt can be formed with a two or more bonded layers of durable and/or semi-durable material. Forming the component with more than one layer may provide various benefits. A second layer (and any additional layers) may provide supplemental tensile strength in both the lateral and longitudinal directions across said component. Additionally, a first layer may be selected for a first set of properties, and a second layer may be selected for a second set of properties. For example, material forming a first layer may be selected for having comparatively greater elasticity and a particular texture, color and/or other appearance-related properties, and material forming a second layer may be selected for having comparatively different hydrophobicity and/or softness to the skin for purposes of an inner layer that contacts the wear's skin, the two layers in combination imparting a combination of desirable attributes.

In addition, a belt may be formed with a single layer of differing materials, for example, differing materials in the respective front, back and/or side regions. For example, the material predominately forming the side regions may be selected primarily for its elasticity features, which may better serve to provide snug fit about wearer body contours and accommodate wearer movement (i.e., about the hips). By comparison, the material predominately forming the front and back regions of the ring belt might be selected primarily for accommodating one or more fastener components to facilitate attaching the ring belt to the absorbent chassis. In particular, the side parts may be formed with an elastic material comprising two or more layers of laminated thermoplastic materials, including for example film or elastic strands, and the front and back parts may be formed with a non-elastic or semi-elastic material such as nonwovens. Other durable and semi-durable materials described herein can be used for various parts. The parts (i.e., front part, the back part and the side parts) can be permanently attached to one another to form a continuous ring of inseparable materials. The mechanism of attachment of the respective parts can vary (e.g., adhesively bonded/glued, sewn, thermally bonded, ultrasonically bonded, etc.).

Layers or other elements of the ring belts (and other belts and outer covers) disclosed herein may be joined to each other via any suitable mechanism, including, for example, adhesives, cohesives, mechanical bonding, mechanical entanglement (for example through use of molten polymerics materials that bond once cooled), ultrasonic bonding, sewing, stitching, serging, edging, and combinations thereof.

With reference to FIG. 5A, an example ring belt 501 is formed as a continuous ring of the same piece of material. The same piece of material may include a laminate of materials; the laminate layers may be the same or may differ. For example, the ring belt 502 includes an inner surface 502 that may correspond to a wearer facing surface and adapted to contact the wearers skin. In some implementations, the material of the inner surface 502 can include a material selected for softness and texture that provides comfort when contacting the wearer's skin. The ring belt further includes an outer surface 504 that corresponds to a garment-facing surface. In various embodiments, the outer surface 504 and/or an entirety of the ring belt 501 is formed with one or more layers of an elastic material. In one implementation, the ring belt 502 may comprise an elastic material formed between two nonwoven layers of material as the inner and outer surfaces. Where the ring belt comprises a continuous piece of material, it is contemplated that the entire inner and/or the entire outer surface may serve as a fastening component capable of engaging with a portion of the absorbent chassis.

FIG. 5B presents another example ring belt 503. Ring belt 503 can include same or similar elements and materials as ring belt 501, except one or more sections of the belt comprise fastener components to facilitate removably attaching the ring belt to an absorbent chassis. In the example shown, the fastener components include a first fastener component 506 located on a backside of the inner surface 502 and a second fastener component 508 on the frontside of the inner surface. These fastener components may be adapted to removably or releasably attach to the front and back waist regions of the absorbent chassis.

The ring belt 503 may include one of the first fastener component 506 or the second fastener component 508, but not both.

In some embodiments, the first fastener component 506 and/or the second fastener component 508 may comprise a transferable fastener component capable of transferring to the absorbent chassis after detachment of the reusable belt from the absorbent chassis. For example, the fastener component 506 and/or the second fastener component 508 may comprise a transferable adhesive such as a hotmelt adhesive. In some implementations of these embodiments, a corresponding attachment area of the absorbent chassis (e.g., on the front and/or back waist regions) may be surface treated to attract the transferable fastener component. The corresponding attachment area may also be formed with a material adapted to attract the transferable fastener component, such as a polymer film.

FIG. 5C presents another example ring belt 505 wherein the belt is formed form different materials. Ring belt 503 can include same or similar elements and materials as ring belt 501 with integration of front and back parts (front part 512 and back part 510) into the ring belt 505 being connected by respective side parts 514. With this embodiment, the side parts 514 may be formed with a first material (e.g., an elastic laminate) and the front and back parts may be formed with a second material having different properties relative to the first material (e.g., a nonwoven material). The first and second materials may differ by material type (e.g., film, nonwoven), basis weight, elasticity, layer confirmation (e.g., laminates with different layer configurations) and combinations thereof.

FIG. 5D presents another example ring belt 507. Ring belt 507 can include same or similar elements and materials as ring belt 505 with the addition of the first fastener component 506 to the back part 510 and the second fastener component 508 to the front part. Repetitive description of like elements is omitted for sake of brevity.

FIG. 5E presents another example ring belt 509. Ring belt 509 can include same or similar elements and materials as ring belt 505 with the addition of constriction flaps (back constriction flaps 516 and front constriction flaps 518) to the back part 510 and the front part 512 of the ring belt 509. In accordance with this embodiment, the side parts 514 of the ring belt 509 can be formed with a flexible, fabric or fabric like material (e.g., a non-woven fabric like material) adapted to fold onto itself and shrink in length to accommodate the circumference of the wearer's waist. The constriction flaps can further be adapted to fold onto the side parts 514 and removably attach to the material of the side parts 514 (e.g., via adhesion, cohesion, via a hook-and-loop fastening mechanism) to maintain the constricted state of the side parts 514 when the ring belt is worn. In this regard, the constriction flaps provide a mechanical mechanism to constrict and tighten the ring belt and secure the ring belt in a constricted state around the wearer's waist and front and back waist regions of the absorbent chassis when worn. The constriction flaps can further be released from the side parts 514 to increase the circumference of the ring belt 509 to facilitate placement on and removal from the wearer's body.

In the embodiment shown, the constriction flaps are released/opened. Constriction flaps can also be used to cover a fastener component prior to use. Additionally, or alternatively, the belt may include on or more fastener components on the construction flaps and/or side parts as shown in FIGS. 5F-5I.

Figure 5I:
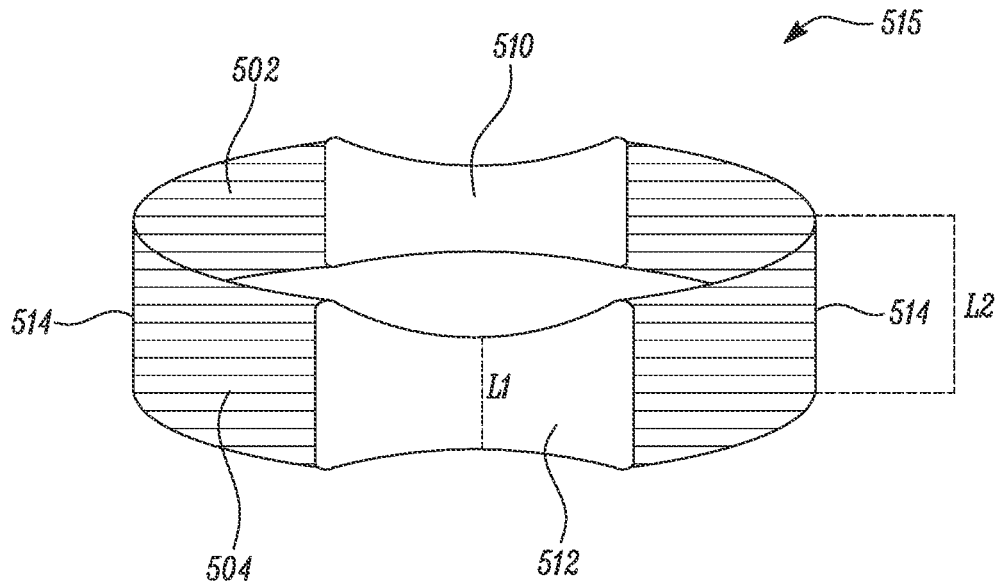

A ring belt (and other belts described herein) may comprise a nonuniform length and/or a nonuniform width. Stated different, the length and/or width of the ring belt may vary. For example, FIG. 5I presents another example ring belt 515 with front and back portions (i.e., front portion 512 and back portion 510) that have a central portion with a smaller longitudinal length L1 relative to the longitudinal length L2 of the side portions 514. Such configuration may permit more comfort during wearing, and in some instances avoid overlap with the wearer's navel, allow for easier bending by the wear and/or permit more targeted fastening. The larger side portions 514 may provide ample coverage of the hips during wear. One or more additional layers may be provided, for example to the side portions, to provide additional support maintaining the structure of the ring belt and/or softness.

FIG. 6 presents another example ring belt 600. Ring belt 600 may include same or similar elements, materials and features of the ring belts discussed above with the addition of split front and back portions. In this regard, ring belt 600 is formed as a partially continuous ring of one or more materials and includes an inner surface 602 that corresponds to a wearer facing surface and an outer surface 604 that corresponds to a garment-facing surface. Ring belt 600 further includes side portions 606 adapted for wear on opposite sides of the wearer's waist/hips, a first waist region 605 adapted for wear about the wearer's belly and/or back, and second waist region 607 adapted for wear on the wearer's back and/or belly (i.e., the opposite side of the body relative to the side of the about which the first waist region 605 is worn). The first waist region 605 is adapted to removably attach to a first waist region of an absorbent chassis (e.g., first waist region 201 of absorbent chassis 200 or the like) and the second waist region 607 is adapted to removably attach to a second waist region of the absorbent chassis (e.g., second waist region 205 of absorbent chassis 200 or the like). The first waist region 605 and the second waist region 607 may be substantially identical to one another and thus adapted to be worn front to back or back to front. Repetitive description of like elements of the first waist region 605 and the second waist region 607 is omitted for sake of brevity.

The first waist region 605 and the second waist region 607 of ring belt 600 are respectively divided into an upper part 601 and a lower part 603, wherein the upper part 601 and the lower part 603 are physical split apart from one another. The upper part 601 forms a continuous ring with the side portions 606 while the lower part 603 includes two opposing straps 610, wherein opposite ends of the straps 610 are disconnected.

FIG. 7 depicts the first waist region 605 of the ring belt 600 as positioned relative to the frontside of an absorbent chassis 700 in the manner in which the ring belt 600 is adapted to be worn with the absorbent chassis 700. As shown in FIG. 7, the upper part 601 is adapted to be worn under the absorbent chassis 700 while the straps 610 are designed to be worn over the absorbent chassis. Although not shown, it should be appreciated that the second waist region 607 of the ring belt may attach to the backside of the absorbent chassis 700 in the same configuration shown for the frontside. The absorbent chassis 700 may include same or similar features and materials as absorbent chassis 200 with some optional variations. For example, in some embodiments, one or more of the fastener components (e.g., fastener component 206 and/or fastener component 220) of the absorbent chassis 200 may be removed from absorbent chassis 700 and/or positioned in alternate locations to facilitate attachment of the absorbent chassis 700 to the ring belt 600 (or vice versa). Additional modifications are noted below.

With reference to FIGS. 2A, 2B, 6 and 7, the inner surface 602 of the upper part 601 is adapted for wear against the wearer's body, while the outer surface 604 of the upper part 601 is adapted to removably attach to an inner, wearer facing surface of an upper portion of either the front or back waist regions of the absorbent chassis 700. As shown in FIG. 6, the outer surface 604 of the upper part 601 may include one or more fastener components 608 that provide for removably attaching to the wearer facing surface of upper portions of the front and back waist regions of the absorbent chassis 700. Additionally, or alternatively, the inner surface of the upper portions of the front and/or back waist regions of the absorbent chassis 700 may include fastener components that provide for removably attaching them to the upper part 601 of the ring belt. The fastener components 608 are depicted with grey fill where the outer surface 604 is visible from the perspective of the drawing and dashed lines where the outer surface 604 is not visible. The type of the fastener components 608 can vary and include one or more of the fastener component types disclosed herein (e.g., adhesive patch fasteners, hook fasteners, etc.).

The opposing straps 610 of the lower part 603 may comprise an elastic material adapted to stretch over the garment-facing surface of the absorbent chassis 700 (in the direction indicated by the opposing arrows) and provide for tightening the ring belt 600 about the wearer's waist. The opposing ends of the opposing straps 610 may also include fastener components 612 adapted to removably attach to one another and/or the outer surface of the absorbent chassis. The type of the fastener components 612 can vary and include one or more of the fastener component types disclosed herein (e.g., adhesive patch fasteners, hook fasteners, etc.). For example, in some implementations, the fastener components 612 may include paired male/female fastener components adapted to removably attach to one another. In other implementations, the attachment components 612 may be formed on the inner surface 602 of the straps 610 and adapted to removably attach to the outer surface of the absorbent chassis 700. Additionally, or alternatively, the absorbent chassis 700 may include fastener components (e.g., formed on a lower half of the front and/or back waist regions of the outer, garment-facing surface thereof) via which the straps may be attached to the absorbent chassis 700. The wearer-facing surface and/or the garment-facing surface of the front and back waist regions of the absorbent chassis 700 may further include indica printed thereon to indicate where and how to position the upper part 601 and the lower part 603 of the respective waist regions of the ring belt 600 relative thereto.

The ring belt 600 may be assembled on a wearer by positioning the belt around the wearer's waist with first waist region adjacent 605 to the wearer's belly (or back), and the second waist region 607 adjacent to the wearer's back (or belly). The absorbent chassis 700 may thereafter be wrapped through the wearer's legs and the front and back waist regions of the absorbent chassis 700 may respectively be attached to the respective upper parts 601 via the fastener components 608, thereby connecting the absorbent chassis to the ring belt 600. Thereafter, the opposing straps 610 may be stretched or pulled toward one another and attached to one another (e.g., in a belt-buckle manner), or attached to the outer surface of the absorbent chassis, thereby tightening the ring belt 600 around the wearer's waist and the absorbent chassis 700. This configuration eases the assembly process for attaching to the absorbent chassis 700 to the ring belt 600 on the wearer and provides for changing the absorbent chassis 700 while keeping the ring belt 600 on the wearer's body. This configuration further provides for increasing the amount of surface area of the absorbent chassis 600 that contacts the wearer's body while maintaining a sufficient belt width to provide for sufficient attachment, fit and comfort. The longitudinal length L3 of the ring belt 600 may further be increased to a wider/longer length relative to other ring belts disclosed herein to accommodate both the upper part 601 and the lower part 603.

Various modifications to ring belt 600 are further envisioned. In some embodiments, the upper part 601 of the first waist region 605 and/or the second waist region 607 may be split to facilitate assembly on the wearer. With these embodiments, the split upper part 601 may include an attachment mechanism for reconnecting the split ends of the upper part to one another prior to attaching the absorbent chassis thereto, and/or for attaching the split ends of the upper part 601 to upper waist region of the absorbent chassis on the wearer facing surface thereof.

FIGS. 8A-8D provide images of an example apparatus 800 that facilitates attaching a ring belt to an absorbent chassis prior to wear to form a wearable absorbent article. In the embodiment shown, the ring belt 812 is formed with a continuous piece of material having the form of ring belt 501 shown in FIG. 5A. However, the ring belt 812 may correspond to any of the continuous ring belts discussed above and combinations thereof. The absorbent chassis 808 can likewise correspond to any of the absorbent chassis discussed above.

Image 801 depict the apparatus 800 alone, image 803 depicts the apparatus holding the absorbent chassis 808, image 805 provides a top-down perspective of the apparatus 800 holding the absorbent chassis 808 and further holding the ring belt 812 from a top-down perspective, and image 807 depicts the apparatus 800 holding the absorbent chassis 808 and the ring belt 812 from a front view perspective.

The apparatus 800 includes a chassis holder 802 with an opening or slot 804 adapted to receive and hold an absorbent chassis 808 in a folded configuration such as the folded configuration shown in FIGS. 4A-4B. The apparatus 800 further includes opposing arms 806 located on opposite sides of the chassis holder 802 that extend vertically from the chassis holder 802. The opposing arms 806 are adapted to receive and hold the ring belt 812 and position the ring belt around the front and back waist regions of the absorbent chassis 808 as shown. The opposing arms have a shape and configuration that provides for opening and separating front and back regions of the ring belt 812 such that when the ring belt 812 and is positioned around the absorbent chassis 808 as held within the chassis holder 802, the inner surfaces of the ring belt 812 do not contact or touch the absorbent chassis 808, as shown in image 805. To facilitate this end, the opposing arms 806 are separated a defined distance S from one another on opposite sides of the chassis holder 802 (as shown in image 801) and have a cylindrical shape with a defined diameter D. The distance S and the diameter D can be selected to open the ring belt 802 and separate opposing inner surfaces thereof from one another and the absorbent chassis 808 when positioned within the chassis holder as shown in image 805.

In accordance with this embodiment, the absorbent chassis 808 includes fastener components in the form of adhesive patches on the garment facing surface in the front and/or back waist regions of the absorbent chassis. Image 803 depicts the adhesive patch on the one waist region of the absorbent chassis 808 with a liner 810 or protective layer formed thereon. It should be appreciated that the opposite side of the absorbent chassis 808 can include the same adhesive patch and liner.

With this implementation, the liner 810 can be removed to reveal the adhesive layer underneath when the absorbent chassis 808 is held in the chassis holder 802. The ring belt 812 can further become attached to the opposing adhesive layers by pressing (e.g., either manually or mechanically via a machine) the inner surfaces of the ring belt 812 against the exposed adhesive layers when positioned adjacent to the adhesive layers as shown in images 805 and 807. Any other suitable form of fastening components may be utilized. Once attached, the combined ring belt 812 and absorbent chassis 808 can become a wearable absorbent article.

In various embodiments, a belt may be formed with multiple pieces. FIG. 9 provides a high-level assembly configuration 900 for forming a wearable absorbent article 906 comprising a two side-piece belt (hereinafter side-piece belt 902) and an absorbent chassis 904. In various embodiments, the absorbent chassis 904 is disposable and the side-piece belt 902 is reusable with additional absorbent chassis corresponding to absorbent chassis 904.

As illustrated in FIG. 9, the side-piece belt 902 comprises first side piece 902$_1$ and second side piece 902$_2$. The wearable absorbent article 906 article can be assembled by attaching the respective side pieces to the opposite ends of the absorbent chassis 904 as shown. For example, in some implementations, the absorbent chassis 904 can include fastener components formed on the front and back waist regions thereof to which the side pieces are adapted to attach to, thereby connecting the front and back waist regions to form the wearable absorbent article 906. Additionally, or alternatively, the respective side pieces can include fastener components on opposite longitudinal ends thereof adapted to attach to the front and back waist regions of the absorbent chassis 904. In either of these embodiments, the side pieces may be adapted to removably and/or releasably attach to the absorbent chassis 904 and be re-attached to and reused with one or more additional absorbent chassis. In some implementations, the respective side pieces can be identical to one another.

In other implementations, the respective side pieces can be mirror images of one another, with one being adapted to attach to the absorbent chassis on the left side of the wearer's waist and the other being adapted to attach to the right side. The respective side pieces 902$_1$ and 902$_2$ may be formed with one or more of the durable and/or semi-durable materials discussed herein. In this regard, the respective side pieces 902$_1$ and 902$_2$ may be launderable and/or laundering resistant.

FIG. 10 is a view of a garment-facing surface of an absorbent chassis 1000 adapted for use with a side-piece belt. In some embodiments, absorbent chassis 1000 can be or correspond to absorbent chassis 904, or vice versa. FIG. 10 depicts the absorbent chassis 1000 as opened and laid flat. FIG. 11A is a front-side perspective of the absorbent chassis 1000 shown in FIG. 10 in a folded configuration, and FIG. 11B is a back-side perspective of the absorbent chassis shown in FIG. 10 in the folded configuration. Absorbent chassis 1000 can include same or similar elements and form factors as absorbent chassis 200 (and other absorbent chassis disclosed herein) with some differences noted below tailored for use with a side-piece belt. Repetitive description of like elements employed in respective embodiments is omitted for sake of brevity.

With reference to FIGS. 2A, 10, 11A and 11B, the absorbent chassis 1000 is substantially similar to absorbent chassis 200 with the exception of the first fastener component 206 and the second fastener component 220. In this regard, the garment-facing surface 208 of absorbent chassis 1000 alternatively may include first attachment regions formed on opposite lateral sides of the front waist region 201, respectively identified as first attachment region 1002$_1$ and first attachment region 1002$_2$. The garment-facing surface 208 may also include second attachment regions formed on opposite lateral sides of the back waist region 205, respectively identified as second attachment region 1004$_2$ and second attachment region 1004$_2$.

The first attachment regions 1002$_1$ and 1002$_2$ and/or the second attachment regions 1004$_1$ and 1004$_2$ may include any of the types of fastener components disclosed herein.

Additionally, or alternatively, the first attachment regions 1002$_1$ and 1002$_2$ and/or the second attachment regions 1004$_1$ and 1004$_2$ may include indica printed on the garment-facing surface 208 of the absorbent chassis 100 that indicates where to position and attach the respective longitudinal ends of the side pieces. In some implementations of these embodiments, the indica can mark different positions for placement of the side pieces corresponding to different size fittings for the wearable absorbent article.

FIG. 12A is a view of example side pieces of a two-piece reusable belt. The side pieces are respectively identified as first side piece 1200$_1$ and second side piece 1200$_2$. In various embodiments, the first side piece 1200$_1$ can correspond to first side piece 902$_1$, and the second side piece 1200$_2$ can correspond to second side piece 902$_2$. In this embodiment, the first and second side pieces are mirror images of one another. Corresponding components in respective side pieces are denoted with the same reference numbers yet with the subscript 1 to indicate its association with the first side piece 1200$_1$ and the subscript 2 to indicate its association with the second side piece 1200$_2$. Repetitive description of like components is omitted for sake of brevity.

The respective side pieces are flexible/bendable and are adapted to bend and wrap around the wearer's hips when attached to the absorbent chassis. The respective side pieces are each defined by a laterally extending waist edge 1202$_1$ and 1202$_2$, a longitudinally opposing leg edge 1202$_1$ and 1202$_2$, a longitudinally extending front edge 1210$_1$ and 1210$_2$, and a longitudinally opposing back edge 1206$_1$ and 1206$_2$.

With reference to FIG. 12A in view of FIGS. 10-11B, in accordance with this embodiment, the back edges of the respective side pieces are adapted to attach to the back waist region 205 of the absorbent chassis 1000, and the front edges of the respective side pieces are adapted to attach to the front waist region 201. In particular, with reference to side piece 1200$_1$, the side piece may include a back-side attachment region 1204$_1$ adapted to removably attach with and/or connect to the second attachment region 1004$_1$ of the absorbent chassis 1000, and a front-side attachment region 1212$_1$ adapted to removably attach with and/or connect to the first attachment region 1002$_1$. Likewise, side piece 1200$_2$ may include like attachment regions 1204$_2$, 1212$_2$.

The respective side pieces $1200_1$ and $1200_2$ can further include a hip portion $1214_1, 1214_2$ disposed between the front-side attachment region $1210_1, 1210_2$ and the back-side attachment region $1204_1$, $1204_2$. In various embodiments, the hip portions $1214_1$ and $1214_2$ may be formed with an elastic material, such as an elastic durable or semi-durable material disclosed herein, including any of the materials used to form the ring belts disclosed above.

The back-side attachment regions $1204_1$ and $1204_2$ and/or the front-side attachment regions $1202_1$ and $1202_2$ may comprise any of the fastener components described herein.

Additionally, or alternatively, the back-side attachment regions $1204_1$ and $1204_2$ and/or the front-side attachment regions $1202_1$ and $1202_2$ may include indica printed on the garment-facing surface and/or wearer facing surface thereof (not shown) to indicate where to position and attach the respective back-side attachment regions $1204_1$ and $1204_2$ and/or the front-side attachment regions $1202_1$ and $1202_2$ to their corresponding attachment regions/components on the absorbent chassis $1000$ as discussed above.

As shown in FIG. 12A, the side pieces $1200_1$, $1200_2$ may have shape designed to facilitate fit and comfort over the wearer's hips and legs. For example, the length (e.g., along the longitudinal length along centerline Y-Y') of the front-side edges $1210_1$, $1210_2$ may be shorter than the length of the back-side edges $1206_1$, $1206_2$. For example, in the embodiment shown, the length of the front-side edges $1210_1$, $1210_2$ may be about 60 percent shorter, or from about 10% to about 90% shorter, than the length of the back-side edges $1206_1$, $1206_2$, reciting for said range every 5% increment therein. The leg edges $1208_1$, $1208_2$ may further taper diagonally from the front-side edges $1210_1$, $1210_2$ to the back-side edges $1204_1$, $1210_2$ as shown in FIG. 12A. The side pieces $1200_1$, $1200_2$ may also include and/or be defined by an upper hip region $1201$ and a lower leg region $1203$, wherein the upper hip region $1201$ may be laterally wider (e.g., along centerline X-X') then the lower leg region $1203$ as shown in FIG. 12A. Various other geometrical shapes for the side pieces $1200_1$ and $1200_2$ are envisioned.

For example, FIGS. 12B-12C provide additional side pieces of a two-piece reusable belt (e.g., side-piece belt $902$) in accordance with alternative embodiments. The respective side pieces are illustrated open and laid out flat with the wearer-facing surface oriented to the viewer. FIG. 12B presents one side piece $1205$ of a two-piece reusable belt, wherein the side piece $1205$ has a rectangular shape. In accordance with this embodiment, the other side piece of the two-piece belt can be identical to the one side piece $1205$ shown and thus is not illustrated to minimize redundancy. FIG. 12C presents one side piece $1207$ of a two-piece reusable belt, wherein the side piece $1207$ has a substantially rectangular shape yet a curved leg edge $1208$ that curves inward toward the direction of the waist edge $1202$. In accordance with this embodiment, the other side piece of the two-piece belt can also be identical to the one side piece $1207$ shown and thus is not illustrated to minimize redundancy. Aside from the differences in form factor, the side pieces $1205$ and $1207$ can have same or similar components, elements and materials as side pieces $1200_1$ and $1200_2$. Repetitive description of like elements is omitted for sake of brevity.

It is also contemplated that a multi-piece belt may comprise a front piece and a back piece that may attach to one another about the wearer's hip or side as shown in FIG. 13. FIG. 13 provides a high-level assembly configuration $1300$ for forming a wearable absorbent article $1306$ comprising a front/rear piece belt $1302$ and an absorbent chassis $1304$. In various embodiments, the absorbent chassis $1304$ is disposable and the front/rear piece belt $1302$ is reusable with additional absorbent chassis corresponding to absorbent chassis $1304$. Absorbent chassis $1304$ may correspond to absorbent chassis $200$ with some optional variations. For example, in some embodiments, one or more of the fastener components (e.g., fastener component $206$ and/or fastener component $220$) of absorbent chassis $200$ may be removed from absorbent chassis $1304$ and/or positioned in alternate locations to facilitate attachment of the absorbent chassis $1304$ to the front/rear piece belt $1302$ (or vice versa). Additional modifications are noted below.

As illustrated in FIG. 13, the front/back piece belt $1302$ comprises front piece $1302_1$ and a back piece $1302_2$. The front piece and the back piece are respectively defined by a length and two opposing ends (front piece ends $1308_1$ and back piece ends $1308_2$, respectively). The opposing ends $1308_1$ of the front piece $1302_1$ may be adapted to removably attach to the opposing ends $1308_2$ of the back piece $1302_2$ to form a ring belt. For example, the opposing ends of the front piece and/or the back piece may include fastener components adapted to removably attach to one another. The type of the fastener components may vary and include one or more of the fastener components disclosed herein. The wearable absorbent article $1306$ article can be assembled by attaching the opposing ends $1308_1$ of the front piece $1302_1$ to the opposing ends $1308_2$ of the back piece $1302_2$ about the wearer's hip or side, thereby connecting the front and back waist regions to form the wearable absorbent article $1306$. In some implementations, the absorbent chassis $1304$ may also include fastener components formed on the front and back waist regions thereof to which the front and back pieces are adapted to removably attach (e.g., first fastener component $206$ and/or second fastener component $220$). The front and back pieces may be adapted to removably and/or releasably attach to one another and/or the absorbent chassis $1304$ and be re-attached to and reused with one or more additional absorbent chassis. The respective front and back pieces may be formed with one or more of the durable and/or semi-durable materials discussed herein. In this regard, the respective front and back pieces may be launderable and/or laundering resistant.

FIG. 14 is a view of an example front/back piece belt $1400$ including a front piece $1402_1$ and a back piece $1402_2$. In various embodiments, the front piece $1402_1$ can correspond to front piece $1302_1$, and the back piece $1402_2$ can correspond to back piece $1302_2$. In this embodiment, the front and back pieces are substantially the same. Corresponding components of the respective front and back pieces are denoted with the same reference numbers yet with the subscript 1 to indicate its association with the front piece $1402_1$ and the subscript 2 to indicate its association with the back piece $1402_2$. Repetitive description of like components is omitted for sake of brevity.

The respective front and back pieces are flexible/bendable and are adapted to bend and wrap around the wearer's font and back body and attach to one another about the wearer's sides/hips. The respective front and back pieces are each defined by a laterally extending length disposed between longitudinally opposing ends $1408_1$ and $1408_2$. The respective front and back pieces further include central parts $1410_1$ and $1410_2$ positioned at a midpoint between the longitudinally opposing ends $1408_1$ and $1408_2$. The central parts $1410_1$ and $1410_2$ may respectively correspond to the front and back parts of one or more of the continuous ring belts discussed above (e.g., central part $1410_1$ may correspond to front part $512$ and central part $1410_2$ may correspond to back part 510 of one or more ring belts discussed with reference to FIGS. 5A-5I). For example, the central part $1410_1$ may be adapted for wear relative to the wearer's belly and the central part $1410_2$ may be adapted for wear relative to the wearer's back (or vice versa). The respective front and back pieces $1402_1$ and $1402_2$ are further defined by a wearer facing surface $1404_1$ and $1404_2$ and a garment-facing surface $1406_1$ and $1406_2$. In some embodiments, the central parts $1410_1$ and $1410_2$ may be adapted to removably attach to the front and back waist regions of the absorbent chassis via one or more fastener components formed on the wearer facing surface thereof (not shown), as described with reference to FIG. 5D. Additionally, or alternatively, the central parts $1410_1$ and $1410_2$ may be adapted to removably attach to the front and back waist regions of the absorbent chassis via one or more fastener components formed on the front and/or back waist regions of the absorbent chassis.

The opposing ends $1408_1$ and $1408_2$ of the front and back pieces include fastener components $1412_1$ and $1412_2$ that provide for attaching the front piece $1402_1$ and the back piece $1412_2$ to one another to form a continuous ring. The type of the attachment components $1412_1$ and $1412_2$ can vary and include one or more of the fastener components disclosed herein. The fastener components $1412_1$ and $1412_2$ may be located on the wearer facing surface $1404_1$ and/or the garment-facing surface $1406_2$ depending on the type of fastener components used. In the embodiment shown, a dashed box is used indicate the location of a fastener component on the non-visible surface of the belt-piece. For example, in the embodiment shown, the fastener components $1412_1$ may include female attachment components (e.g., hooks) formed on the garment-facing surface $1406_1$ of ends $1408_1$, and the fastener components $1412_2$ may include paired male attachment components (e.g., loops) formed on the wearer facing surface $1404_2$ of ends $1408_2$. With this embodiment, the font piece $1402_1$ may be connected to the back piece $1402_2$ by attaching the female attachment components to the male attachment components of the respective ends $1408_1$ and $1408_2$. Various other fastener configurations for the ends $1408_1$ and $1408_2$ are envisioned.

The materials used for the central portions $1410_1$ and $1410_2$, the ends $1408_1$ and $1408_2$, and the portions of the belt pieces disposed between the central portions and the ends (illustrated with lined fill) can include one or more of the durable or semidurable materials disclosed herein. The materials used for the central portions $1410_1$ and $1410_2$, the ends $1408_1$ and $1408_2$, and the portions of the belt pieces disposed between the central portions and the ends may include same or different materials. In various embodiments, the portions of the belt pieces disposed between the central portions and the ends may include an elastic material while the central portions $1410_1$ and $1410_2$, the ends $1408_1$ and $1408_2$ may comprise an inelastic material or partially elastic material.

FIG. 15 provides a high-level assembly configuration 1500 for forming a wearable absorbent article 1506 comprising a strip belt 1502 and an absorbent chassis 1504 in accordance with another embodiment. In various embodiments, the absorbent chassis 1504 is disposable and the strip belt 1502 is reusable with additional absorbent chassis.

As illustrated in FIG. 15, the strip belt 1502 comprises two opposing ends 1510 connected to one another by a strip portion 1508 of material adapted to wrap partially around the wearer's waist. In this regard, the width of the strip belt 1502 is adapted to wrap around a first waist region of the absorbent chassis 1504 and the opposing ends 1510 are adapted to removably and releasable attach to portions of the second waist region, thereby connecting the first waist region and the second waist region to form the wearable absorbent article 1506. In some implementations, the first waist region may be the back waist region and the opposing ends 1510 may be adapted to removably attach to the front waist region. In other implementations, the first waist region may be the front waist region and the opposing ends 1510 may be adapted to removably attach to the back waist region.

One or more portions of the strip belt 1502 and/or the absorbent chassis 1504 may include fastener components to provide for temporarily attaching the strip belt 1502 to the absorbent chassis 1504 (or vice versa). For example, in some implementations, the absorbent chassis 1504 may include fastener components formed on portion(s) of the front and/or back waist regions to which the opposing ends 1510 are adapted to attach. Additionally, or alternatively, wearer-facing surfaces of the opposing ends 1510 can include fastener components adapted to attach to portion(s) of either the front or back waist regions of the absorbent chassis 1504. In these embodiments, the strip belt 1502 may be adapted to removably and/or releasably attach to the absorbent chassis 1504 and be re-attached to and reused with one or more additional absorbent chassis.

The strip belt 1502 may be formed with one or more of the durable and/or semi-durable materials discussed herein. In this regard, the strip belt 1502 may be launderable and/or laundering resistant. The ends opposing ends 1510 and the strip portion 1508 may be formed with the same piece of material (a single layer or multi-layer piece of material) or different pieces of materials that a permanently attached/bonded to one another (e.g., adhesively bonded/glued, sewn, thermally bonded, ultrasonically bonded, etc.). The strip belt may be elastic.

FIGS. 16A and 16B depict another absorbent chassis 1600 adapted for use with a strip belt such as strip belt 1502. FIG. 16A is a front-side perspective shown in a folded configuration, and FIG. 16B is a back-side perspective in the folded configuration.

Absorbent chassis 1504 and absorbent chassis 1600 can include same or similar elements and forms as other absorbent chassis disclosed herein with some differences tailored for use with a strip belt. Repetitive description of like elements is omitted for sake of brevity.

With reference to FIGS. 15, 16A and 16B, in various embodiments, one of the opposing ends 1510 of the strip belt 1502 can be adapted to attach to first attachment region $1002_1$ on the front side of the absorbent chassis 1600 and the other opposing end 1510 may be adapted to attach to first attachment region $1002_2$ on the opposite front side of the absorbent chassis 1600. The mechanism of attachment can vary. For example, as discussed with reference to FIGS. 10A and 10B, the first attachment regions $1002_1$, $1002_2$ may include or correspond to mechanical fastener components that may be adapted to removably attach to wearer facing surfaces of the opposing ends 1510 of the strip belt 1502. Additionally, or alternatively, the wearer facing surfaces of the opposing ends 1510 off the strip belt 1502 may include mechanical fastener components adapted to removably attach to the first attachment regions $1002_1$, $1002_2$ and/or paired fastener components formed on the first attachment regions $1002_1$, $1002_2$. In either of these embodiments, the attachment regions and/or fastener components may include any of the types of fastener components disclosed herein.

In some implementations, a central region of the inner (wearer-facing) surface of strip portion 1508 of the strip belt 1502 may also be adapted to attach to the second fastener component 220 on the backside of the absorbent chassis 1600. The central region can be located at or near a center-point or midline between the opposing ends 1510. The mechanism of attachment of the central region of the strip portion to the second fastener component 220 can vary. In this regard, the second fastener component 220 can include any of the fastening components discussed herein. Additionally, or alternatively, the wearer facing surface of the central region of the strip portion 1508 may include one or more fastener components adapted to removably attach to the back waist region of the absorbent chassis and/or the second fastener component 220. In other implementations, the wearer facing surface of a central region of the strip portion 1508 designed to contact the back waist region of the absorbent chassis 1506 can comprise a material configured to cling or stick to the absorbent chassis surface material via adhesion or cohesion (e.g., a fibrous material, a rubber material, a plastic material, etc.).

FIG. 17 provides a high-level assembly configuration 1700 for forming a wearable absorbent article 1714 comprising a multi-piece reusable belt and an absorbent chassis 1708. The multi-piece reusable belt includes strip belt 1502 and a landing zone piece 1702 adapted to removably attach to one another and the absorbent chassis 1708 to form the wearable absorbent article 1714. With this embodiment, the landing zone piece 1702 may be adapted to removably attach to the front waist region of the absorbent chassis 1708 and the opposing ends 1510 of the strip belt 1502 may be adapted to removably attach to opposite ends of the landing zone piece 1702. In this regard, the landing zone piece 1702 is illustrated in FIG. 17 with the garment-facing surface oriented to the viewer. The landing zone piece 1702 may be defined by upper and lower lateral edges 1701 and opposing side edges 1703. The landing zone piece 1702 may include a first attachment region 1704 on the wearer-facing surface at or near a midline/center point of the landing zone piece (e.g., at a midpoint between the upper and lower lateral edges 1701 and the opposing side edges 1703). This first attachment region 1704 may be adapted to attach to a corresponding attachment region 1710 located on the front waist region of the absorbent chassis. The mechanisms of attachment can vary. For example, either the first attachment region 1704 or the attachment region 1710, or both, may include any of the mechanical fastener components disclosed herein. In some implementations, the first attachment region 1704 may include an adhesive patch (such the adhesive patch 402 described with reference to FIG. 4C) adapted to removably attach to the attachment zone 1710. In some implementations, an attachment region may include or correspond to indicia that indicates how to align and position the respective elements relative to one another for their attachment.

The landing zone piece 1702 further includes second attachment regions 1706 positioned on opposite sides of the first attachment region 1704 on the garment-facing surface of the landing zone piece 1702. As illustrated in FIG. 17, the landing zone piece 1702 may attach to the front waist region of the absorbent chassis 1708 via the first attachment region 1704 and/or the attachment region 1710 to form intermediate structure 1712. The strip belt 1502 can thereafter be wrapped around the back waist region of the absorbent chassis and the opposing ends 1510 of the strip belt can attach to the second attachment zones 1706 of the landing zone piece 1702, resulting in formation of wearable absorbent article 1714. The mechanism of attachment of the opposing ends 1510 of the strip belt 1502 to the second attachment regions 1706 can vary. For example, either the second attachment regions 1706 or the wearer facing surfaces of the opposing ends 1510, or both, may include any of the mechanical fastener components disclosed herein that provide for removably and/or releasably attaching the respective elements to one another. In some implementations, the second attachment region 1706 may also include adhesive patches (such the adhesive patch 402 described with reference to FIG. 4C) that the opposing ends 1510 may be removably attached to. Additionally, or alternatively, the second attachment regions may comprise loops for use with a hook-and-loop system. In implementations in which only the opposing ends 1510 include a mechanical fastener component, the second attachment regions may be removed. Additionally, or alternatively, the landing zone piece may include printed indicia that indicates how to align and position the opposing ends 1510 relative thereto when attaching them to the landing zone piece 1702. The absorbent chassis 1708 and/or the strip belt 1502 may also include any of the attachment means previously described.

In some embodiments, the landing zone piece 1702 can enable efficient conversion of existing absorbent chassis into absorbent chassis adapted for use with a reusable belt. In this regard, rather than incorporating a fastener component in the attachment region 1710 of the absorbent chassis 1708 (which may require adapting exiting absorbent chassis manufacturing lines), the landing zone piece 1702 can serve as the attachment mechanism. With these embodiments, the attachment region 1710 of the absorbent chassis may be removed. In some implementations of these embodiments, the landing zone piece 1702 may be disposable and/or adapted to remain attached to the absorbent chassis 1708 when the strip belt 1502 is removed. Alternatively, the landing zone piece 1702 may be reusable and formed with one or more of the durable and/or semi-durable materials discussed herein. The landing zone piece 1702 may be formed with a nonwoven material, comprising a plurality of loops, or a film. In this regard, the strip belt landing zone piece 1702 may be launderable and/or laundering resistant.

FIG. 18A provides a high-level assembly configuration 1800 for forming a wearable absorbent article 1810 comprising a multi-piece reusable belt and an absorbent insert 1806. Assembly configuration 1800 is similar to assembly configuration 100 with the exchange of the disposable chassis 104 for a crotch-piece 1802 and an absorbent insert 1806, wherein crotch-piece is adapted to receive the absorbent insert 1806, and wherein the crotch piece 1802 is reusable. The multi-piece reusable belt in accordance with this embodiment refers to the combination of the ring belt 102 and the crotch-piece 1802.

In this regard, the crotch piece 1802 can correspond to an outer shell component of a multi-piece absorbent article adapted to receive an absorbent insert 1806. In the embodiment shown, the crotch piece 1802 includes an insert attachment zone 1804 located on the wearer facing surface thereof adapted to receive the absorbent insert 1806. Preferably, the absorbent insert 1806 is adapted to removably attach to the insert attachment zone 1804 via an adhesive formed on the garment facing surface thereof. Other attachment mechanisms are envisioned. The combined/attached absorbent insert 1806 and crotch-piece 1802 form an absorbent chassis structure 1808 that may correspond to the various absorbent chassis discussed above with some differences noted below. In this regard, the ring belt 102 can be adapted to removably attach to the garment facing surface of the absorbent chassis structure 1808 to form the wearable absorbent article 1810 in a same or similar manner discussed with reference to FIGS. 1-7. In some embodiments, at least a portion of the crotch piece 1802 may permanently bonded to continuous ring belt. For example, the garment facing surface of either the front or back waist region of the crotch piece 1802 may be permanently bonded to the wearer facing surface of the ring belt, as shown in FIG. 18B, which depicts the crotch piece as open and laid out flat with the wearer facing surface oriented to the viewer. Repetitive description of like elements employed in respective embodiments is omitted for sake of brevity.

FIG. 19A is a view of an inner (wearer-facing) surface of an example crotch piece 1900 of a multi-piece reusable belt as opened and laid flat. FIG. 19B is a view of the inner (wearer-facing) surface of the crotch piece with an absorbent insert 1806 attached thereto. In various embodiments, crotch piece 1802 can correspond to crotch piece 1900 (or vice versa).

With reference to FIGS. 2A, 2B, 19A and 19B, the crotch piece 1900 can substantially correspond to absorbent chassis 200 yet with the absorbent core region 226 removed, or with the absorbent core region 226 and layers above the absorbent core (e.g., the topsheet) removed. In this regard, the garment-facing surface 208 of the crotch piece 1900 can include same or similar elements/components as the garment facing surface of absorbent chassis 200, such as one or more of the backsheet or layers thereof disclosed above. As shown in FIGS. 19A and 19B, the wearer-facing surface 222 of the crotch piece may include an insert attachment zone 1804 adapted to receive the absorbent insert 1806. As shown in FIG. 19B, the absorbent insert 1806 may be defined by a first lateral end 1902, a second lateral end 1904 opposite the first lateral end, opposing side edges 1906, and a length in a longitudinal direction extending between the first lateral end and the second lateral end. The absorbent insert 1806 can further include the absorbent core region 226.

FIG. 20 is a cross sectional view of an example absorbent insert 1806 taken along centerline X-X' in FIG. 19B. As illustrated in FIG. 20, the absorbent insert 1806 can include same or similar elements of the absorbent core region of the disposable chassis 200. For example, the absorbent insert can include the topsheet 302, the absorbent core 306 and optionally a layer of backsheet 304 such as film. It is also contemplated that the insert does not include the backsheet 306 or any layers thereof. The topsheet 302 in this implementation can be or correspond to the wearer-facing surface of the absorbent insert 1806. Repetitive description of like elements employed in respective embodiments is omitted for sake of brevity.

The absorbent insert 1806 may further include an adhesive layer 2002 formed on its garment-facing surface and a protective layer 2004 formed thereon. The absorbent insert may be removably attached to the insert attachment zone 1804 of the crotch piece 1900 when the protective layer 2004 is removed to reveal the adhesive layer 2002 thereunder. In this regard, the adhesive layer 2002 may include a glue that provides for forming a semi-permanent bond between the adhesive layer and the crotch piece 1900, such as a glue that does not crystalize. Preferably, the adhesive layer 2002 can include a pressure-sensitive hotmelt glue. The protective layer 2004 may comprise silicone-coated paper, or other suitable materials as discussed above in reference to protective layer 406.

With reference again to FIGS. 18, 19A, 19B and 20, in various embodiments, the crotch piece 1802 and/or crotch piece 1900 may be formed with one or more durable and/or semi-durable materials disclosed herein. In this regard, unlike the absorbent chassis described herein, the crotch piece 1802 and/or the crotch piece 1900 does not include the topsheet 302 or the absorbent core 306, or other known diaper components such as acquisition/distribution systems. In some implementations, the crotch piece 1802 and/or the crotch piece 1900 can be formed with the same or similar materials as the ring belt 102.

In some embodiments, any of the absorbent chassis of the wearable absorbent articles discussed above can be replaced with a corresponding crotch piece and absorbent insert combination.

For example, FIG. 21 provides a high-level assembly configuration 2100 for forming a wearable absorbent article 2106 comprising a multi-piece reusable belt and an absorbent insert 1806. Assembly configuration 2100 is similar to assembly configuration 900 with the exchange of the disposable chassis 904 for a crotch-piece 2102 and the absorbent insert 1806, wherein crotch-piece 2102 is adapted to receive the absorbent insert 1806, and wherein the crotch piece 2102 is reusable. The multi-piece reusable belt in accordance with this embodiment refers to the combination of the two-piece belt 902 and the crotch-piece 2102.

In this regard, the crotch piece 2102 can correspond to crotch piece 1802 and/or crotch piece 1900, yet with the wearer-facing surface components and elements of the absorbent chassis 1000. For example, the crotch piece 2102 includes an insert attachment zone 1804 located on the wearer facing surface thereof adapted to receive the absorbent insert 1806. Preferably, the absorbent insert 1806 is adapted to removably attach to the insert attachment zone 1804 via an adhesive formed on the garment-facing surface thereof. Other attachment mechanisms are envisioned. The combined absorbent insert 1806 and crotch-piece 2102 form an absorbent chassis structure 2104 with the wearer-facing surface components/elements of absorbent chassis 1000. In this regard, the two-piece belt 902 can be adapted to removably attach to the garment-facing surface of the absorbent chassis structure 2104 to form the wearable absorbent article 2106 in a same or similar manner discussed with reference to FIGS. 9-12C. Repetitive description of like elements employed in respective embodiments is omitted for sake of brevity.

FIG. 22 provides a high-level assembly configuration 2200 for forming a wearable absorbent article 2204 comprising an outer shell 2202 and an absorbent insert 1806 in accordance with another embodiment. In accordance with this embodiment, the outer shell 2202 can be reusable and adapted to receive insert 1806. The outer shell 2202 can correspond to a pant that is formed with one or durable or semi-durable materials disclosed herein. In this regard, as shown in FIG. 22, the outer shell 2202 may include a crotch region 2208 and a waist region 2206 that are connected in a unibody pant configuration. The outer shell 2202 can further include an insert attachment zone 1804 on the wearer-facing surface thereof adapted to receive the absorbent insert 1806. With this embodiment, the absorbent insert 1806 can include the adhesive layer attachment mechanism discussed above. Various outer cover and pant configurations that can be used for the outer shell 2302 are disclosed in U.S. Patent Publication Nos. 2007/0078426; and 2008/0107861 and U.S. Patent Appl. Nos. 63/028,021 and 63/080,864.

In various embodiments, the wearable absorbent articles disclosed herein as assembled are adapted for wear as a pant around the lower torso of a wearer to contain and/or absorb urine, feces, menses or any combination thereof. The wearable absorbent article can be configured to be pre-assembled prior to wear (e.g., at the time of packaging) and/or assembled at the time of wear by attaching the components (e.g., absorbent chassis to reusable belt, insert to outer shell, etc.) as disclosed above and then positioning the article on the wearer. After wear/soiling, the wearable absorbent article can be removed from the wearer and the components can be detached. The used/soiled absorbent chassis/insert can be disposed of, and the belt/outer cover or other reusable components can further be re-used and reattached to one or more additional absorbent components.

The wearable article may comprise one or more sleeves. In some embodiments, the chassis may comprise a sleeve which may serve as a fastener component, holding the belt. A sleeve may be provided on the belt, side piece, font piece, back piece, or outer shell with a fastening component disposed thereon. In nonlimiting examples, a sleeve provided on a belt, side piece, or outer shell may be configured in slidable relationship with said belt/side piece/outer shell, permitting the belt/side piece/outer shell and the chassis to be attached at various locations.

A sleeve may be provided on the chassis and function as a belt-loop for a ring belt, strip belt, or a font/back piece belt, as shown in FIGS. 23A-23D. Likewise, a sleeve can be provided on a crotch piece to serve as a holder for an absorbent insert.

The sleeve(s) may be provided in the first and/or the second waist region of the absorbent chassis, and may be provided on a garment-facing surface or the wearer-facing surface. In various examples, a sleeve is provided on the garment-facing surface. As shown in FIG. 23A for example, the sleeve 2300 can be defined by an upper edge 2302, a lower edge 2304 opposite the upper edge 2302 in the longitudinal direction, and two side edges 2306. One or both of the upper and lower edges may be permanently attached to the chassis (e.g., permanently adhesively bonded, thermally bonded, ultrasonically bonded, sewn or the like). One or more both of the upper and lower edges may be removably attached to the absorbent chassis to permit the sleeve to at least partially detach from the chassis. For example, FIGS. 23B-23D illustrate a detachable sleeve 2300 for the second fastener component 220 on the backside of the absorbent chassis 200. In some implementations, a same or similar detachable sleeve 2300 can be used for the first fastening component 206. In the example embodiment in FIGS. 23A-B, the upper edge 2302 is permanently attached to the absorbent chassis 200 and the lower edge 2304 is removably attached to the absorbent chassis via a first fastener component 2308 formed on an internal surface of the lower edge 2304 and a second fastener component 2310 formed on the absorbent chassis 200. The first fastener component 2308 can be adapted to releasably attach to the second fastener component 2310 to form the sleeve 2302, as shown in FIG. 23B. The type of the first fastener component 2308 and the second fastener component 2310 can vary and include one or more of the fasteners discussed herein.

Further to the above, FIGS. 23C-23D illustrate another detachable sleeve 2301 wherein the upper and lower edges 2302 and 2304 of the detachable sleeve 2301 can include attachment regions 2314 respectively configured to align with and attach to corresponding attachment regions 2312 located on the absorbent chassis. FIG. 23C depicts the absorbent chassis 200 with the detachable sleeve 2301 removed and the ring belt 102 positioned between the attachment regions 2312. FIG. 23D depicts the absorbent chassis 200 with the detachable sleeve 2301 attached to the absorbent chassis with the ring belt 102 positioned thereunder. The attachment mechanism used to removably attach the detachable sleeve 2301 to the absorbent chassis 200 can vary. Any suitable fastening components may be utilized.

FIG. 24 illustrates a block diagram of an example, non-limiting multi-piece absorbent article manufacturing system (hereinafter system 2400) that facilitates manufacturing the multi-piece absorbent articles described with reference to FIGS. 1-23D in accordance with one or more embodiments of the disclosed subject matter. Embodiments of systems described herein can include one or more apparatuses. Additionally, or alternatively, the systems may include machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

System 2400 may include an absorbent chassis formation unit 2402, a reusable belt formation unit 2404, an assembly unit 2406 and a control unit 2410. The absorbent chassis formation unit 2402 may include or one or more apparatuses adapted to perform a variety of manufacturing processes for forming the absorbent chassis portions of the wearable absorbent articles described with reference to FIGS. 1-23D. The reusable belt formation unit 2404 may include or one or more apparatuses adapted to perform a variety of manufacturing processes for forming the reusable belt portions of the wearable absorbent articles described with reference to FIGS. 1-23D. The assembly unit may include one or more apparatuses adapted to pre-assemble the wearable absorbent articles described with reference to FIGS. 1-23D. In this regard, the pre-assembling process can include attaching the reusable belt portions to the absorbent chassis via the one or more temporary fastener components formed on the belt portions and/or the absorbent chassis portions. The pre-assembled wearable absorbent articles may be packaged with additional absorbent chassis without the belt portions attached thereto and the belt portion of a pre-assembled wearable absorbent article may be removably attached by consumer and reattached to and reused with the additional absorbent chassis. Additional details regarding the manufacturing processes for forming the absorbent chassis, the reusable belts and the pre-assembled wearable absorbent articles are described below. The control unit 2410 can include hardware and/or software that provides for controlling one or more operations of the absorbent chassis formation unit 2402, the reusable belt formation unit 2404 and the assembly unit 2406.

FIG. 25 illustrates a block diagram of an example, non-limiting absorbent chassis formation unit 2402. The absorbent chassis formation unit 2402 includes several assembly units respectively configured to perform different transformation processes of an assembly line for forming the absorbent chassis described herein. The different transformation processes are adapted to produce a series of transformations to different material components/elements of the absorbent chassis disclosed herein to assemble/form the absorbent chassis. In this regard, the absorbent chassis formation unit 2402 may assemble the absorbent chassis disclosed herein by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete absorbent articles.

In this regard, the absorbent chassis formation unit 2402 may include a web transformation unit 2502 adapted to transform one or more webs (e.g., embossing a topsheet, a printing a backsheet, and/or an absorbent core). The web transformation unit 2502 may include one or more assembly units, including for example, a core assembly unit 2504 adapted to form the absorbent core. The core assembly unit 2504 may be configured in accordance with the converting apparatuses described in U.S. Pat. Nos. 10,470,948, and 10,376,428, the entirety of which is incorporated herein by reference. The web transformation unit 2502 may further include a first series assembly unit 2506 adapted to combine a first series of webs such as combine a topsheet, backsheet to envelope an absorbent core and optionally an acquisition-distribution system adapted to combine additional components to the first series such as combining leg cuff materials to the topsheet and/or backsheet. The web transformation unit 2502 may further include a second series assembly unit 2508 adapted to further combine additional components (e.g., waistbands, ears, landing zones, printing), and a fastener assembly unit 2510 adapted to perform a fastener component assembly process. The absorbent chassis formation unit 2402 may further include cutting unit 2512 adapted to perform a chassis cutting process; and folding unit 2514 adapted to perform a chassis folding process. Any number of further units may be added and some may be removed as applicable for the end product.

Each of the units of the absorbent chassis formation unit 2402 may include one or more components connected to one another in an assembly line configuration. In this regard, the respective assembly units can be configured in accordance with the converting apparatuses described in U.S. Pat. No. 9,226,861, U.S. patent application Ser. No. 13/371,919, entitled "Tape and Pant Diapers Comprising Substantially Identical Absorbent Chassis" filed on Feb. 12, 2012, the entirety of which is incorporated herein by reference.

The method of operation of the absorbent chassis formation unit 2402 may described with reference to the various components of the absorbent chassis described above and shown in FIGS. 1-23D. It is to be appreciated transformations shown and described herein can be carried out in various different orders than that which is depicted and described herein.

FIG. 26 provides a high-level flow diagram of an example process 2600 for forming one or more of the absorbent chassis shown in FIGS. 1-23D that may be performed by the absorbent chassis formation unit 2400. With reference to FIGS. 2A, 2B, 3, 25 and 26, as shown in method 2600, the absorbent chassis assembly process 2600 may involve assembling the absorbent core at 2602 via the absorbent core assembly unit 2504. Alternatively, the absorbent core may be received by the absorbent chassis formation unit 2402 pre-assembled. Process 2600 may further include assembling the topsheet to the absorbent core at 2604 and assembling the backsheet to the absorbent core at 2606 (e.g., via the first series assembly unit 2506). In addition, the second series assembly unit 2508 may perform a leg cuff assembly process at 2608 to assemble the leg cuffs 210, which may be combined with the advancing topsheet forming the topsheet substrate. The second series assembly unit 2508 may also perform a leg elastic assembly process at 2610. In some implementations, the leg elastics are combined with the advancing backsheet substrate through the second series assembly unit 2508. In addition, the fastener assembly unit 2510 may perform a fastener assembly process at 2612 to assemble one or more fastener components (e.g., first fastener component 206, second fastener component 220, and the like) on the backsheet 304 in embodiments in which the absorbent chassis includes fastener components adapted to removably attach to the belts and/or belt elements of the reusable belt. The output of the assembly process at 2612 may include a continuous length of absorbent chassis (e.g., a plurality of absorbent chassis connected to one another in the longitudinal direction along centerline Y-Y'). At 2614, the absorbent chassis are cut (e.g., via the cutting unit 2512) into separate absorbent chassis to create the front waist ends 202 and second waist ends 216. The respective absorbent chassis are then folded at 2616 by the folding unit 2514.

It is to be appreciated that one or more transformations may occur during each process step of process 2600. Such transformations include for example: substrate positioning; adhesive application; material laydown (e.g., superabsorbent material deposition, distribution layer material distribution, etc.); registration; cutting/trimming/slitting; bonding; stretching/tensioning; winding/unwinding; printing; plastically deforming; embossing and combinations thereof.

The fastener assembly process at 2612 may include a variety of different transformation to account for the variety of different absorbent chassis and reusable belt configurations disclosed herein. For example, in some embodiments, the fastener assembly process may be omitted (e.g., in embodiments in which the absorbent chassis does not include any fastener components). The fastener assembly process can also vary depending on the type of fastener components applied to the absorbent chassis which can vary as discussed above. The fastener assembly process can also vary with respect to the locations/positions where fastener components are applied to the absorbent chassis, which can vary depending on the type of reusable belt with which the absorbent chassis are adapted to be used with. The fastener assembly process can also vary based on whether the absorbent chassis will be pre-assembled (e.g., by the assembly unit 2406) or manufactured as replacement chassis. For example, in some embodiments in which adhesive patch (e.g., adhesive patch 402) fastener components are attached, the fastener assembly process may include applying the adhesive layer (e.g., adhesive layer 404) and applying the protective layer (e.g., protective layer 406) over the adhesive layer thereafter 406. However, in some implementations in which the wearable absorbent chassis is pre-assembled with the reusable belt removably/releasably attached thereto, the protective layer 406 may not be applied.

In this regard, in some embodiments, the fastener assembly unit 2510 can be adapted to form one type of absorbent chassis disclosed herein. In other embodiments, the fastener assembly unit 2510 can be adapted to form two or more types of the absorbent chassis disclosed herein using the same machinery, by adjusting the fastener assembly process (wherein the other portions of the absorbent chassis may remain the same, regardless of the type of reusable belt to be used). In some implementations of these embodiments, the control unit 2410 can control the type of absorbent chassis produced by directing (e.g., via one or more control signals) the faster assembly unit 2510 accordingly. For example, the control unit 2410 can direct the fastener assembly unit 2510 to apply the fastening component(s) or no fastening components in accordance with a desired absorbent chassis configuration. In this regard, the fastener assembly unit 2510 can be programmable to apply fastener components or no fastener components (e.g., adhesive patches or the like) at different positions and in different configurations/patterns to achieve a configuration consistent for use with a ring belt with a fastener component, another configuration consistent for use with a ring belt without a fastener component, another configuration consistent for use with a side-piece belt with or without a fastener component, another configuration consistent for use with a strip belt a fastener component, another configuration consistent for use with a multi-piece landing zone belt, and so on.

Some example transformation steps that may be performed in association with application of the different fastening components in accordance with the different chassis configurations described herein may include but are not limited to: (1) Spacing (2) Adhesive Application; (3) Protective Layer Application; (4) hook-and-loop fastener application, (5) Back Sleeve Cutting (6) Back Sleeve Preparation (7) Back Sleeve Positioning; and (8) Back Sleeve attaching.

The folding unit 2514 herein may include various types of mechanisms to perform the folding transformation at 2616 as well as the folding transformations discussed below with reference to FIGS. 30 and 31. For example, the folding unit 2514 may utilize a folding apparatus similar to those described in U.S. Patent Publication Nos. 2009/0094941 A1 and 2009/0098995 A1. The folding transformation herein may also utilize the folding methods and apparatuses described in U.S. patent application Ser. No. 13/051,210.

FIG. 27 illustrates a block diagram of an example, non-limiting reusable belt formation unit 2404. The reusable belt formation unit 2404 includes several units respectively configured to perform different transformation processes of an assembly line for forming the reusable belts described herein. These different units may include an elastic portion assembly unit 2702, a cutting unit 2704, a ring belt fusing unit 2706, a front/back portion unit 2708, an opposing ends unit 2710, a fastener assembly unit 2712, a belt parts attachment assembling unit 2714, and a landing zone piece unit 2716. The different transformation processes performed by the respective units are adapted to produce a series of transformations to different material components/elements of the reusable belts disclosed herein to assemble/form the reusable belts. The different transformation processes can vary depending on the type of reusable belt being formed and the various different configurations of the different types of reusable belts disclosed herein. In some embodiments, the reusable belt formation unit 2404 can be adapted to form one type of the reusable belts disclosed herein. In other embodiments, the reusable belt formation unit 2404 can be adapted to form two or more type of the reusable belts disclosed herein using the same units and/or different instances one or more of the respective units tailored to a different type of reusable belt.

In this regard, the elastic portion assembly unit 2702 may be adapted to perform an assembly processes for forming the elastic material of the different reusable belts disclosed herein. For example, this elastic material can include the entirety of the continuous ring belt (e.g., continuous ring belt 102 and variations thereof), the entirety or portions of the side pieces of the side piece belts (e.g., side piece belt 902 and variations thereof), the entirety or portions of the front/back piece belts (e.g., front/back piece belt 1302 and variations thereof), and the entirety or the strip portion (e.g., strip portion 1508) of the strip belts (e.g., strip belt 1502 and variations thereof). In some embodiments, the elastic portion assembly unit 2702 may form the elastic material by bonding two or more layers of durable or semi-durable materials using various bonding techniques (e.g., adhesive bonding, pressure bonding, thermal bonding, ultrasonic bonding, etc.). Alternatively, the elastic portion assembly unit 2702 may be omitted and the elastic material used to form the elastic portions of the belts may be provided to the reusable belt formation unit pre-assembled.

The elastic portion cutting unit 2704 may be adapted to cut the elastic material into separate pieces that may be used to form the continuous ring belts (e.g., continuous ring belt 102 and variations thereof), the side pieces of the side-piece belts (e.g., side-piece belt 902 and variation thereof), the front and back pieces of the front/back piece belts (e.g., front/back piece belt 1302 and variations thereof), and/or the strip portion of the strip belts (strip belt 1402 and variations thereof). For example, the elastic portion cutting unit 2704 may be adapted to cut the elastic material into strips that may be fused end-to-end to form a continuous ring belt. With these implementations, the ring belt fusion unit 2706 may be adapted to perform a fusing process to fuse opposite ends of cut elastic material to one another to form the continuous ring belts in implementations in which the ring belts are formed with a same piece of material (e.g., ring belt 501 as shown in FIG. 5A, ring belt 503 as shown in FIG. 5B, ring belt 812 as shown in FIGS. 8A-8D, and the like). For example, the ring belt fusion unit 2706 may employ various techniques to fuse the opposite ends of the elastic material together (e.g., adhesive bonding, pressure bonding, thermal bonding, ultrasonic bonding, sewing or the like). The elastic portion cutting unit 2704 may also be adapted to cut the side pieces 514 of the continuous ring belts that employ front and back portions formed with a different material as illustrated in FIGS. 5C-7). The elastic portion cutting unit may also be adapted to cut elastic material into side pieces for the side-piece belts, the front and back pieces of the front/back piece belts, and/or strip pieces for the strip portion of the strip piece belts.

The front/back portion unit 2708 may be adapted to form the front and back portions (e.g., front portion 512, back portion 510 and variations thereof) of the ring belts and/or the front/back piece belts disclosed herein. For example, the front/back portion unit 2708 may be adapted to cut the front and back portions from a supplied front/back portion material substrate. In some implementations, the front/back portion unit may also be adapted to form the front/back portion material substrate prior to cutting. Similarly, the opposing ends unit 2710 may be adapted to form the opposing ends portions (e.g., opposing ends 1510) of the strip belts in implementations in which the strip belts are formed from a different material relative to the elastic strip portion. The opposing ends unit 2710 may also be adapted to form the front-side attachment region $1212_1$ portion and the back-side attachment region $1204_2$ of the side pieces in implementations in which they are formed from a different material relative to the elastic strip portion. In this regard, the opposing ends unit 2710 may be adapted to form the opposing ends and/or front/back side attachment regions by cutting them from a second material substrate. The landing zone piece unit 2716 may further be adapted to form the landing zone pieces (e.g., landing zone piece 1702) of the multi-piece belts incorporating landing zone pieces as shown in FIG. 17).

The fastener assembly unit 2712 may be adapted to form the fastening components of the reusable belts in implementations in which the reusable belts include fastening components. The mechanism for applying the fastening components to the corresponding reusable belt parts can vary depending on the type of fastening components used (e.g., adhesive patches, hook-and-loop fasteners and other types of releasably fastening components disclosed herein). In some embodiments, the fastener assembly unit 2712 may apply the fastening components to corresponding portions of the reusable belts prior to cutting and shaping (e.g., by the elastic portion cutting unit 2704, the front/back portion unit 2708, and/or the opposing ends unit 2710).

The belt parts attachment assembly unit 2714 may be adapted to bond/attach respective parts of the reusable belts to one another. For example, with respect to the reusable belt embodiments that include a front portion 512 and a back portion 510 as shown in FIGS. 5C-5I and FIG. 14, the belt parts attachment assembly unit 2714 may be adapted to bond the front portion 512 and the back portion 510 to the respective elastic side portions 514. In another example, belt parts attachment assembly unit 2714 may be adapted to bond the front-side attachment region 1212₁ portion and the back-side attachment region 1204₂ of the side pieces to the elastic portions 1214₁ and 1214₂. In another example, the belt parts attachment assembly unit 2714 may be adapted to attach the opposing ends 1510 portions of the strip belt to the strip portion 1508.

With reference again to FIG. 24, as previously discussed, in some embodiments, the multi-piece wearable absorbent articles may be pre-assembled prior to wear. With these embodiments, the assembly unit 2406 can perform a pre-assembly process. To facilitate this end, the assembly unit 2406 can include one or more machine assembly components that attach the reusable belts and/or their parts to their corresponding absorbent chassis via the temporary (e.g., removably/releasably attachable) fastening components formed on the belts and/or the absorbent chassis. For example, with reference to FIGS. 1, 9, 13, 15, and 17, the assembly unit 2406 can be adapted to attach a continuous ring belt 102 (and variations thereof), a side-piece belt 902 (and variations thereof), a front/back piece belt 1302 (and variations thereof), a strip belt 1502 (and variations thereof), and/or a landing zone piece 1702 (and variations thereof) formed by the reusable belt formation unit 2404 to an absorbent chassis formed by the absorbent chassis formation unit 2402 via one or more fastener components disposed on the belt and/or the absorbent chassis to form wearable absorbent article.

Any suitable fastening component type may be utilized to removably join the belt to the absorbent chassis. In nonlimiting examples, fastening components for attaching the belt and absorbent chassis comprise adhesive, more particularly hot melt adhesives. An adhesive bond may be disposed in a pattern that may be substantially continuous in one or both of the lateral or longitudinal directions across the absorbent chassis and/or reusable belt or it may form an intermittent pattern in one or both of those directions. The adhesive bond may also be in the form of one or more beads, one or more spirals, one or more repeating, e.g., zigzag, or random, e.g., spray, patterns, one or more slot coatings or may be formed by printing of the adhesive. In nonlimiting examples, an adhesive may comprise a colorant.

In some embodiments, the fastener component may include a transferable fastening component that is initially applied to the reusable belt and transferred to the absorbent chassis when the reusable belt is removed therefrom. For example, the transferable fastener component may include a transferable adhesive (e.g., a hotmelt adhesive) that is applied to the reusable belt and used to temporarily attach the reusable belt to the absorbent chassis. When the reusable belt is removed from the absorbent chassis, the transferable adhesive is further transferred to the absorbent chassis and disposed with the used/soiled absorbent chassis. With these embodiments, the reusable belt formation unit 2404 can form (or receive) the reusable belt with the transferable adhesive applied thereto. The assembly unit 2406 can further temporarily attach the reusable belt to the absorbent chassis via the transferable adhesive to form a pre-assembled wearable absorbent article. In some implementations of these embodiments, a corresponding attachment area of the absorbent chassis (e.g., on the front and/or back waist regions) may be surface treated (e.g., by the absorbent chassis formation unit 2402) to attract the transferable fastener component. The corresponding attachment area may also be formed with a material adapted to attract the transferable fastener component, such as a polymer film.

The pre-assembled wearable absorbent article may further be adapted for wear in the pre-assembled form (e.g., without removing or re-attaching the belt for its first use). Thereafter, the reusable belt may be removed from the absorbent chassis and the transferable adhesive will be transferred to the disposable chassis. In some implementations of these embodiments, the reusable belt with the transferable fastener component removed may thereafter be used with additional absorbent chassis that have one or more fastener components formed thereon for further re-attaching the reusable belt thereto. With these implementations, a first absorbent chassis formation unit 2402 may be adapted to form the absorbent chassis excluding fastener components that are used for pre-assembly with a belt using a transferable attachment component on the belt. A second apparatus chassis formation unit 2402 may further be adapted to form additional absorbent chassis with attachment components formed thereon to provide for removably attaching them to a reusable belt with the transferable attachment component once removed. The pre-assembled wearable absorbent article formed with the transferable attachment component on the belt and the additional absorbent chassis may further be packaged together in a single package.

The architecture of system 2400 can vary. For example, in some embodiments, each of the absorbent chassis formation unit 2402, the reusable belt formation unit 2404 and the assembly unit 2406 may be deployed as separate machines connected to one another via one or more assembly lines. With these embodiments, the absorbent chassis formation unit 2402 can independently form the absorbent chassis, the reusable belt formation unit 2404 can independently form the reusable belts, and the assembly unit 2406 can receive the chassis and reusable belts separately form in association with performing the pre-assembly process. Additionally, or alternatively, one or more of the absorbent chassis formation unit 2402, the reusable belt formation unit 2404 and the assembly unit 2406 may be deployed in the same machine. Still in other embodiments, one or more individual units of the absorbent chassis formation unit 2402 (e.g., one or more of the core assembly unit 2504, the first series assembly unit 2506, the second series assembly unit 2508, the fastener assembly unit 2510, the cutting unit 2512 and the folding unit 2514) may be deployed in the reusable belt formation unit and/or the assembly unit 2406. Likewise, one or more individual units of the reusable belt assembly unit 2404 (e.g., one or more of elastic portion assembly unit 2702, the cutting unit 2704, the ring belt fusing unit 2706, the front/back portion unit 2708, the opposing ends unit 2710, the fastener assembly unit 2712, the belt parts attachment assembly unit 2714, and landing zone piece unit 2716) may be deployed in the absorbent chassis formation unit 2402 and/or the assembly unit 2406.

FIG. 28 illustrates a high-level flow diagram of an example, non-limiting method 2800 forming a wearable absorbent article in accordance with one or more embodiments. In accordance with method 2800, at 2802 a system (e.g., system 2400 which may be coupled to a processor) may form (e.g., via absorbent chassis formation unit 2402) an absorbent chassis (e.g., absorbent chassis 200 and the like) comprising an absorbent core (e.g., absorbent core 306), a first lateral end (e.g., front waist end 202), a second lateral end (back waist end 216), and a length in a longitudinal direction extending between the first lateral end and the second lateral end. At 2804, method 2800 may further comprise forming, by the system, a reusable belt (e.g., via reusable belt formation unit 2904). At 2806, method 2800 may further comprise attaching, by the system (e.g., via the assembly unit 2406), the reusable belt to the absorbent chassis via at least one temporary fastener component formed on at least one of the absorbent chassis or the reusable belt, resulting in formation of a wearable absorbent article (e.g., wearable absorbent article 106 and the like).

FIG. 29 illustrates a high-level flow diagram of another example, non-limiting method 2900 forming a wearable absorbent article in accordance with one or more embodiments. In accordance with method 2900, at 2902 a system (e.g., system 2400) may form (e.g., via absorbent chassis formation unit 2402) an absorbent chassis comprising an absorbent core (e.g., absorbent core 306), a first lateral end (e.g., front waist end 202), a second lateral end (back waist end 216), and a length in a longitudinal direction extending between the first lateral end and the second lateral end. At 2904, method 2900 may further comprise forming a reusable belt by the system (e.g., via reusable belt formation unit 2904). At 2906, method 2900 may further comprise attaching, by the system (e.g., via the assembly unit 2406), the reusable belt to the absorbent chassis via at least one transferable fastener component formed on the reusable belt, resulting in formation of a wearable absorbent article, wherein the at least one transferable fastener component is capable of transferring to the absorbent chassis after detachment of the reusable belt from the absorbent chassis.

FIG. 30 illustrates a block diagram of an example, non-limiting multi-piece absorbent article manufacturing system (hereinafter system 3000) that facilitates manufacturing the multi-piece absorbent articles described with reference to FIGS. 18A-22 in accordance with one or more embodiments of the disclosed subject matter. System 3000 may include same or similar components as system 2400 with the addition of absorbent insert formation unit 3002, crotch piece formation unit 3304 and outer shell formation unit 3306. Repetitive description of like elements employed in respective embodiments is omitted for sake of brevity.

The absorbent insert formation unit 3002 may include one or more apparatuses adapted to perform a variety of manufacturing processes for forming absorbent inserts (e.g., absorbent insert 1906 and the like) adapted to removably attach to a crotch piece (e.g., crotch piece 1904 and the like) of a multi-piece reusable belt and/or an outer shell (e.g., outer shell 2302). The absorbent insert formation unit 3002 may employ same or similar manufacturing units/elements as the absorbent chassis formation unit 2402 yet adapted to form absorbent inserts as opposed to absorbent chassis. In this regard, with reference to FIGS. 25 and 30, the absorbent insert formation unit 3002 may various assembly units including a fastener assembly unit 2512 adapted to form an one or more temporary attachment components on the garment-facing surface of the insert (e.g., adhesive layer 2102 with a protective layer 2104 and in some implementations without a protective layer 2104 to facilitate pre-assembly). The absorbent insert formation unit 3002 may also include a layer assembly unit 2502 adapted to assemble/combine the topsheet with the absorbent core and optionally one or more layers of a backsheet, a cutting unit 2516 adapted to cut a continuous web/sheet of layered materials into discrete absorbent inserts, and a folding unit 2518 adapted to fold the absorbent inserts.

The crotch piece formation unit 3004 may include one or more apparatuses adapted to perform a variety of manufacturing processes for forming reusable crotch pieces (e.g., crotch piece 1902, crotch piece 2000, and the like) adapted to receive an absorbent insert (e.g., absorbent insert 1906) and removably attach to a reusable belt to form a wearable absorbent article (e.g., wearable absorbent article 1910, wearable absorbent article 2206, and the like). The crotch piece formation unit 3004 may employ same or similar manufacturing units/elements as the reusable belt formation unit 2404 yet adapted to form crotch pieces meant to extend through the crotch region of the wearer out of one or more durable and/or semi-durable materials as opposed to other pieces of reusable belts disclosed herein. The outer shell formation unit 3006 may include one or more apparatuses adapted to perform a variety of manufacturing processes for forming outer shells (e.g., outer shell 2302 and the like) adapted to receive an absorbent insert (e.g., absorbent insert 1906). The outer shell formation unit 3006 may employ same or similar manufacturing units/elements as crotch piece formation unit and/or reusable belt formation unit 2404 yet adapted to form outer shells (or outer covers) having waist and crotch regions out of one or more durable and/or semi-durable materials as opposed to absorbent chassis and reusable belts.

In some implementations of system 3000, the absorbent insert formation unit 3002, the crotch piece formation unit 3004 and the outer shell formation unit 3006 may be correspond to separate machines/assembly lines adapted to form absorbent inserts, crotch pieces and outer shells as separate pieces that may be packaged and sold separately. Additionally, or alternatively, the assembly unit 2406 may include or one or more apparatuses adapted to pre-assemble the wearable absorbent articles described with reference to FIGS. 19-23 using the absorbent inserts, crotch pieces, outer shells and reusable belts. In this regard, the pre-assembling process can include attaching the absorbent insert to the absorbent inset attachment zone 1904 of the crotch piece and/or the outer shell via the adhesive layer on the garment-facing surface of the absorbent insert. In some implementations involving the crotch piece, the pre-assembling process may also include attaching a reusable belt to the crotch piece via the one or more temporary fastener components formed on the reusable belt and/or the crotch piece. These pre-assembled wearable absorbent articles may be packaged with additional absorbent inserts with which the reusable outer shell and/or the reusable belt including the crotch piece may be used. The control unit 2410 can also include hardware and/or software that provides for controlling one or more operations of the absorbent insert formation unit 3002, the crotch piece formation unit 3304 and/or the outer shell formation unit 3306.

FIG. 31 illustrates a high-level flow diagram of another example, non-limiting method 3100 forming a wearable absorbent article in accordance with one or more embodiments. In accordance with method 3100, at 3102 a system which may be coupled to a processor (e.g., system 3000)

may form (e.g., via absorbent insert formation unit 3102) an absorbent insert (e.g., absorbent insert 1906 and the like) comprising an absorbent core (e.g., absorbent core 306), a first lateral end (e.g., first lateral end 2002), a second lateral end (second lateral end 2004), and a length in a longitudinal direction extending between the first lateral end and the second lateral end. At 3104, method 3100 may further comprise forming, by the system (e.g., via outer shell formation unit 3304), an outer cover (e.g., outer shell 2302) configured for wear around a lower abdomen of a wearer, the outer cover comprising a crotch region (e.g., crotch region 2308) and a waist region (e.g., waist region 2306). At 3106, method 3100 may further comprise attaching, by the system (e.g., via the assembly unit 2406), the absorbent insert to the outer cover via at least one temporary fastener component formed on at least one of the outer cover or the absorbent insert, resulting in formation of a wearable absorbent article (e.g., wearable absorbent article 2304 and the like).

FIG. 32 illustrates a block diagram of an example, non-limiting multi-piece absorbent article packaging system (hereinafter system 3200) that facilitates packaging the wearable absorbent articles described with reference to FIGS. 1-23D and their component parts in accordance with one or more embodiments of the disclosed subject matter. System 3200 provides for packaging the multi-piece absorbent articles and their components. In some embodiments, system 3200 can be operationally coupled to system 2400. For example, one or more assembly lines associated with system 2400 may be linked to system 3200 to provide the pre-assembled wearable absorbent articles and/or the individual components thereof to the corresponding packaging units for packaging thereof. Similar to system 24000, system 3200 can include machine executable components that may be controlled by the control unit 2410 as coupled thereto by bus 2408. Repetitive description of like elements employed in respective embodiments is omitted for sake of brevity. These machine executable components include a pre-assembled combination packaging unit 3202, a reusable belt packaging unit 3204, an absorbent chassis packaging unit 3206, an absorbent insert packaging unit 3208 and an outer shell packaging unit 3210.

With reference to FIGS. 30 and 32, the pre-assembled combination packaging unit 3202 may be adapted to package one or more pre-assembled wearable absorbent articles received from the assembly unit 2406 together with replacement disposable absorbent chassis (e.g., received from the absorbent chassis formation unit 2402) or absorbent inserts (e.g., received from the absorbent insert formation unit 3002) in a pre-assembled combination package 3212. The reusable belt packaging unit 3204 may be adapted to package one or more reusable belts (e.g., received from the reusable belt formation unit 2404) into a reusable belt package 3214 that does not include the absorbent chassis and/or absorbent insert. In implementations involving a crotch piece, the crotch piece may be included in the reusable belt package 3214. The absorbent chassis packaging unit 3206 may be adapted to package one or more absorbent chassis (e.g., received from the absorbent chassis formation unit 2402) adapted for use with a reusable belt into an absorbent chassis package 3216. In some implementations, the reusable belt may be included in the absorbent chassis package as unattached the absorbent chassis. The absorbent insert packaging unit 3208 may be adapted to package one or more absorbent inserts (e.g., received from the absorbent insert formation unit 3002) into an absorbent insert package 3218. The out and an outer shell packaging unit 3210 may be adapted to package one or more outer shells (e.g., received from the outer shell formation unit 3006) into an outer shell package 3220.

FIG. 32 illustrates a high-level flow diagram of another example, non-limiting method 3200 forming and packaging wearable absorbent articles in accordance with one or more embodiments. In accordance with method 3300, at 3302 a first apparatus (e.g., a first machine or apparatus comprising the absorbent chassis formation unit 2402), may form an absorbent chassis comprising an absorbent core, a first lateral end, a second lateral end, and a length in a longitudinal direction extending between the first lateral end and the second lateral end. At 3304, method 3300 comprises providing (or receiving) a reusable belt (e.g., by the reusable belt formation unit 2404). At 3306, method 3300 further comprises using the first apparatus to attach the reusable belt to the absorbent chassis by at least one temporary fastener component to form a wearable article (e.g., via the assembly unit 2406). At 3308, method 3300 comprises using a second apparatus (e.g., a second apparatus comprising a separate absorbent chassis formation unit 2402) to form additional absorbent chassis configured to removably attach to the reusable belt, the additional absorbent chassis respectively comprising absorbent cores, first lateral ends, second lateral ends, and lengths in a longitudinal direction extending between the first lateral ends and the second lateral ends. At 3310, method further comprises packaging the wearable absorbent article and one or more additional absorbent chassis in a single package 3310 (e.g., via the multi-piece absorbent article packaging system and the pre-assembled combination packaging unit 3202).

EXAMPLES/COMBINATIONS

A1. An absorbent article, comprising:
an absorbent chassis comprising an absorbent core, a first lateral end, a second lateral end, and a length in a longitudinal direction extending between the first lateral end and the second lateral end; and
a belt for wear around a waist of a wearer that is operatively engageable with the first lateral end and the second lateral end, wherein the absorbent chassis is disposable, and the reusable belt is reusable with and re-attachable to one or more additional absorbent chassis.

B1. The absorbent article according to Paragraph A1, wherein the belt comprises a continuous ring of at least one material, wherein at least a portion of the continuous ring is expandable.

C1. The absorbent article according to Paragraphs A1 or B1, wherein the belt is formed with one or more semi-durable materials.

D1. The absorbent article according to any one of Paragraphs A1-C1, wherein the one or more semi-durable materials are selected from the group consisting of: a thermoplastic material, a nonwoven material, an elastic material, a non-textile material, a thin-film material, and an adhesive/polymeric composition.

E1. The absorbent article according to any one of Paragraphs A1-D1, wherein the belt comprises two or more layers of adhesively bonded materials.

F1. The absorbent article according to any one of Paragraphs A1-D1, wherein the belt comprises two or more layers of adhesively bonded materials.

G1. The absorbent article according to any one of Paragraphs A1-F1, wherein an entirety of the belt comprises one or more launderable or laundering resistant materials.

H1. The absorbent article according to any one of Paragraphs A1-G1 wherein the belt is formed with one or more durable materials selected from the group consisting of a knitted material, a textile material, a cotton material, and a polyester material.

I1. The absorbent article according to any one of Paragraphs A1-H1, wherein the belt is formed with a combination of one or more semi-durable materials and one or more durable materials.

J1. The absorbent article according to any one of Paragraphs A1-I1, wherein the absorbent chassis further comprises a fastener component on a garment-facing surface of at least one of the first lateral end or the second lateral end that removably attaches with a wearer-facing surface of the belt.

K1. The absorbent article according to any one of Paragraphs A1-J1, wherein the fastener component is selected from the group consisting of an adhesive, a hook fastener, or combinations thereof.

L1. The absorbent article according to any one of Paragraphs A1-K1, wherein fastener component comprises a first fastener component and wherein the belt further comprises a second fastener component on the wearer-facing surface that removably attaches to the first fastener component.

M1. The absorbent article according to any one of Paragraphs A1-L1, wherein the absorbent chassis further comprises a topsheet and a backsheet, and wherein the absorbent core is disposed between the topsheet and backsheet.

N1. The absorbent article according to any one of Paragraphs A1-M1, wherein the belt further comprises a crotch piece comprising one or more layers of a semi-durable material that connect to the continuous ring and cover at least a portion of the length of the absorbent chassis.

O1. The absorbent article according to any one of Paragraphs A1-N1. wherein at least a portion of the crotch piece is permanently bonded to continuous ring.

P1. The absorbent article according to any one of Paragraphs A1-O1, wherein at least one of absorbent chassis or the reusable belt further comprises indicia to assist with attachment of the reusable belt to the absorbent chassis and positioning around the waist.

Q1. The absorbent article according to any one of Paragraphs A1-P1, wherein the absorbent chassis further comprises a sleeve through which the belt is inserted.

R1. The absorbent article according to any one of Paragraphs A1-Q1, wherein the belt comprises two or more pieces that removably attach to and connect the first lateral end and the second lateral end.

S1. The absorbent article according to Paragraph R1 and any one of Paragraphs A1-Q1, wherein the two or more pieces comprise a first side piece that removably attaches to and connects the first lateral end and the second lateral end on a first side of the waist, and a second side piece that removably attaches to and connects the first lateral end and the second lateral end on a second side of the waist.

T1. The absorbent article according to Paragraph R1 and any one of Paragraphs A1-S1, wherein the first side piece and the second side piece respectively have a first lateral edge, a second lateral edge and width in a longitudinal direction extending between the first lateral edge and the second lateral edge, wherein the second lateral edge is shorter than the first lateral edge.

U1. The absorbent article according to Paragraph R1 and any one of Paragraphs A1-T1, wherein the two or more pieces comprise a front piece that removably attaches to and connects to the first lateral end adjacent to an abdomen of the wearer, and a back piece that removably attaches to and connects to the second lateral end and opposite sides of the front piece.

V1. The absorbent article according to Paragraph R1 any one of Paragraphs A1-PU, wherein the absorbent chassis further comprises a back sleeve formed on the second lateral end through which the back piece is inserted.

W1. The absorbent article according to Paragraph R1 and any one of Paragraphs A1-V1, wherein opposite sides of the back piece comprise a first fastener component that removably attaches to a second fastener component on the front piece.

X1. The absorbent article according to Paragraph R1 and any one of Paragraphs A1-W1, wherein the two or more pieces comprise a first lateral piece, a second lateral piece, and a crotch piece comprising one or more layers of a semi-durable material that removably attach to at least of the first lateral piece or the second lateral piece and cover at portion of the length of the absorbent chassis.

Y1. The absorbent article according to any one of Paragraphs A1-X1, wherein belt comprises a reusable strip bel comprising two opposing ends connected to one another by a strip of material, the strip belt being adapted to wrap around a portion of a waist of a wearer and comprising one or more fastening components, wherein the first lateral end is operatively engageable with the one or more first fastening components.

A2. A method, comprising:
 forming, by a system, an absorbent chassis comprising an absorbent core, a first lateral end, a second lateral end, and a length in a longitudinal direction extending between the first lateral end and the second lateral end;
 forming, by the system, a reusable belt; and
 attaching, by the system, the reusable belt to the absorbent chassis via at least one temporary fastener component formed on at least one of the absorbent chassis or the reusable belt, resulting in formation of a wearable absorbent article.

B2. The method according to Paragraph A2, wherein the attaching comprises connecting the first lateral end and the second lateral end with the reusable belt.

C2. The method according to any one of Paragraphs A2-C2, wherein the reusable belt consists of durable and/or semi-durable materials.

D2. The method according to any one of Paragraphs A2-C2, wherein the reusable belt comprises a continuous ring of at least one material and wherein the at least one material comprises a semi-durable material.

E2. The method according to any one of Paragraphs A2-D2, wherein the reusable belt comprises a multi-piece belt.

F2. The method according to any one of Paragraphs A2-E2, wherein forming the reusable belt comprises adhesively bonding or thermally bonding two or more layers of semi-durable or durable material to one another.

G2. The method according to any one of Paragraphs A2-F2, wherein the absorbent chassis is disposable and the at least one temporary fastener component provides for detaching the reusable belt from the absorbent chassis and reattaching the reusable belt to one or more additional absorbent chassis.

H2. The method according to any one of Paragraphs A2-G2, wherein the at least one temporary fastener component comprises a first temporary fastener component formed on a garment-facing surface of at least one of the first lateral end or the second lateral end and a second temporary fastener component formed on a wearer-facing surface of the reusable belt that removably attaches to the first temporary fastener component.

I2. The method according to Paragraph H2 and any one of Paragraphs A2-H2, wherein the at least one temporary fastener component comprises a non-crystalized adhesive.

J2. The method according to any one of Paragraphs A2-I2, wherein the at least one temporary fastener component comprises a first temporary fastener component formed on at least one of the first lateral end or the second lateral end and a second temporary fastener component formed on the reusable belt that removably attaches to the first temporary fastener component.

K2. The method according to any one of Paragraphs A2-J2, wherein the method is performed using a single manufacturing machine configured to form the absorbent chassis, form the reusable belt and attach the reusable belt to the absorbent core via the at least one temporary fastener component.

L2. The method according to any one of Paragraphs A2-K2, wherein the single manufacturing machine comprises a first component that forms the absorbent chassis, a second component that forms the reusable belt and a third component that attaches the reusable belt to the absorbent chassis via the at least one temporary fastener component.

M2. The method according to any one of Paragraphs A2-L2, further comprising:

forming, by the system, a crotch comprising one or more layers of a semi-durable material; and attaching, by the system, the crotch piece to the reusable belt over at least a portion of the length of the absorbent chassis.

A3. A method comprising:

forming, by a first apparatus, an absorbent chassis comprising an absorbent core, a first lateral end, a second lateral end, and a length in a longitudinal direction extending between the first lateral end and the second lateral end;

providing a reusable belt;

using the first apparatus to attach the reusable belt to the absorbent chassis by at least one temporary fastener component to form a wearable article; and using a second apparatus to form additional absorbent chassis configured to removably attach to the reusable belt, the additional absorbent chassis respectively comprising absorbent cores, first lateral ends, second lateral ends, and lengths in a longitudinal direction extending between the first lateral ends and the second lateral ends.

B3. The method according to Paragraphs A3, further comprising packaging the wearable article and one or more of the additional absorbent chassis in a single package.

C3. The method according to any one of Paragraphs A3-B3, further comprising forming a fastening component on each of the additional absorbent chassis.

D3. The method according to any one of Paragraphs A3-C3, wherein the reusable belt consists of durable and/or semi-durable materials.

F3. The method according to any one of Paragraphs A3-D3, wherein the reusable belt comprises a continuous ring of at least one material and wherein the at least one material comprises a semi-durable material.

G3. The method according to any one of Paragraphs A3-F3, wherein the reusable belt comprises a multi-piece belt.

H3. The method according to any one of Paragraphs A3-G3, wherein the at least one temporary fastener component comprises a non-crystalized adhesive formed on the absorbent chassis.

I3. The method according to any one of Paragraphs H3, wherein the non-crystalized adhesive comprises a hotmelt adhesive.

A4. A method comprising:

forming, by a system, an absorbent chassis comprising an absorbent core, a first lateral end, a second lateral end, and a length in a longitudinal direction extending between the first lateral end and the second lateral end;

forming, by the system, a reusable belt; and attaching, by the system, the reusable belt to the absorbent chassis via at least one transferable fastener component formed on the reusable belt, resulting in formation of a wearable absorbent article, wherein the transferable fastener component is capable of transferring to the absorbent chassis after detachment of the reusable belt from the absorbent chassis.

B4. The method according to Paragraph A4, further comprising treating, by the system, a surface of the absorbent chassis to attract the at least one transferable fastener component.

C4. The method according to any one of Paragraphs A4-B4, further comprising forming, by the system, an attachment area on the absorbent chassis to which the at least one transferable fastener component is adapted to attach and transfer to after the detachment.

D4. The method according to any one of Paragraphs A4-C4, wherein the at least one transferable fastener component comprises an adhesive.

E4. The method according to any one of Paragraphs A4-D4, wherein the adhesive comprises a hotmelt adhesive.

F4. The method according to any one of Paragraphs A4-E4 further comprising packaging the wearable article and one or more additional absorbent chassis in a single package.

G4. The method according to any one of Paragraphs A4-F4, further comprising forming a fastening component on each of the additional absorbent chassis.

H4. The method according to any one of Paragraphs A4-G4, wherein the reusable belt consists of durable and/or semi-durable materials.

I4. The method according to any one of Paragraphs A4-H4, wherein the reusable belt comprises a continuous ring of at least one material and wherein the at least one material comprises a semi-durable material.

J4. The method according to any one of Paragraphs A4-I4, wherein the reusable belt comprises a multi-piece belt.

Hysteresis Test Method

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23 deg. C.+−2 deg. C. and relative humidity of 50%+−2%. The samples are conditioned for 24 hours prior to testing.

1. Select a 2.54 cm (width), 7.62 cm (length) sample of the material for testing. In some cases, if it is not be possible to get a 2.54 cm×7.62 cm sample, a smaller sample may be used, but a gage length of 25 mm must still be used. If the sample is activated or includes an activation portion, the length of the sample is taken in the direction of activation.

2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.

4. Set the distance between the grips at 25 mm.

5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length (lini), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6(a) First cycle loading: Pull the sample to a strain of 50% at a constant cross head speed of 254 mm/min.

6(b) First cycle unloading: Hold the sample at 50% strain for 30 seconds and then return the crosshead to its starting position (0% strain) at a constant cross head speed of 254 mm/min. Hold the sample in the unstrained state for 1 minute.

6(c) Set from second cycle loading: Pull the sample at a constant cross head speed of 254 mm/min, till it reaches a load of 0.05 N/25.4 mm (0.020 N/cm). Record the extended gauge length (lext). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.

6(d) Second cycle unload: Next, return the crosshead to its starting position (zero strain) at a constant cross head speed of 254 mm/min.

Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):

1. Loads at 25% strain and 50% strain (N/cm)
2. % set (Percent Strain measured at a second cycle load of 0.02N/cm);
3. % set=(lext−lini)/lini*100%.

Five repetitions are done on each sample and the average and standard deviation reported.

The Hysteresis Test can be suitably modified depending on the expected attributes and/or properties of the particular material sample to be measured. For example, the Test can be suitably modified where a sample of the length and width specified above are not available from the subject article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method comprising:
   forming an absorbent chassis comprising an absorbent core, a first lateral end, a second lateral end, and a length in a longitudinal direction extending between the first lateral end and the second lateral end;
   forming, a reusable belt; and
   attaching the reusable belt to the absorbent chassis via at least one temporary fastener component formed on at least one of the absorbent chassis or the reusable belt, resulting in formation of a wearable absorbent article, wherein the reusable belt comprises a front portion, a back portion, and side portions, wherein each of the front portion and the back portion have a central portion with a smaller longitudinal length relative to a longitudinal length of the side portions;
   wherein at least one of the front portion and the back portion is divided into an upper part and a lower part physically split apart from one another, and wherein the upper part forms a continuous ring and the lower part comprises two opposing straps.

2. The method of claim 1, wherein the attaching comprises connecting the first lateral end and the second lateral end with the reusable belt.

3. The method of claim 1, wherein the reusable belt consists of durable and/or semi-durable materials.

4. The method of claim 1, wherein the reusable belt comprises a continuous ring of at least one material and wherein the at least one material comprises a semi-durable material.

5. The method of claim 1, wherein the reusable belt comprises a multi-piece belt.

6. The method of claim 1, wherein forming the reusable belt comprises adhesively bonding two or more layers of semi-durable or durable material to one another.

7. The method of claim 1, wherein forming the reusable belt comprises thermally bonding two or more layers of semi-durable or durable material to one another.

8. The method of claim 1, wherein the absorbent chassis is disposable and the at least one temporary fastener component provides for detaching the reusable belt from the absorbent chassis and reattaching the reusable belt to one or more additional absorbent chassis.

9. The method of claim 8, wherein the at least one temporary fastener component comprises a non-crystalized adhesive.

10. The method of claim 8, wherein the at least one temporary fastener component comprises a first temporary fastener component formed on at least one of the first lateral end or the second lateral end and a second temporary fastener component formed on the reusable belt that removably attaches to the first temporary fastener component.

11. The method of claim 1, wherein the method is performed using a single manufacturing machine configured to form the absorbent chassis, form the reusable belt and attach the reusable belt to the absorbent core via the at least one temporary fastener component.

12. The method of claim 11, wherein the single manufacturing machine comprises a first component that forms the absorbent chassis, a second component that forms the reusable belt and a third component that attaches the reusable belt to the absorbent chassis via the at least one temporary fastener component.

13. The method of claim 1, further comprising:

forming a crotch piece comprising one or more layers of a semi-durable material; and attaching the crotch piece to the reusable belt over at least a portion of the length of the absorbent chassis.

14. The method of claim 1, wherein the reusable belt comprises a landing zone piece, wherein the landing zone piece removably attaches the reusable belt to the absorbent chassis, and wherein the landing zone piece is disposable.

* * * * *